(12) United States Patent
Chao et al.

(10) Patent No.: US 11,891,450 B2
(45) Date of Patent: Feb. 6, 2024

(54) ANTI-CD47 AGENT-BASED TREATMENT OF CD20-POSITIVE CANCER

(71) Applicant: Forty Seven, Inc., Foster City, CA (US)

(72) Inventors: Mark Ping Chao, Mountain View, CA (US); Chris Hidemi Mizufune Takimoto, Menlo Park, CA (US); Jens-Peter Volkmer, Menlo Park, CA (US)

(73) Assignee: Forty Seven, Inc., Foster City, CA (US)

( * ) Notice: Subject to any disclaimer, the term of this patent is extended or adjusted under 35 U.S.C. 154(b) by 480 days.

(21) Appl. No.: 16/272,350

(22) Filed: Feb. 11, 2019

(65) Prior Publication Data

US 2019/0248915 A1 Aug. 15, 2019

Related U.S. Application Data

(60) Provisional application No. 62/743,875, filed on Oct. 10, 2018, provisional application No. 62/743,060, filed on Oct. 9, 2018, provisional application No. 62/678,468, filed on May 31, 2018, provisional application No. 62/629,340, filed on Feb. 12, 2018.

(51) Int. Cl.
| | |
|---|---|
| *C07K 16/28* | (2006.01) |
| *C07K 16/30* | (2006.01) |
| *A61P 35/00* | (2006.01) |
| *A61K 39/395* | (2006.01) |
| *A61K 39/00* | (2006.01) |

(52) U.S. Cl.
CPC ........ *C07K 16/30* (2013.01); *A61K 39/39558* (2013.01); *A61P 35/00* (2018.01); *C07K 16/2803* (2013.01); *C07K 16/2887* (2013.01); *A61K 2039/505* (2013.01); *A61K 2039/507* (2013.01); *A61K 2039/545* (2013.01); *A61K 2039/55* (2013.01); *A61K 2039/804* (2018.08); *C07K 2317/24* (2013.01); *C07K 2317/732* (2013.01)

(58) Field of Classification Search
CPC ................ C07K 16/30; C07K 16/2803; C07K 16/2887; C07K 2317/24; C07K 2317/732; A61K 39/39558; A61K 2039/55; A61K 2039/804; A61K 2039/505; A61K 2039/507; A61K 2039/545; A61P 35/00
See application file for complete search history.

(56) References Cited

U.S. PATENT DOCUMENTS

| | | | |
|---|---|---|---|
| 8,728,476 B2 | 5/2014 | van den Berg | |
| 8,758,750 B2 | 6/2014 | Weissman et al. | |
| 9,352,037 B2 | 5/2016 | van den Berg | |
| 9,790,275 B2 | 10/2017 | van den Berg | |
| 9,920,122 B2 | 3/2018 | van den Berg | |
| 10,081,680 B2 | 9/2018 | Weiskopf et al. | |
| 10,287,351 B2 | 5/2019 | van den Berg | |
| 2005/0180972 A1 | 8/2005 | Wahl et al. | |
| 2007/0041981 A1 | 2/2007 | Howard et al. | |
| 2008/0107654 A1 | 5/2008 | Kikuchi et al. | |
| 2009/0191202 A1 | 7/2009 | Jamieson et al. | |
| 2011/0038870 A1 | 2/2011 | van den Berg | |
| 2014/0242095 A1 | 8/2014 | Wang et al. | |
| 2016/0008429 A1* | 1/2016 | Willingham et al. ....................... A61K 38/1816 |
| 2018/0155424 A1 | 6/2018 | van den Berg | |
| 2019/0023784 A1 | 1/2019 | Chalons-Cottavoz et al. | |
| 2019/0119396 A1 | 4/2019 | Liu et al. | |

FOREIGN PATENT DOCUMENTS

| | | |
|---|---|---|
| CN | 103665165 B | 2/2016 |
| CN | 106084052 A | 11/2016 |
| CN | 106456748 A | 2/2017 |
| EP | 2282772 | 2/2011 |
| WO | WO 1999/040940 | 8/1999 |
| WO | WO 2001/048020 | 7/2001 |
| WO | WO 2003/072736 | 9/2003 |
| WO | WO 2008/121821 | 10/2008 |
| WO | WO 2009/091547 | 7/2009 |
| WO | WO 2009/091601 | 7/2009 |
| WO | WO 2009/131453 | 10/2009 |
| WO | WO 2011/066501 A1 | 6/2011 |
| WO | WO 2011/143624 A2 | 11/2011 |
| WO | WO 2013/109752 | 7/2013 |
| WO | WO 2014/094122 | 6/2014 |
| WO | WO 2014/123580 | 8/2014 |
| WO | WO 2015/138600 | 9/2015 |
| WO | WO 2016/023040 | 2/2016 |
| WO | WO 2017/027422 | 2/2017 |

(Continued)

OTHER PUBLICATIONS

NCT02953509, Trial of Magrolimab (Hu5F9-G4) in Combination With Rituximab or Rituximab + Chemotherapy in Participants With Relapsed/Refractory B-cell Non-Hodgkin's Lymphoma, Nov. 1, 2016 (Year: 2016).*
A. Bosly, Diffuse large B-cell lymphoma: concise review , Belg J Hematol 2011;2:57-63 (Year: 2011).*
Advani R, et al. CD47 Blockade by Hu5F9-G4 and Rituximab in Non-Hodgkin's Lymphoma. N Engl J Med. Nov. 1, 2018;379(18): 1711-1721. doi: 10.1056/NEJMoa1807315. PMID: 30380386. (Year: 2018).*

(Continued)

*Primary Examiner* — Hong Sang
(74) *Attorney, Agent, or Firm* — Choate, Hall & Stewart LLP; Rolando Medina; Melissa M. Adams

(57) ABSTRACT

Methods, kits, and compositions are provided herein that can be used to treat CD20+ cancer using an anti-CD47 agent such as an antibody. The anti-CD47 agent can be used alone or in combination with one or more additional agent such as an anti-CD20 antibody.

20 Claims, 22 Drawing Sheets

Specification includes a Sequence Listing.

(56) References Cited

FOREIGN PATENT DOCUMENTS

| WO | WO 2017/068164 | 4/2017 |
|---|---|---|
| WO | WO 2017/100462 | 6/2017 |
| WO | WO 2017/121771 | 7/2017 |
| WO | WO 2017/127707 | 7/2017 |
| WO | WO 2017/177333 | 10/2017 |
| WO | WO-2017/181033 A1 | 10/2017 |
| WO | WO 2019/023347 | 1/2019 |
| WO | WO 2019/079548 | 4/2019 |
| WO | WO 2019/079549 | 4/2019 |
| WO | WO 2019/157432 | 8/2019 |

OTHER PUBLICATIONS

Weiner GJ. Rituximab: mechanism of action. Semin Hematol. 2010;47(2):115-123. doi:10.1053/j.seminhematol.2010.01.011 (Year: 2010).*

Murawski N, et al. Optimization of rituximab for the treatment of DLBCL (I): dose-dense rituximab in the DENSE-R-CHOP-14 trial of the DSHNHL. Ann Oncol. Sep. 2014;25(9):1800-1806. doi: 10.1093/annonc/mdu208. Epub Jun. 13, 2014. PMID: 24928834. (Year: 2014).*

Chao MP, et al., Anti-CD47 antibody synergizes with rituximab to promote phagocytosis and eradicate non-Hodgkin lymphoma. Cell. Sep. 3, 2010;142(5):699-713. doi: 10.1016/j.cell.2010.07.044. PMID: 20813259; PMCID: PMC2943345. (Year: 2010).*

Davis TA et al., Single-agent monoclonal antibody efficacy in bulky non-Hodgkin's lymphoma: results of a phase II trial of rituximab. J Clin Oncol. Jun. 1999;17(6):1851-7. doi: 10.1200/JCO.1999.17.6.1851. PMID: 10561225. (Year: 1999).*

Ayi, K. et al., "CD47-SIRPα Interactions Regulate Macrophage Uptake of Plasmodium falciparum-Infected Erythrocytes and Clearance of Malaria In Vivo," Infection and Immunity, vol. 84, No. 7, Jul. 1, 2016, pp. 2002-2011.

Brochure by RituxanHycela®, "Rituxan® and Rituxan Hycela® Dosing and Administration Brochure" Issued Jun. 2017: pp. 1-45, Retrieved from the internet: https://www.rituxanhycela.com/hcp/dosing-and-administration/product-information.html.

Cameron, et al., "Myxoma virus M128L is expressed as a cell surface CD-47-like virulence factor that contributes to the downregulation of macrophage activation in vivo," Virology. Jun. 20, 2005; vol. 337, Issue 1: pp. 55-67.

Chao, et al. "CD4 is an adverse prognostic factor in non-hodgkin lymphoma and a therapeutic antibody target that synergizes with rituximab", Exp Hematol (Sep. 2009), 37(Suppl 1):S8-S9.

Chao, et al. "Therapeutic antibody targeting of CD47 synergizes with rituximab to completely eradicate human B-cell lymphoma xenografts", Blood (Nov. 2009), 114(22):1063-1064, abstract only.

Hatherley et al., "Paired Receptor Specificity Explained by Structures of Signal Regulatory Proteins Alone and Complexed with CD47," Jul. 25, 2008, Mollecular Cell, vol. 31, Issue 2: pp. 266-277.

Hatherley et al., "The Structure of the Macrophage Signal Regulatory Protein α (SIRPα) Inhibitory Receptor Reveals a Binding Face Reminiscent of That Usedby T Cell Receptors," The Journal of Biological Chemistry, May 11, 2007, vol. 282, Issue 19: pp. 14567-14575.

Hezareh, M. et al., "Effector Function Activities of a Panel of Mutants of a Broadly Neutralizing Antibody against Human Immunodeficiency Virus Type 1," Journal of Virology, vol. 75, No. 24, Dec. 2001, pp. 12161-12168.

Jaiswal, et al. "CD47 is Upregulated on Circulating Hematopoietic Stem Cells and Leukemia Cells to Avoid Phagocytosis", Cell (Jul. 2009), 138(2):271-285.

Lee et al., "Novel Structural Determinants on SIRPα that Mediate Binding to CD47," The Journal of Immunology, 2007, vol. 179: pp. 7741-7750.

Lee et al., "The Role of cis Dimerization of Signal Regulatory Protein α (SIRP α) in Binding to CD47," The Journal of Biological Chemistry, Dec. 3, 2010, vol. 285, Issue 49: pp. 37953-37963.

Liu, J., et al. "Pre-Clinical Development of a Humanized Anti-CD47 Antibody with Anti-Cancer Therapeutic Potential", PloS ONE, Sep. 21, 2015, vol. 10, Issue 9: pp. 1-23.

Majeti, et al. "CD47 is an Adverse Prognostic Factor and Therapeutic Antibody Target on Human Acute Myeloid Leukemia Stem Cells", Cell (Jul. 2009), 138(2):286-299.

Manna and Frazier, "CD47 Mediates Killing of Breast Tumor Cells via GI-Dependent Inhibition of Protein Kinase A," Cancer Research, Feb. 1, 2004, vol. 64: pp. 1026-1036.

Oldenborg, et al. "Role of CD47 as a marker of self on red blood cells". Science 2000;288:2051-4.

OSE Immunotherapeutics, "Selective anti-SIRPα antibodies: Next generation checkpoint inhibitor: Targeting pro-tumors and suppressive myeloids cells," Sep. 2017, 35 pages.

PCT International Preliminary Report on Patentability for PCT/EP2017/050508, dated Jul. 17, 2018, 6 pages.

PCT International Search Report and Written Opinion, PCT Application No. PCT/US2019/017466, dated Apr. 29, 2019, 19 pages.

PCT International Search Report and Written Opinion, PCT Application No. PCT/US2018/043699, dated Jan. 31, 2019, 13 pages.

PCT International Search Report and Written Opinion, PCT Application No. PCT/US2018/056441, dated Apr. 25, 2019, 12 pages.

PCT International Search Report and Written Opinion, PCT Application No. PCT/US2018/056442, dated Apr. 25, 2019, 10 pages.

Sehn, et al., "Introduction of Combined CHOP Plus Rituximab Therapy Dramatically Improved Outcome of Diffuse Large B-Cell Lymphoma in British Comlumbia," J. Clin. Oncol., Aug. 1, 2005, vol. 23, Issue 22: pp. 5027-5033.

Seiffert, M. et al., "Human Signal-Regulatory Protein is Expressed on Normal, but not on Subsets of Leukemic Myeloid Cells and Mediates Cullular Adhesion involving its Counterreceptor CD47," Blood, vol. 94, No. 11, Dec. 1, 1999, pp. 3633-3643.

Strohl, W., "Optimization of Fc-mediated effector functions of monoclonal antibodies," Current Opinion in Biotechnology, vol. 20, No. 6, Dec. 1, 2009, pp. 685-691.

Takenaka, K. et al., "Polymorphism in Sirpa modulates engraftment of human hematopoietic stem cells," Nature Immunology vol. 8, 2007, pp. 1313-1323.

Yanagita, T. et al., "Anti-SIRPα antibodies as a potential new tool for cancel immunotherapy," JCI Insight, vol. 2, No. 1, Jan. 12, 2017, 15 pages.

Zhao, X. et al., "CD47-signal regulatory protein-α (SIRPα) interactions form a barrier for antibody-mediated tumor cell destruction," Proceedings of the National Academy of Sciences of the United States of America, vol. 108, No. 45, pp. 18342-18347.

Abstracts from the 11th American Conference on Pharmacometrics, ACoP11, ISSN 2688-3953, vol. 2, 3 pages (Nov. 9-13, 2020).

History of Changes for Study: NCT02953509, Trial of Hu5F9 in Combination With Rituximab in Relapsed/Refractory B-cell Non-Hodgkin's Lymphoma, retrieved from: https://clinicaltrials.gov.ct2/history/NCT02953509?V_7=View#StudyPageTop, 6 pages (retrieved on Oct. 12, 2022).

English translation of Japanese Office Action dated Nov. 2, 2022, 7 pages.

Med J. Kinki Univ., 35(1):55-62 (2010). Non English; relevance explained on p. 3 of English translation of Japanese Office Action dated Nov. 2, 2022, 7 pages.

2022. 1618 Magrolimab in Combination with Rituximab + Chemotherapy in Patients with Relapsed or Refractory (R/R) Diffuse Large B-Cell Lymphoma (DLBCL). 64th ASH Annual Meeting and Exposition, Dec. 10-13, 2022, New Orleans, Louisiana.

Abrisqueta, P. et al., 4089 Anti-CD47 Antibody, CC-90002, in combination with rituximab in subjects with relapsed and/or refractory non-hodgkin lymphoma (R/R NHL), Oral and Poster Abstracts, ASH Annual Meeting, 3 pages, Monday, Dec. 9, 2019.

Narla, R. K. et al., A phase 1, Dose finding study of CC-90002 in subjects with advanced solid and hematologic cancers, Clinical Trials, NCT02367196, 9 pages, (2021).

* cited by examiner

| Response | All patients n=22 | DLBCL n=15 | Follicular Lymphoma n=7 |
|---|---|---|---|
| Objective Response Rate (ORR) | 11 (50%) | 6 (40%) | 5 (71%) |
| Partial Response (PR) | 3 (14%) | 1 (7%) | 2 (29%) |
| Complete Response (CR) | 8 (36%) | 5 (33%) | 3 (43%) |
| Disease control rate (CR+PR+SD) | 14 (64%) | 9 (60%) | 5 (71%) |

Data extraction April 2018

Figure 4B (cont)

| Patient Subset | Frequency | Precede to ORR |
|---|---|---|
| De novo | 8/15 (53%) | 2/8 (25%) |
| Transformed | 7/15 (47%) | 4/7 (57%) |
| Activated B Cell | 3/15 (20%) | 2/3 (67%) |
| Germinal Center B Cell | 6/15 (40%) | 1/6 (17%) |
| Unknown cell of origin | 6/15 (40%) | 3/6 (50%) |
| Double hit lymphoma | 3/15 (20%) | 1/3 (33%) |
| Rituximab-refractory | 14/15 (93%) | 6/14 (43%) |
| Refractory to last regimen | 9/15 (60%) | 2/9 (22%) |
| Prior autologous transplant | 2/15 (13%) | 2/2 (100%) |

Figure 10

SEQUENCE LISTING

```
<160> NUMBER OF SEQ ID NOS: 6

<210> SEQ ID NO 1
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Asn Met His Trp Val Arg Gln Ala Pro Gly Gln Arg Leu Glu Trp Met
        35                  40                  45

Gly Thr Ile Tyr Pro Gly Asn Asp Asp Thr Ser Tyr Asn Gln Lys Phe
    50                  55                  60

Lys Asp Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Arg Ala Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300
```

```
Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
            325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
            435                 440

<210> SEQ ID NO 2
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val Tyr Ser
            20                  25                  30

Asn Gly Asn Thr Tyr Leu Gly Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 3
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Ala Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser

```
                355                 360                 365
Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
    450

<210> SEQ ID NO 4
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
                20                  25                  30

His Trp Phe Gln Gln Lys Pro Gly Ser Ser Pro Lys Pro Trp Ile Tyr
            35                  40                  45

Ala Thr Ser Asn Leu Ala Ser Gly Val Pro Val Arg Phe Ser Gly Ser
        50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 5
<211> LENGTH: 448
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 5

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400
```

```
Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 6
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

ANTI-CD47 AGENT-BASED TREATMENT OF CD20-POSITIVE CANCER

CROSS REFERENCE TO RELATED APPLICATIONS

This application claims benefit of U.S. Provisional Application No. 62/629,340, filed Feb. 12, 2018; U.S. Provisional Application No. 62/678,468, filed May 31, 2018; U.S. Provisional Application No. 62/743,060, filed Oct. 9, 2018; and U.S. Provisional Application No. 62/743,875, filed Oct. 10, 2018; each of which is hereby incorporated by reference in its entirety for all purposes.

SEQUENCE LISTING

The instant application contains a Sequence Listing which has been submitted electronically in ASCII format and is hereby incorporated by reference in its entirety. Said ASCII copy, created on Feb. 11, 2019, is named 42563US_CRF_sequencelisting.txt and is 18,210 bytes in size.

BACKGROUND

CD47 has been identified as a key molecule mediating cancer cell evasion of phagocytosis by the innate immune system. CD47 appears to be an important means by which cancer cells, including cancer stem cells, overcome oftentimes intrinsic expression of their prophagocytic, "eat me," signals. The progression from normal cell to cancer cell can involve changes in genes and/or gene expression that trigger programmed cell death (PCD) and programmed cell removal (PCR). Many of the steps in cancer progression subvert multiple mechanisms of PCD, and expression of anti-phagocytic signal, CD47, may represent an important checkpoint.

CD47 expression is increased on the surface of many cancer cells from a large number of diverse human tumor types including the following primary malignancies: head and neck, melanoma, breast, lung, ovarian, pancreatic, colon, bladder, prostate, leiomyosarcoma, glioblastoma, medulloblastoma, oligodendroglioma, glioma, lymphoma, leukemia, and multiple myeloma. In murine xenograft studies, it has been shown that CD47-blocking antibodies inhibit human cancer growth and metastasis by enabling phagocytosis and elimination of cancer cells from various hematologic malignancies and several solid tumors.

CD47 serves as the ligand for SIRPα, which is expressed on phagocytic cells including macrophages and dendritic cells. When SIRPα is activated by CD47 binding, it initiates a signal transduction cascade resulting in inhibition of phagocytosis. In this way, CD47 functions as an anti-phagocytic signal by delivering a dominant inhibitory signal to phagocytic cells.

Methods for effective delivery of antibodies that block CD47 in humans with cancer are of clinical interest, and are provided herein.

SUMMARY

Disclosed herein is a method of treating a human subject having a CD20+ cancer or reducing the size of the CD20+ cancer in the human subject, comprising: (a) administering an anti-CD47 antibody to the subject at a dose of greater than or equal to 10 mg of antibody per kg of body weight; and (b) administering an anti-CD20 antibody to the subject.

In some aspects, the CD20+ cancer is a B cell cancer. In some aspects, the B cell cancer is Non-Hodgkin's lymphoma (NHL).

In some aspects, NHL is indolent lymphoma. In some aspects, indolent lymphoma is follicular lymphoma (FL). In some aspects, indolent lymphoma is marginal zone lymphoma.

In some aspects, NHL is diffuse large B cell lymphoma (DLBCL).

In some aspects, the CD20+ cancer is DLBCL, follicular lymphoma, marginal zone lymphoma, mantle cell lymphoma, chronic lymphocytic leukemia/small lymphocytic leukemia, waldenstrom's macroglobulinemia/lymphoplasmacytic lymphoma, primary mediastinal B-cell lymphoma, Burkitt's lymphoma, B-cell lymphoma unclassified, B-cell acute lymphoblastic leukemia, or post-transplant lymphoproliferative disease (PTLD), optionally wherein the CD20+ cancer is classified based on histopathology, flow cytometry, molecular classification, one or more equivalent assays, or a combination thereof. In some aspects, the CD20+ cancer is double hit lymphoma. In some aspects, the CD20+ cancer is myc-rearranged lymphoma.

In some aspects, the subject is relapsed or refractory to at least 1, 2, 3, 4, 5, 6, 7, 8, 9, 10 or greater than 10 prior lines of cancer therapy. In some aspects, the subject is refractory to rituximab. In some aspects, rituximab refractory status is a failure to respond to, or progression during, any previous rituximab-containing regimen, or progression within 6 months of the last rituximab dose. In some aspects, rituximab refractory status is a failure to respond to, or progression during, last previous rituximab-containing regimen, or progression within 6 months of the last rituximab dose.

In some aspects, the subject has follicular lymphoma (FL) and has received at least two prior systemic therapies. In some aspects, the subject has follicular lymphoma (FL) and relapsed after, or is refractory to, a rituximab-containing regimen.

In some aspects, the subject has relapsed or refractory large-B cell lymphoma after two or more lines of systemic therapy. In some aspects, the subject has de novo or transformed large-B cell lymphoma refractory to frontline therapy, or relapsed or refractory to second line salvage regimens or autologous hematopoietic cell transplantation. In some aspects, the subject has large-B cell lymphoma and relapsed after, or is refractory after two or more lines of systemic therapy including a rituximab-containing regimen.

In some aspects, the anti-CD47 antibody competes for binding to CD47 with Hu5F9-G4. In some aspects, the anti-CD47 binds to the same CD47 epitope as Hu5F9-G4. In some aspects, the anti-CD47 antibody comprises an IgG4 Fc. In some aspects, the anti-CD47 antibody comprises or consists of Hu5F9-G4.

In some aspects, the anti-CD47 antibody is administered at a dose of 10-30, 20-30, 10, 20, or 30 mg of antibody per kg of body weight. In some aspects, administration of the anti-CD47 antibody results in greater than or equal to 90% receptor saturation, optionally 90-100, 90, 91, 92, 93, 94, 95, 96, 97, 98, 99, or 100% receptor saturation, optionally wherein receptor saturation is measured using flow cytometry or an equivalent assay.

In some aspects, the anti-CD20 antibody competes for binding to CD20 with rituximab. In some aspects, the anti-CD20 antibody competes for binding to CD20 with obinutuzumab, ofatumumab, ocrelizumab, ibritumomab tiuxetan, tositumomab, iodine 131 tositumumab, a rituximab biosimilar (blitzima, ritemvia, tuxella), or ublituximab.

In some aspects, the anti-CD20 antibody binds to the same CD20 epitope as rituximab. In some aspects, the anti-CD20 antibody binds to the same CD20 epitope as obinutuzumab, ofatumumab, ocrelizumab, ibritumomab tiuxetan, tositumomab, iodine 131 tositumomab, a rituximab biosimilar (blitzima, ritemvia, tuxella), or ublituximab.

In some aspects, the anti-CD20 antibody comprises an Fc capable of at least one of ADCC and ADCP. In some aspects, the anti-CD20 antibody comprises an Fc comprising one or more modifications that results in increased ADCC and/or ADCP activity relative to wild-type Fc.

In some aspects, the anti-CD20 antibody has higher binding affinity for CD20 relative to rituximab, obinutuzumab, ofatumumab, ocrelizumab, ibritumomab tiuxetan, tositumomab, iodine 131 tositumomab, a rituximab biosimilar (blitzima, ritemvia, tuxella), or ublituximab.

In some aspects, the anti-CD20 antibody comprises or consists of rituximab. In some aspects, the anti-CD20 antibody comprises or consists of obinutuzumab, ofatumumab, ocrelizumab, ibritumomab tiuxetan, tositumomab, iodine 131 tositumomab, a rituximab biosimilar (blitzima, ritemvia, tuxella), or ublituximab.

In some aspects, the anti-CD20 antibody is administered at a dose of 375 mg/m$^2$ of antibody. In some aspects, the anti-CD20 antibody is administered once per week, once per month, or once every two months, optionally at a dose of 375 mg/m$^2$ of antibody at each relevant time point.

In some aspects, the anti-CD47 antibody and the anti-CD20 antibody are administered concurrently or sequentially, optionally wherein the anti-CD20 antibody is administered prior to the anti-CD47 antibody.

In some aspects, the anti-CD47 antibody is formulated in a pharmaceutical composition with a pharmaceutically acceptable excipient.

In some aspects, the anti-CD47 antibody is administered intravenously.

In some aspects, the anti-CD20 antibody is formulated in a pharmaceutical composition with a pharmaceutically acceptable excipient.

In some aspects, the anti-CD20 antibody is administered intravenously.

In some aspects, the anti-CD47 antibody is administered to the subject as a dose ranging from about 20 to about 67.5 mg of antibody per kg of body weight, optionally 20 to 30 mg of antibody per kg of body weight, optionally 20 mg of antibody per kg of body weight, 30 mg of antibody per kg of body weight, 45 mg of antibody per kg of body weight, 60 mg of antibody per kg of body weight, or 67.5 mg of antibody per kg of body weight.

In some aspects, the anti-CD47 antibody is administered to the subject once every week, once every 2 weeks, or once every 3 weeks.

In some aspects, a method disclosed herein further comprises administering a priming dose of the anti-CD47 antibody. In some aspects, the anti-CD47 antibody is administered to the subject as a priming dose of 1 mg of antibody per kg of body weight. In some aspects, the priming dose is administered to the subject for about 3 hours.

In some aspects, the anti-CD47 antibody is administered to the subject in a first cycle comprising a priming dose of 1 mg of antibody per kg of body weight on day 1 followed by a dose of 30 mg of antibody per kg of body weight once every week with an additional (optional) loading dose of at least 30 mg/kg (e.g., 30-50, 30, 35, 40, 45, 50 mg) on Day 11 (week 2). In some aspects, the first cycle is 4 weeks in duration. In some aspects, the anti-CD20 antibody is administered to the subject in the first cycle once every week at a dose of 375 mg/m$^2$ of antibody.

In some aspects, the anti-CD47 antibody is administered to the subject in a second cycle comprising a dose of 30 mg of antibody per kg of body weight once every 2 weeks. In some aspects, the second cycle is 4 weeks in duration. In some aspects, the anti-CD20 antibody is administered to the subject in the second cycle once every four weeks at a dose of 375 mg/m$^2$ of antibody.

In some aspects, a method disclosed herein further comprises at least one additional cycle, optionally 1, 2, 3, 4, 5, 6, 7, 8, 9, 10, 11, 12, 13, 14, 15, 16, 17, 18, 19, 20, or greater than 20 additional cycles. In some aspects, the dosing regimen of the at least one additional cycle is the same as the second cycle, optionally wherein the anti-CD20 antibody portion of the dosing regimen is discontinued after completing 6 total cycles. In some aspects, the at least one additional cycle is 4 weeks in duration.

Also disclosed herein is a method of treating a human subject having a CD20+ cancer, comprising administering an anti-CD47 antibody (e.g., Hu5F9-G4) and an anti-CD20 antibody (e.g., rituximab) to the subject for at least two distinct cycles of four weeks each, the first cycle comprising (1) administering a priming dose of anti-CD47 antibody at 1 mg of antibody per kg of body weight at time 0 (T0), (2) administering a dose of 30 mg of anti-CD47 antibody per kg of body weight once every week beginning one week after T0 with an additional (optional) loading dose of at least 30 mg/kg (e.g., 30-50, 30, 35, 40, 45, 50 mg) on Day 11 (week 2), and (3) administering a dose of 375 mg/m$^2$ of anti-CD20 antibody once every week; and the second cycle comprising (1) administering a dose of 30 mg of anti-CD47 antibody per kg of body weight once every two weeks, and (2) administering a dose of 375 mg/m$^2$ of anti-CD20 antibody once every four weeks. The second cycle can be repeated as additional cycles (e.g., third, fourth, fifth, sixth, seventh, eighth, ninth, tenth, etc.) without limit or, for example, until clinical benefit is reduced or lost. When reached and starting at Cycle 6 and beyond, anti-CD20 antibody can instead be administered to the subject at a dose of 375 mg/m$^2$ once every eight weeks. Generally, anti-CD47 antibody and anti-CD20 antibody will continue to be administered to the subject as above until the subject loses clinical benefit, e.g., via CR or death. The anti-CD47 antibody can be Hu5F9-G4. The anti-CD20 antibody can be rituximab.

Also disclosed herein is a method of treating a human subject having lymphoma, comprising administering an anti-CD47 antibody (e.g., Hu5F9-G4) and an anti-CD20 antibody (e.g., rituximab) to the subject for at least two distinct cycles of four weeks each, the first cycle comprising (1) administering a priming dose of anti-CD47 antibody at 1 mg of antibody per kg of body weight at time 0 (T0), (2) administering a dose of 30 mg of anti-CD47 antibody per kg of body weight once every week beginning one week after T0 with an additional (optional) loading dose of at least 30 mg/kg (e.g., 30-50, 30, 35, 40, 45, 50 mg) on Day 11 (week 2), and (3) administering a dose of 375 mg/m$^2$ of anti-CD20 antibody once every week; and the second cycle comprising (1) administering a dose of 30 mg of anti-CD47 antibody per kg of body weight once every two weeks, and (2) administering a dose of 375 mg/m$^2$ of anti-CD20 antibody once every four weeks. The second cycle can be repeated as additional cycles (e.g., third, fourth, fifth, sixth, seventh, eighth, ninth, tenth, etc.) without limit or, for example, until clinical benefit is reduced or lost. When reached and starting at Cycle 6 and beyond, anti-CD20 antibody can instead be administered to the subject at a dose of 375 mg/m$^2$ once every eight weeks. Generally, anti-CD47 antibody and anti-CD20 antibody will continue to be administered to the subject as above until the subject loses clinical benefit, e.g., via CR or death. The anti-CD47 antibody can be Hu5F9-G4. The anti-CD20 antibody can be rituximab.

Also disclosed herein is a method of treating a human subject having NHL, comprising administering an anti-CD47 antibody (e.g., Hu5F9-G4) and an anti-CD20 antibody (e.g., rituximab) to the subject for at least two distinct cycles of four weeks each, the first cycle comprising (1) administering a priming dose of anti-CD47 antibody at 1 mg of antibody per kg of body weight at time 0 (T0), (2) administering a dose of 30 mg of anti-CD47 antibody per kg of body weight once every week beginning one week after T0 with an additional (optional) loading dose of at least 30 mg/kg (e.g., 30-50, 30, 35, 40, 45, 50 mg) on Day 11 (week 2), and (3) administering a dose of 375 mg/m$^2$ of anti-CD20 antibody once every week; and the second cycle comprising (1) administering a dose of 30 mg of anti-CD47 antibody per kg of body weight once every two weeks, and (2) administering a dose of 375 mg/m$^2$ of anti-CD20 antibody once every four weeks. The second cycle can be repeated as additional cycles (e.g., third, fourth, fifth, sixth, seventh, eighth, ninth, tenth, etc.) without limit or, for example, until clinical benefit is reduced or lost. When reached and starting at Cycle 6 and beyond, anti-CD20 antibody can instead be administered to the subject at a dose of 375 mg/m$^2$ once every eight weeks. Generally, anti-CD47 antibody and anti-CD20 antibody will continue to be administered to the subject as above until the subject loses clinical benefit, e.g., via CR or death. The anti-CD47 antibody can be Hu5F9-G4. The anti-CD20 antibody can be rituximab.

Also disclosed herein is a method of treating a human subject having diffuse large B cell lymphoma (DLBCL), comprising administering an anti-CD47 antibody (e.g., Hu5F9-G4) and an anti-CD20 antibody (e.g., rituximab) to the subject for at least two distinct cycles of four weeks each, the first cycle comprising (1) administering a priming dose of anti-CD47 antibody at 1 mg of antibody per kg of body weight at time 0 (T0), (2) administering a dose of 30 mg of anti-CD47 antibody per kg of body weight once every week beginning one week after T0 with an additional (optional) loading dose of at least 30 mg/kg (e.g., 30-50, 30, 35, 40, 45, 50 mg) on Day 11 (week 2), and (3) administering a dose of 375 mg/m$^2$ of anti-CD20 antibody once every week; and the second cycle comprising (1) administering a dose of 30 mg of anti-CD47 antibody per kg of body weight once every two weeks, and (2) administering a dose of 375 mg/m$^2$ of anti-CD20 antibody once every four weeks. The second cycle can be repeated as additional cycles (e.g., third, fourth, fifth, sixth, seventh, eighth, ninth, tenth, etc.) without limit or, for example, until clinical benefit is reduced or lost. When reached and starting at Cycle 6 and beyond, anti-CD20 antibody can instead be administered to the subject at a dose of 375 mg/m$^2$ once every eight weeks. Generally, anti-CD47 antibody and anti-CD20 antibody will continue to be administered to the subject as above until the subject loses clinical benefit, e.g., via CR or death. The anti-CD47 antibody can be Hu5F9-G4. The anti-CD20 antibody can be rituximab.

Also disclosed herein is a method of treating a human subject having indolent lymphoma comprising administering an anti-CD47 antibody (e.g., Hu5F9-G4) and an anti-CD20 antibody (e.g., rituximab) to the subject for at least two distinct cycles of four weeks each, the first cycle comprising (1) administering a priming dose of anti-CD47 antibody at 1 mg of antibody per kg of body weight at time 0 (T0), (2) administering a dose of 30 mg of anti-CD47 antibody per kg of body weight once every week beginning one week after T0 with an additional (optional) loading dose of at least 30 mg/kg (e.g., 30-50, 30, 35, 40, 45, 50 mg) on Day 11 (week 2), and (3) administering a dose of 375 mg/m$^2$ of anti-CD20 antibody once every week; and the second cycle comprising (1) administering a dose of 30 mg of anti-CD47 antibody per kg of body weight once every two weeks, and (2) administering a dose of 375 mg/m$^2$ of anti-CD20 antibody once every four weeks. The second cycle can be repeated as additional cycles (e.g., third, fourth, fifth, sixth, seventh, eighth, ninth, tenth, etc.) without limit or, for example, until clinical benefit is reduced or lost. When reached and starting at Cycle 6 and beyond, anti-CD20 antibody can instead be administered to the subject at a dose of 375 mg/m$^2$ once every eight weeks. Generally, anti-CD47 antibody and anti-CD20 antibody will continue to be administered to the subject as above until the subject loses clinical benefit, e.g., via CR or death. The anti-CD47 antibody can be Hu5F9-G4. The anti-CD20 antibody can be rituximab.

Also disclosed herein is a method of treating a human subject having follicular lymphoma (FL), comprising administering an anti-CD47 antibody (e.g., Hu5F9-G4) and an anti-CD20 antibody (e.g., rituximab) to the subject for at least two distinct cycles of four weeks each, the first cycle comprising (1) administering a priming dose of anti-CD47 antibody at 1 mg of antibody per kg of body weight at time 0 (T0), (2) administering a dose of 30 mg of anti-CD47 antibody per kg of body weight once every week beginning one week after T0 with an additional (optional) loading dose of at least 30 mg/kg (e.g., 30-50, 30, 35, 40, 45, 50 mg) on Day 11 (week 2), and (3) administering a dose of 375 mg/m$^2$ of anti-CD20 antibody once every week; and the second cycle comprising (1) administering a dose of 30 mg of anti-CD47 antibody per kg of body weight once every two weeks, and (2) administering a dose of 375 mg/m$^2$ of anti-CD20 antibody once every four weeks. The second cycle can be repeated as additional cycles (e.g., third, fourth, fifth, sixth, seventh, eighth, ninth, tenth, etc.) without limit or, for example, until clinical benefit is reduced or lost. When reached and starting at Cycle 6 and beyond, anti-CD20 antibody can instead be administered to the subject at a dose of 375 mg/m$^2$ once every eight weeks. Generally, anti-CD47 antibody and anti-CD20 antibody will continue to be administered to the subject as above until the subject loses clinical benefit, e.g., via CR or death. The anti-CD47 antibody can be Hu5F9-G4. The anti-CD20 antibody can be rituximab.

Also disclosed herein is a method of treating a human subject having marginal zone lymphoma, comprising administering an anti-CD47 antibody (e.g., Hu5F9-G4) and an anti-CD20 antibody (e.g., rituximab) to the subject for at least two distinct cycles of four weeks each, the first cycle comprising (1) administering a priming dose of anti-CD47 antibody at 1 mg of antibody per kg of body weight at time 0 (T0), (2) administering a dose of 30 mg of anti-CD47 antibody per kg of body weight once every week beginning one week after T0 with an additional (optional) loading dose of at least 30 mg/kg (e.g., 30-50, 30, 35, 40, 45, 50 mg) on Day 11 (week 2), and (3) administering a dose of 375 mg/m$^2$ of anti-CD20 antibody once every week; and the second cycle comprising (1) administering a dose of 30 mg of anti-CD47 antibody per kg of body weight once every two weeks, and (2) administering a dose of 375 mg/m$^2$ of anti-CD20 antibody once every four weeks. The second cycle can be repeated as additional cycles (e.g., third, fourth, fifth, sixth, seventh, eighth, ninth, tenth, etc.) without limit or, for example, until clinical benefit is reduced or lost. When reached and starting at Cycle 6 and beyond, anti-CD20 antibody can instead be administered to the subject at a dose of 375 mg/m$^2$ once every eight weeks. Generally, anti-CD47 antibody and anti-CD20 antibody will continue to be administered to the subject as above until the subject loses clinical benefit, e.g., via CR or death. The anti-CD47 antibody can be Hu5F9-G4. The anti-CD20 antibody can be rituximab.

In some aspects, a method disclosed herein results in an objective response (OR) in the subject. In some aspects, a method disclosed herein results in disease control in the subject. In some aspects, a method disclosed herein results in a partial response (PR) in the subject. In some aspects, a method disclosed herein results in a complete response (CR) in the subject. In some aspects, a method disclosed herein results in stable disease (SD) in the subject. In some aspects, a method disclosed herein reduces the size of the cancer relative to baseline where baseline is determined prior to administration of anti-CD47 antibody.

In some aspects, a method disclosed herein the subject is refractory to rituximab and the method results in a reversal of refractoriness to rituximab.

In some aspects, a method disclosed herein one or both of the antibodies are administered by a medical professional, optionally a physician. In some aspects, a method disclosed herein one or both of the antibodies are administered by the subject.

In some aspects, a method disclosed herein further comprises determining the expression level of CD47 in lymphoma tissue of a subject. CD47 expression can be protein expression by immunohistochemistry, flow cytometry, mass cytometry (CyTOF), or gene expression by RNA sequencing, microarray analysis or other gene expression profiling method. In some aspects the subject has activated B-cell (ABC) DLBCL. In some aspects the subject has non-germinal center B cell (GCB) DLBCL. In some aspects, the subject has increased expression of CD47 relative to (normal) control and the anti-CD47 antibody is administered to the subject, optionally the subject has ABC or non-germinal center B cell (GCB) DLBCL.

In some aspects, a method disclosed herein further comprises administration of a Bcl-2/Bcl-xL inhibitor to the subject. A Bcl-2/Bcl-xL inhibitor can include venetoclax, navitoclax, and/or AZD0466, or others.

In some aspects, a method disclosed herein further comprises administration of a PD1/PDL1 inhibitor to the subject. In some aspects, the PD1/PDL1 inhibitor is an antibody or antigen-binding fragment thereof. A PD1/PDL1 inhibitor can include atezolizumab, avelumab, pembrolizumab, nivolumab, durvalumab, tislelizumab, and/or cemiplimab, or others.

BRIEF DESCRIPTION OF THE SEVERAL VIEWS OF THE DRAWINGS

These and other features, aspects, and advantages of the present invention will become better understood with regard to the following description, and accompanying drawings, where:

FIG. 10 shows Efficacy in Subsets of DLBCL treated on the Phase 1b/2 trial of Hu5F9-G4+rituximab in NHL.

DETAILED DESCRIPTION

Figure 1:
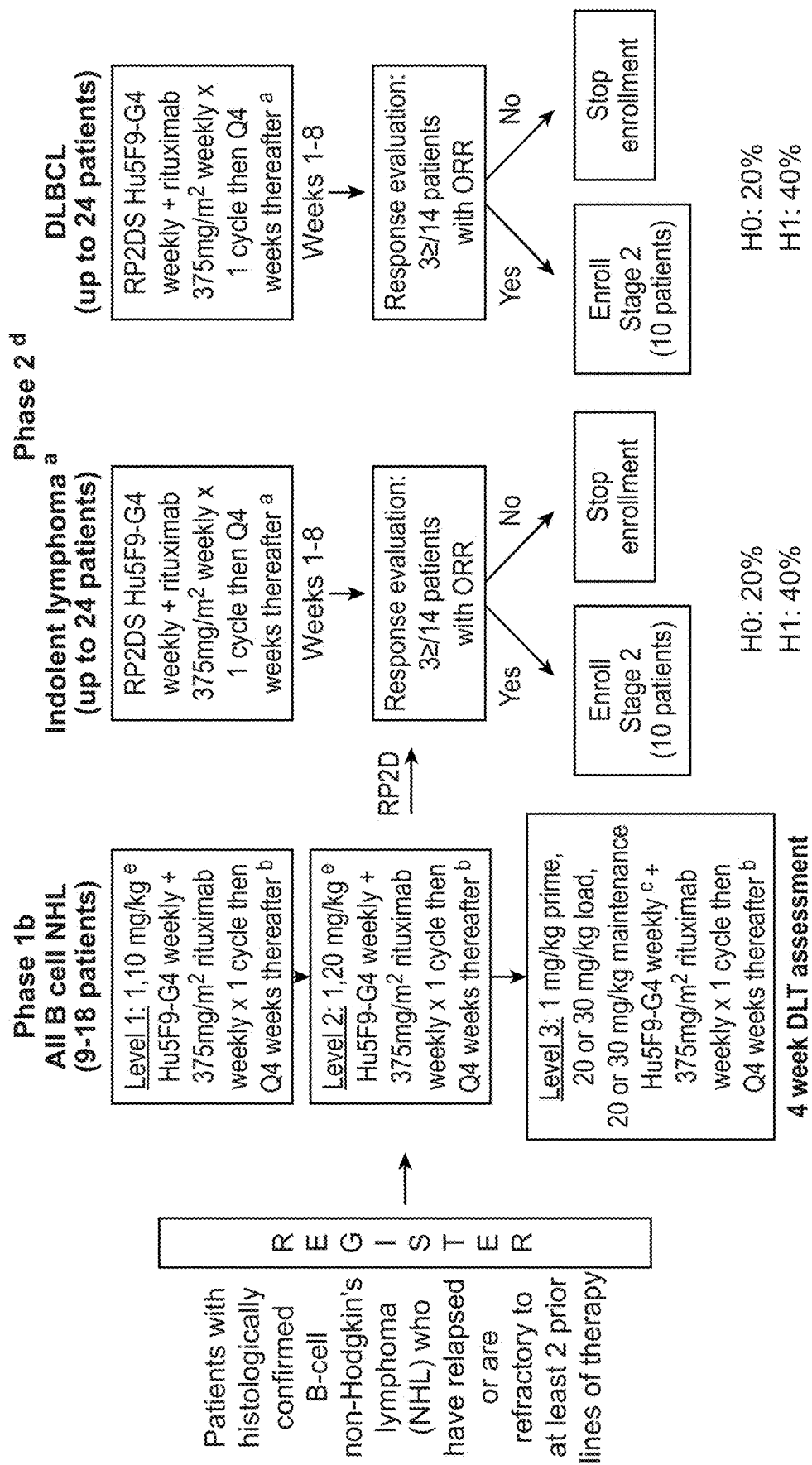
FIG. 1 shows a study design schema for: Phase 1b/2 Trial of Hu5F9-G4 in Combination with Rituximab in Patients with Relapsed/Refractory B-cell Non-Hodgkin's Lymphoma. A 5F9 priming dose (1 mg/kg) was utilized to mitigate on-target anemia, with dose escalation of the maintenance dose from 10 to 30 mg/kg in combination with rituximab in a standard 3+3 design. [a]Indolent lymphoma includes follicular and marginal zone lymphoma. [b] Treatment cycles are 4 weeks. Rituximab is given weekly at Weeks 2-4 in Cycle 1 only. Up to 6 cycles of rituximab will be given. Level 3 Hu5F9-G4 dosing regimen consists of 1 mg/kg priming dose on Day 1, then a loading dose of either 20 or 30 mg/kg twice weekly×1 week, followed by weekly maintenance doses of 20 or 30 mg/kg. Dose concentration to be determined by the CTSC. [d] Simon two-stage minimax design with an alpha of 0.1 and a power of 0.80. H0=null hypothesis; H1=alternative hypothesis. [e]1.10 mg/kg represents a first priming dose of 1 mg/kg followed by a maintenance dose of 10 mg/kg of Hu5F9-G4 one week after, similarly for 1.20 mg/kg.

Disclosed herein are methods of treating a subject having a cancer with an anti-CD47 agent such as Hu5F9-G4, alone, or in combination with one or more additional agents such as an anti-CD20 agent.

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limit of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As used herein, the term "anti-CD47 agent" refers to any agent that reduces the binding of CD47 (e.g., on a target cell) to SIRPα (e.g., on a phagocytic cell). Non-limiting examples of suitable anti-CD47 reagents include SIRPα reagents, including without limitation high affinity SIRPα polypeptides, anti-SIRPα antibodies, soluble CD47 polypeptides, and anti-CD47 antibodies or antibody fragments. In some embodiments, a suitable anti-CD47 agent (e.g. an anti-CD47 antibody, a SIRPα reagent, etc.) specifically binds CD47 to reduce the binding of CD47 to SIRPα. In some embodiments, a suitable anti-CD47 agent (e.g., an anti-SIRPα antibody, a soluble CD47 polypeptide, etc.) specifically binds SIRPα to reduce the binding of CD47 to SIRPα. A suitable anti-CD47 agent that binds SIRPα does not activate SIRPα (e.g., in the SIRPα-expressing phagocytic cell). The efficacy of a suitable anti-CD47 agent can be assessed by assaying the agent (further described below). In an exemplary assay, target cells are incubated in the presence or absence of the candidate agent. An agent for use in the methods of the invention will up-regulate phagocytosis by at least 10% (e.g., at least 20%, at least 30%, at least 40%, at least 50%, at least 60%, at least 70%, at least 80%, at least 90%, at least 100%, at least 120%, at least 140%, at least 160%, at least 180%, or at least 200%) compared to phagocytosis in the absence of the agent. Similarly, an in vitro assay for levels of tyrosine phosphorylation of SIRPα will show a decrease in phosphorylation by at least 5% (e.g., at least 10%, at least 15%, at least 20%, at least 30%, at least 40%, at least 50%, at least 60%, at least 70%, at least 80%, at least 90%, or 100%) compared to phosphorylation observed in absence of the candidate agent.

In some embodiments, the anti-CD47 agent does not activate CD47 upon binding.

When CD47 is activated, a process akin to apoptosis (i.e., programmed cell death) may occur (Manna and Frazier, Cancer Research, 64, 1026-1036, Feb. 1 2004). Thus, in some embodiments, the anti-CD47 agent does not directly induce cell death of a CD47-expressing cell.

Some pathogens (e.g., pox viruses, Myxoma virus, Deerpox virus, swinepox virus, goatpox virus, sheeppox virus, etc.) express a CD47-analog (i.e., a CD47 mimic) (e.g., the M128L protein) that acts as a virulence factor to enable infection (Cameron et al., Virology. 2005 Jun. 20; 337(1): 55-67), and some pathogens induce the expression of endogenous CD47 in the host cell. Cells infected with a pathogen that expresses a CD47-analog may therefore express the pathogen-provided CD47 analog either exclusively or in combination with endogenous CD47. This mechanism allows the pathogen to increase CD47 expression (via expression of the CD47 analog) in the infected cell with or without increasing the level of endogenous CD47. In some embodiments, an anti-CD47 agent (e.g., anti-CD47 antibody, a SIRPα reagent, a SIRPα antibody, a soluble CD47 polypeptide, etc.) can reduce the binding of a CD47 analog (i.e., a CD47 mimic) to SIRPα. In some cases, a suitable anti-CD47 agent (e.g., a SIRPα reagent, an anti-CD47 antibody, etc.) can bind a CD47 analog (i.e., a CD47 mimic) to reduce the binding of the CD47 analog to SIRPα. In some cases, a suitable anti-CD47 agent (e.g., an anti-SIRPα antibody, a soluble CD47 polypeptide, etc.) can bind to SIRPα. A suitable anti-CD47 agent that binds SIRPα does not activate SIRPα (e.g., in the SIRPα-expressing phagocytic cell). An anti-CD47 agent can be used in any of the methods provided herein when the pathogen is a pathogen that provides a CD47 analog. In other words the term "CD47," as used herein, encompasses CD47 as well as CD47 analogs (i.e., CD47 mimics).

A SIRPα reagent comprises the portion of SIRPα that is sufficient to bind CD47 at a recognizable affinity, which normally lies between the signal sequence and the transmembrane domain, or a fragment thereof that retains the binding activity. A suitable SIRPα reagent reduces (e.g., blocks, prevents, etc.) the interaction between the native proteins SIRPα and CD47. The SIRPα reagent will usually comprise at least the d1 domain of SIRPα. In some embodiments, a SIRPα reagent is a fusion protein, e.g., fused in frame with a second polypeptide. In some embodiments, the second polypeptide is capable of increasing the size of the fusion protein, e.g., so that the fusion protein will not be cleared from the circulation rapidly. In some embodiments, the second polypeptide is part or whole of an immunoglobulin Fc region. The Fc region aids in phagocytosis by providing an "eat me" signal, which enhances the block of the "don't eat me" signal provided by the high affinity SIRPα reagent. In other embodiments, the second polypeptide is any suitable polypeptide that is substantially similar to Fc, e.g., providing increased size, multimerization domains, and/or additional binding or interaction with Ig molecules.

In some embodiments, a subject anti-CD47 agent is a "high affinity SIRPα reagent", which includes SIRPα-derived polypeptides and analogs thereof. High affinity SIRPα reagents are described in international application PCT/US13/21937, which is hereby specifically incorporated by reference. High affinity SIRPα reagents are variants of the native SIRPα protein. In some embodiments, a high affinity SIRPα reagent is soluble, where the polypeptide lacks the SIRPα transmembrane domain and comprises at least one amino acid change relative to the wild-type SIRPα sequence, and wherein the amino acid change increases the affinity of the SIRPα polypeptide binding to CD47, for example by decreasing the off-rate by at least 10-fold, at least 20-fold, at least 50-fold, at least 100-fold, at least 500-fold, or more.

A high affinity SIRPα reagent comprises the portion of SIRPα that is sufficient to bind CD47 at a recognizable affinity, e.g., high affinity, which normally lies between the signal sequence and the transmembrane domain, or a fragment thereof that retains the binding activity. The high affinity SIRPα reagent will usually comprise at least the d1 domain of SIRPα with modified amino acid residues to increase affinity. In some embodiments, a SIRPα variant of the present invention is a fusion protein, e.g., fused in frame with a second polypeptide. In some embodiments, the second polypeptide is capable of increasing the size of the fusion protein, e.g., so that the fusion protein will not be cleared from the circulation rapidly. In some embodiments, the second polypeptide is part or whole of an immunoglobulin Fc region. The Fc region aids in phagocytosis by providing an "eat me" signal, which enhances the block of the "don't eat me" signal provided by the high affinity SIRPα reagent. In other embodiments, the second polypeptide is any suitable polypeptide that is substantially similar to Fc, e.g., providing increased size, multimerization domains, and/or additional binding or interaction with Ig molecules. The amino acid changes that provide for increased affinity are localized in the d1 domain, and thus high affinity SIRPα reagents comprise a d1 domain of human SIRPα, with at least one amino acid change relative to the wild-type sequence within the d1 domain Such a high affinity SIRPα reagent optionally comprises additional amino acid sequences, for example antibody Fc sequences; portions of the wild-type human.

SIRPα protein other than the d1 domain, including without limitation residues 150 to 374 of the native protein or fragments thereof, usually fragments contiguous with the d1 domain; and the like. High affinity SIRPα reagents may be monomeric or multimeric, i.e. dimer, trimer, tetramer, etc.

In some embodiments, a subject anti-CD47 agent is an antibody that specifically binds SIRPα (i.e., an anti-SIRPα antibody) and reduces the interaction between CD47 on one cell (e.g., an infected cell) and SIRPα on another cell (e.g., a phagocytic cell). Suitable anti-SIRPα antibodies can bind SIRPα without activating or stimulating signaling through SIRPα because activation of SIRPα would inhibit phagocytosis. Instead, suitable anti-SIRPα antibodies facilitate the preferential phagocytosis of inflicted cells over normal cells. Those cells that express higher levels of CD47 (e.g., infected cells) relative to other cells (non-infected cells) will be preferentially phagocytosed. Thus, a suitable anti-SIRPα antibody specifically binds SIRPα (without activating/stimulating enough of a signaling response to inhibit phagocytosis) and blocks an interaction between SIRPα and CD47. Suitable anti-SIRPα antibodies include fully human, humanized or chimeric versions of such antibodies. Humanized antibodies are especially useful for in vivo applications in humans due to their low antigenicity. Similarly caninized, felinized, etc. antibodies are especially useful for applications in dogs, cats, and other species respectively. Antibodies of interest include humanized antibodies, or caninized, felinized, equinized, bovinized, porcinized, etc., antibodies, and variants thereof.

Soluble CD47 polypeptides. In some embodiments, a subject anti-CD47 agent is a soluble CD47 polypeptide that specifically binds SIRPα and reduces the interaction between each.

As used herein, an "anti-CD47 antibody" refers to any antibody that reduces the binding of CD47 (e.g., on a target cell) to a CD47 ligand such as SIRPα (e.g., on a phagocytic cell). Non-limiting examples are described in more detail below and include but are not limited to Hu5F9-G4. In some embodiments, a subject anti-CD47 agent is an antibody that specifically binds CD47 (i.e., an anti-CD47 antibody) and reduces the interaction between CD47 on one cell (e.g., an infected cell) and SIRPα on another cell (e.g., a phagocytic cell). In some embodiments, a suitable anti-CD47 antibody does not activate CD47 upon binding. Non-limiting examples of suitable antibodies include clones B6H12, 5F9, 8B6, and C3 (for example as described in International Patent Publication WO 2011/143624, herein specifically incorporated by reference). Suitable anti-CD47 antibodies include fully human, humanized, or chimeric versions of antibodies. Humanized antibodies (e.g., hu5F9-G4) are especially useful for in vivo applications in humans due to their low antigenicity. Similarly caninized, felinized, etc. antibodies are especially useful for applications in dogs, cats, and other species respectively. Antibodies of interest include humanized antibodies, or caninized, felinized, equinized, bovinized, porcinized, etc., antibodies, and variants thereof.

As used herein, "antibody" includes reference to an immunoglobulin-based molecule immunologically reactive with a particular antigen (e.g., CD47), and includes both polyclonal and monoclonal antibodies. The term also includes genetically engineered forms such as chimeric antibodies (e.g., humanized murine antibodies) and heteroconjugate antibodies. The term "antibody" also includes antigen binding forms of antibodies, including fragments with antigen-binding capability (e.g., Fab', F(ab')$_2$, Fab, Fv and rIgG. The term also refers to recombinant single chain Fv fragments (scFv). The term antibody also includes bivalent or bispecific molecules, diabodies, triabodies, and tetrabodies. Additional description of the term antibody is found below.

A "patient" for the purposes of the present invention includes both humans and other animals, particularly mammals, including pet and laboratory animals, e.g. mice, rats, rabbits, etc. Thus the methods are applicable to both human therapy and veterinary applications. In one embodiment the patient is a mammal, preferably a primate. In other embodiments the patient is human.

The terms "subject," "individual," and "patient" are used interchangeably herein to refer to a mammal being assessed for treatment and/or being treated. In an embodiment, the mammal is a human. The terms "subject," "individual," and "patient" encompass, without limitation, individuals having cancer. Subjects may be human, but also include other mammals, particularly those mammals useful as laboratory models for human disease, e.g. mouse, rat, etc.

The term "sample" with respect to a patient encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents; washed; or enrichment for certain cell populations, such as cancer cells. The definition also includes sample that have been enriched for particular types of molecules, e.g., nucleic acids, polypeptides, etc. The term "biological sample" encompasses a clinical sample, and also includes tissue obtained by surgical resection, tissue obtained by biopsy, cells in culture, cell supernatants, cell lysates, tissue samples, organs, bone marrow, blood, plasma, serum, and the like. A "biological sample" includes a sample obtained from a patient's cancer cell, e.g., a sample comprising polynucleotides and/or polypeptides that is obtained from a patient's cancer cell (e.g., a cell lysate or other cell extract comprising polynucleotides and/or polypeptides); and a sample comprising cancer cells from a patient. A biological sample comprising a cancer cell from a patient can also include non-cancerous cells.

The term "diagnosis" is used herein to refer to the identification of a molecular or pathological state, disease or condition, such as the identification of a molecular subtype of breast cancer, prostate cancer, or other type of cancer.

The term "prognosis" is used herein to refer to the prediction of the likelihood of cancer-attributable death or progression, including recurrence, metastatic spread, and drug resistance, of a neoplastic disease, such as lymphoma. The term "prediction" is used herein to refer to the act of foretelling or estimating, based on observation, experience, or scientific reasoning. In one example, a physician may predict the likelihood that a patient will survive, following surgical removal of a primary tumor and/or chemotherapy for a certain period of time without cancer recurrence.

As used herein, the terms "treatment," "treating," and the like, refer to administering an agent, or carrying out a procedure, for the purposes of obtaining an effect. The effect may be may be therapeutic in terms of effecting a partial or complete cure for a disease and/or symptoms of the disease. "Treatment," as used herein, may include treatment of a tumor in a mammal, particularly in a human, and includes, without limitation: inhibiting the disease, i.e., arresting its development; and relieving the disease, i.e., causing regression of the disease.

Treating may refer to any indicia of success in the treatment or amelioration of an cancer, including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms can be based on objective or subjective parameters; including the results of an examination by a physician. The term "therapeutic effect" refers to the reduction, elimination, or prevention of the disease, symptoms of the disease, or side effects of the disease in the subject.

"In combination with", "combination therapy" and "combination products" refer, in certain embodiments, to the concurrent administration to a patient of the agents described herein. When administered in combination, each component can be administered at the same time or sequentially in any order at different points in time. Thus, each component can be administered separately but sufficiently closely in time so as to provide the desired therapeutic effect.

"Concomitant administration" of active agents in the methods disclosed herein means administration with the reagents at such time that the agents will have a therapeutic effect at the same time. Such concomitant administration may involve concurrent (i.e. at the same time), prior, or subsequent administration of the agents.

As used herein, the term "correlates," or "correlates with," and like terms, refers to a statistical association between instances of two events, where events include numbers, data sets, and the like. For example, when the events involve numbers, a positive correlation (also referred to herein as a "direct correlation") means that as one increases, the other increases as well. A negative correlation (also referred to herein as an "inverse correlation") means that as one increases, the other decreases.

"Dosage unit" or "dose" refers to physically discrete units suited as unitary dosages for the particular individual to be treated. Each unit can contain a predetermined quantity of active compound(s) calculated to produce the desired therapeutic effect(s) in association with a pharmaceutical carrier. The specification for the dosage unit forms can be dictated by (a) the unique characteristics of the active compound(s) and the particular therapeutic effect(s) to be achieved, and (b) the limitations inherent in the art of compounding such active compound(s).

A "therapeutically effective amount" means the amount that, when administered to a subject for treating a disease, is sufficient to effect treatment for that disease.

Receptor occupancy (RO) assay measures the level of CD47 occupancy by CD47 binding agents, e.g., anti-CD47 antibody (Ab). The purpose of measuring the level of CD47 RO is to determine the relationship between the dose of a CD47 binding agent, the CD47 receptor saturation, and pharmacologic effect. The percent of receptor occupancy over time may provide useful information regarding the amount of drug or duration of exposure needed to produce the desired pharmacological effect. This assay can be used to determine the overall RO in the body by measuring the CD47 RO on surrogate cells, e.g. on CD45 negative (−) red blood cells (RBCs) and CD45 positive (+) white blood cells (WBCs), or other cell populations, e.g. bone marrow or tissue cells obtained through tissue biopsies. The RO assay can also be used to determine CD47 RO on target cells, e.g. RBC, leukemia cells or solid tumor cells, for CD47 binding and or blocking therapies.

Of interest is the use of this assay to determine the threshold of CD47 receptor occupancy that is correlated with the desired pharmacological effect. This threshold can be determined by assays performed ex vivo (in vitro) or by analysis of samples during in vivo dosing/treatment.

In one embodiment of the assay, a CD47 binding standard curve on a cell of interest cells is made by using fluorochrome-conjugated antibody at various concentrations. Receptor occupancy is measured by incubating the target cells with unlabeled antibody under different concentrations, and then the cells were either assayed in in vitro phagocytosis or incubated with a saturating concentration of labeled antibody based on the standard curve and analyzed for binding by flow cytometry. Receptor occupancy was calculated as follows:

$$\% \ RO=100-((MFI_{test}-MFI_{unstained})/(MFI_{saturated\ STD}-MFI_{unstained}))\times 100$$

In other embodiments the assay is performed by infusing a patient with a defined dose of antibody, obtaining a tissue sample, e.g. a blood sample, from the patient, usually before and after infusion of the antibody. The tissue sample is incubated with a saturating concentration of labeled antibody, and analyzed by flow cytometry. The analysis may be gated, for example, on red blood cells, white blood cells, cancer cells, etc.

It has been found that a priming dose that achieves at least about 80% saturation of CD47 on RBCs is sufficient to induce compensation for anemia and reduce degree of anemia on subsequent doses. In humans, the priming dose has been found to be as discussed above, i.e. from about 0.5 mg/kg to about 5 mg/kg, e.g., 1 mg/kg. In some embodiments, a receptor occupancy assay is performed with a candidate CD47 bind agent to determine the level of priming dose that provides for at least about 50% saturation on RBC, at least about 60% saturation, at least about 70% saturation, at least about 80% saturation, at least about 90% saturation, at least about 95% saturation, at least about 99% saturation, or more.

In some embodiments, a receptor occupancy assay is performed to determine the appropriate priming dose for a candidate anti-CD47 agent, e.g. an antibody that binds to CD47, a SIRPc polypeptide, etc.

Antibodies

The methods described herein include administration of an antibody or antibodies, i.e., administration of an anti CD47 antibody and, in some embodiments, administration of an additional antibody. As described above, the term "antibody" includes reference to an immunoglobulin molecule immunologically reactive with a particular antigen, and includes both polyclonal and monoclonal antibodies. The term also includes genetically engineered forms such as chimeric antibodies (e.g., humanized murine antibodies) and heteroconjugate antibodies. The term "antibody" also includes antigen binding forms of antibodies, including fragments with antigen-binding capability (e.g., Fab', F(ab')$_2$, Fab, Fv and rIgG. The term also refers to recombinant single chain Fv fragments (scFv). The term antibody also includes bivalent or bispecific molecules, diabodies, triabodies, and tetrabodies.

Selection of antibodies may be based on a variety of criteria, including selectivity, affinity, cytotoxicity, etc. The phrase "specifically (or selectively) binds" to an antibody or "specifically (or selectively) immunoreactive with," when referring to a protein or peptide, refers to a binding reaction that is determinative of the presence of the protein, in a heterogeneous population of proteins and other biologics. Thus, under designated immunoassay conditions, the specified antibodies bind to a particular protein sequences at least two times the background and more typically more than 10 to 100 times background. In general, antibodies of the present invention bind antigens on the surface of target cells in the presence of effector cells (such as natural killer cells or macrophages). Fc receptors on effector cells recognize bound antibodies.

An antibody immunologically reactive with a particular antigen can be generated by recombinant methods such as selection of libraries of recombinant antibodies in phage or similar vectors, or by immunizing an animal with the antigen or with DNA encoding the antigen. Methods of preparing polyclonal antibodies are known to the skilled artisan. The antibodies may, alternatively, be monoclonal antibodies. Monoclonal antibodies may be prepared using hybridoma methods. In a hybridoma method, an appropriate host animal is typically immunized with an immunizing agent to elicit lymphocytes that produce or are capable of producing antibodies that will specifically bind to the immunizing agent. Alternatively, the lymphocytes may be immunized in vitro. The lymphocytes are then fused with an immortalized cell line using a suitable fusing agent, such as polyethylene glycol, to form a hybridoma cell.

Human antibodies can be produced using various techniques known in the art, including phage display libraries. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire.

Antibodies also exist as a number of well-characterized fragments produced by digestion with various peptidases. Thus pepsin digests an antibody below the disulfide linkages in the hinge region to produce F(ab)'$_2$, a dimer of Fab which itself is a light chain joined to $V_H$-$C_{H1}$ by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region. While various antibody fragments are defined in terms of the digestion of an intact antibody, one of skill will appreciate that such fragments may be synthesized de novo either chemically or by using recombinant DNA methodology.

Thus, the term antibody, as used herein, also includes antibody fragments either produced by the modification of whole antibodies, or those synthesized de novo using recombinant DNA methodologies (e.g., single chain Fv) or those identified using phage display libraries.

A "humanized antibody" is an immunoglobulin molecule which contains minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, a humanized antibody will comprise substantially all of at least one, and typically two, variable domains, in which all or substantially all of the CDR regions correspond to those of a non-human immunoglobulin and all or substantially all of the framework (FR) regions are those of a human immunoglobulin consensus sequence. The humanized antibody optimally also will comprise at least a portion of an immunoglobulin constant region (Fc), typically that of a human immunoglobulin.

Antibodies of interest may be tested for their ability to induce ADCC (antibody-dependent cellular cytotoxicity) or ADCP (antibody dependent cellular phagocytosis). Antibody-associated ADCC activity can be monitored and quantified through detection of either the release of label or lactate dehydrogenase from the lysed cells, or detection of reduced target cell viability (e.g. Annexin assay). Assays for apoptosis may be performed by terminal deoxynucleotidyl transferase-mediated digoxigenin-11-dUTP nick end labeling (TUNEL) assay (Lazebnik et al., Nature: 371, 346 (1994). Cytotoxicity may also be detected directly by detection kits known in the art, such as Cytotoxicity Detection Kit from Roche Applied Science (Indianapolis, Ind.).

Anti-CD47 Agents

The methods described herein include administration of an anti-CD47 antibody.

CD47 is a broadly expressed transmembrane glycoprotein with a single Ig-like domain and five membrane spanning regions, which functions as a cellular ligand for SIRPα with binding mediated through the NH2-terminal V-like domain of SIRPα. SIRPα is expressed primarily on myeloid cells, including macrophages, granulocytes, myeloid dendritic cells (DCs), mast cells, and their precursors, including hematopoietic stem cells. Structural determinants on SIRPα that mediate CD47 binding are discussed by Lee et al. (2007) J. Immunol. 179:7741-7750; Hatherley et al. (2008) Mol Cell. 31(2):266-77; Hatherley et al. (2007) J. B. C. 282:14567-75; and the role of SIRPα cis dimerization in CD47 binding is discussed by Lee et al. (2010) J. B. C. 285:37953-63. In keeping with the role of CD47 to inhibit phagocytosis of normal cells, there is evidence that it is transiently upregulated on hematopoietic stem cells (HSCs) and progenitors just prior to and during their migratory phase, and that the level of CD47 on these cells determines the probability that they are engulfed in vivo.

The term "anti-CD47 agent" or "agent that provides for CD47 blockade" refers to any agent that reduces the binding of CD47 (e.g., on a target cell) to a CD47 ligand such as SIRPα (e.g., on a phagocytic cell). Non-limiting examples of suitable anti-CD47 reagents include SIRPα reagents, including without limitation high affinity SIRPα polypeptides, anti-SIRPα antibodies, soluble CD47 polypeptides, and anti-CD47 antibodies or antibody fragments. In some embodiments, a suitable anti-CD47 agent (e.g. an anti-CD47 antibody, a SIRPα reagent, etc.) specifically binds CD47 to reduce the binding of CD47 to SIRPα.

An anti-CD47 agent can include a SIRPα agent that includes SIRPα or a portion thereof. For example, an anti-CD47 agent can include a SIRPα-based Fc fusion. See, e.g., Kipp Weiskopf, et al. Science 341, 88 (2013), herein incorporated by reference.

An anti-CD47 agent can include a SIRPα agent disclosed in WO2014094122, herein incorporated by reference, in its entirety, for all purposes. For example, a SIRPα agent can include the sequence of SEQ ID NO: 3, 25, or 26 as disclosed in WO2014094122; each of which is herein incorporated by reference.

An anti-CD47 agent can include a SIRPα agent disclosed in WO2017177333, herein incorporated by reference, in its entirety, for all purposes. For example, a SIRPα agent can include the sequence of SEQ ID NO: 3 or 8 as disclosed in WO2017177333; each of which is herein incorporated by reference.

An anti-CD47 agent can include a SIRPα agent disclosed in WO2016023040, herein incorporated by reference, in its entirety, for all purposes. For example, a SIRPα agent can include the sequence of SEQ ID NO: 78-85, 98-104, 107-113, 116-122, 135-137, or 152-159 as disclosed in WO2016023040; each of which is herein incorporated by reference.

An anti-CD47 agent can include a SIRPα agent disclosed in WO2017027422, herein incorporated by reference, in its entirety, for all purposes. For example, a SIRPα agent can include the sequence of SEQ ID NO: 3-34 as disclosed in WO2017027422; each of which is herein incorporated by reference.

In some embodiments, the subject anti-CD47 antibody specifically binds CD47 and reduces the interaction between CD47 on one cell (e.g., an infected cell) and SIRPα on another cell (e.g., a phagocytic cell). In some embodiments, a suitable anti-CD47 antibody does not activate CD47 upon binding. Some anti-CD47 antibodies do not reduce the binding of CD47 to SIRPα and such an antibody can be referred to as a "non-blocking anti-CD47 antibody." A suitable anti-CD47 antibody that is an "anti-CD47 agent" can be referred to as a "CD47-blocking antibody". Non-limiting examples of suitable antibodies include clones B6H12, 5F9, 8B6, and C3 (for example as described in International Patent Publication WO 2011/143624, herein specifically incorporated by reference). Suitable anti-CD47 antibodies include fully human, humanized or chimeric versions of such antibodies. Humanized antibodies (e.g., hu5F9-G4) are especially useful for in vivo applications in humans due to their low antigenicity. Similarly caninized, felinized, etc. antibodies are especially useful for applications in dogs, cats, and other species respectively. Antibodies of interest include humanized antibodies, or caninized, felinized, equinized, bovinized, porcinized, etc., antibodies, and variants thereof.

In some embodiments an anti-CD47 antibody comprises a human IgG Fc region, e.g. an IgG1, IgG2a, IgG2b, IgG3, IgG4 constant region. In one embodiment the IgG Fc region is an IgG4 constant region. The IgG4 hinge may be stabilized by the amino acid substitution S241P (see Angal et al. (1993) Mol. Immunol. 30(1):105-108, herein specifically incorporated by reference).

In some embodiments, the anti-CD47 antibody competes for binding to CD47 with Hu5F9-G4. In some embodiments, the anti-CD47 binds to the same CD47 epitope as Hu5F9-G4.

In some embodiments, an anti-CD47 antibody is administered at a dose of 10-30, 20-30, 10, 20, or 30 mg of antibody per kg of body weight.

In some embodiments, an anti-CD47 antibody results in greater than or equal to 90% receptor saturation, optionally 90-100, 90, 91, 92, 93, 94, 95, 96, 97, 98, 99, or 100% receptor saturation, optionally wherein receptor saturation is measured using flow cytometry or an equivalent assay.

An anti-CD47 antibody can be formulated in a pharmaceutical composition with a pharmaceutically acceptable excipient.

An anti-CD47 antibody can be administered intravenously.

In some embodiments, the methods described herein include administration of the anti-CD47 antibody Hu5F9-G4. In some embodiments, the methods described herein include administration of an anti-CD47 antibody with sequences (light chain, heavy chain and/or CDR) at least 97%, at least 98%, at least 99% or 100% identical to the sequences of Hu5f9-G4. Table 1 contains the sequence of the Hu5f9-G4 antibody heavy and light chains. The CDR regions are shown in bold.

TABLE 1

| SEQ ID NO | Description and Sequence |
|---|---|
| 1 | Hu5f9-G4 Antibody Heavy Chain<br>QVQLVQSGAEVKKPGASVKVSCKASGYTFTNYNMHWVRQAPGQRLE<br>WMGTIYPGNDDTSYNQKFKDRVTITADTSASTAYMELSSLRSEDTA<br>VYYCARGGYRAMDYWGQGTLVTVSSASTKGPSVFPLAPCSRSTSES<br>TAALGCLVKDYFPEPVTVSWNSGALTSGVHTFPAVLQSSGLYSLSS<br>VVTVPSSSLGTKTYTCNVDHKPSNTKVDKRVESKYGPPCPPCPAPE<br>FLGGPSVFLFPPKPKDTLMISRTPEVTCVVVDVSQEDPEVQFNWYV<br>DGVEVHNAKTKPREEQFNSTYRVVSVLTVLHQDWLNGKEYKCKVSN<br>KGLPSSIEKTISKAKGQPREPQVYTLPPSQEEMTKNQVSLTCLVKG<br>FYPSDIAVEWESNGQPENNYKTTPPVLDSDGSFFLYSRLTVDKSRW<br>QEGNVFSCSVMHEALHNHYTQKSLSLSLGK |
| 2 | Hu5f9-G4 Antibody Light chain<br>DIVMTQSPLSLPVTPGEPASISCRSSQSIVYSNGNTYLGWYLQKPG<br>QSPQLLIYKVSNRFSGVPDRFSGSGSGTDFTLKISRVEAEDVGVYY<br>CFQGSHVPYTFGQGTKLEIKRTVAAPSVFIFPPSDEQLKSGTASVV<br>CLLNNFYPREAKVQWKVDNALQSGNSQESVTEQDSKDSTYSLSSTL<br>TLSKADYEKHKVYACEVTHQGLSSPVTKSFNRGEC |

Anti-CD20 Antibodies

The methods described herein include administration of an anti-CD20 antibody. Generally an anti-CD20 antibody is administered in concert with an anti-CD47 antibody.

An anti-CD20 antibody can compete for binding to CD20 with rituximab.

An anti-CD20 antibody can binds to the same CD20 epitope as rituximab.

An anti-CD20 antibody can comprise or consist of rituximab.

An anti-CD20 antibody can compete for binding to CD20 with obinutuzumab, ofatumumab, ocrelizumab, veltuzumab, ocaratuzumab, ibritumomab tiuxetan, tositumomab, iodine 131 tositumumab, a rituximab biosimilar (blitzima, ritemvia, tuxella), or ublituximab.

An anti-CD20 antibody can bind to the same CD20 epitope as obinutuzumab, ofatumumab, ocrelizumab, veltuzumab, ocaratuzumab, ibritumomab tiuxetan, tositumomab, iodine 131 tositumumab, a rituximab biosimilar (blitzima, ritemvia, tuxella), or ublituximab.

An anti-CD20 antibody can comprise or consist of: obinutuzumab, ofatumumab, ocrelizumab, veltuzumab, ocaratuzumab, ibritumomab tiuxetan, tositumomab, iodine 131 tositumumab, a rituximab biosimilar (blitzima, ritemvia, tuxella), or ublituximab.

An anti-CD20 antibody can comprise an Fc such as an active Fc or wild-type Fc. An anti-CD20 antibody can comprise an Fc capable of at least one of ADCC and ADCP. An anti-CD20 antibody comprise an Fc comprising one or more modifications that results in increased ADCC and/or ADCP activity relative to wild-type Fc.

An anti-CD20 antibody can have a higher binding affinity for CD20 relative to rituximab, obinutuzumab, ofatumumab, ocrelizumab, ibritumomab tiuxetan, tositumomab, iodine 131 tositumumab, a rituximab biosimilar (blitzima, ritemvia, tuxella), or ublituximab.

An anti-CD20 antibody can be administered to a subject at a dose of 375 mg/m$^2$ of antibody. An anti-CD20 antibody can be administered once per week, once every two weeks, once per month, once every four weeks, once every eight weeks, or once every two months, optionally at a dose of 375 mg/m$^2$ of antibody at each relevant time point.

An anti-CD47 antibody and an anti-CD20 antibody can be administered concurrently or sequentially, optionally wherein the anti-CD20 antibody is administered prior to the anti-CD47 antibody.

An anti-CD20 antibody can be formulated in a pharmaceutical composition with a pharmaceutically acceptable excipient. An anti-CD20 antibody and an anti-CD47 antibody can be formulated together.

An anti-CD20 antibody can be administered intravenously.

Table 2 contains the sequences of rituximab antibody heavy and light chains.

TABLE 2

| SEQ ID NO | Description and Sequence |
|---|---|
| 3 | >Rituximab heavy chain chimeric<br>QVQLQQPGAELVKPGASVKMSCKASGYTFTSYNMHWVKQTPG<br>RGLEWIGAIYPGNGDTSYNQKFKGKATLTADKSSSTAYMQLS<br>SLTSEDSAVYYCARSTYYGGDWYFNVWGAGTTVTVSAASTKG<br>PSVFPLAPSSKSTSGGTAALGCLVKDYFPEPVTVSWNSGALT<br>SGVHTFPAVLQSSGLYSLSSVVTVPSSSLGTQTYICNVNHKP<br>SNTKVDKKAEPKSCDKTHTCPPCPAPELLGGPSVFLFPPKPK<br>DTLMISRTPEVTCVVVDVSHEDPEVKFNWYVDGVEVHNAKTK<br>PREEQYNSTYRVVSVLTVLHQDWLNGKEYKCKVSNKALPAPI<br>EKTISKAKGQPREPQVYTLPPSRDELTKNQVSLTCLVKGFYP<br>SDIAVEWESNGQPENNYKTTPPVLDSDGSFFLYSKLTVDKSR<br>WQQGNVFSCSVMHEALHNHYTQKSLSLSPGK |
| 4 | >Rituximab light chain chimeric<br>QIVLSQSPAILSASPGEKVTMTCRASSSVSYIHWFQQKPGSS<br>PKPWIYATSNLASGVPVRFSGSGSGTSYSLTISRVEAEDAAT<br>YYCQQWTSNPPTFGGGTKLEIKRTVAAPSVFIFPPSDEQLKS<br>GTASVVCLLNNFYPREAKVQWKVDNALQSGNSQESVTEQDSK<br>DSTYSLSSTLTLSKADYEKHKVYACEVTHQGLSSPVTKSFNR<br>GEC |

Methods of Use

Methods are provided for treating a subject with a therapeutic dose of anti-CD47 agent. For example, a method can include treating a human subject having a CD20+ cancer or reducing the size of the CD20+ cancer in the human subject, comprising: (a) administering an anti-CD47 antibody to the subject at a dose of greater than or equal to 10 mg of antibody per kg of body weight; and (b) administering an anti-CD20 antibody to the subject.

Methods can include a step of administering a primer agent to subject, followed by a step of administering a therapeutically effective dose of an anti-CD47 agent to the subject. In some embodiments, the step of administering a therapeutically effective dose is performed after at least about 3 days (e.g., at least about 4 days, at least about 5 days, at least about 6 days, at least about 7 days, at least about 8 days, at least about 9 days, or at least about 10 days) after beginning the administration of a primer agent. This period of time is, for example, sufficient to provide for enhanced reticulocyte production by the individual.

The administration of a therapeutically effective dose of an anti-CD47 agent can be achieved in a number of different ways. In some cases, two or more therapeutically effective doses are administered after a primer agent is administered. Suitable administration of a therapeutically effective dose can entail administration of a single dose, or can entail administration of doses daily, semi-weekly, weekly, once every two weeks, once a month, annually, etc. In some cases, a therapeutically effective dose is administered as two or more doses of escalating concentration (i.e., increasing doses), where (i) all of the doses are therapeutic doses, or where (ii) a sub-therapeutic dose (or two or more sub-therapeutic doses) is initially given and therapeutic doses are achieved by said escalation. As one non-limiting example to illustrate escalating concentration (i.e., increasing doses), a therapeutically effective dose can be administered weekly, beginning with a sub-therapeutic dose (e.g., a dose of 5 mg/kg), and each subsequent dose can be increased by a particular increment (e.g., by 5 mg/kg), or by variable increments, until a therapeutic dose (e.g., 30 mg/kg) is reached, at which point administration may cease or may continue (e.g., continued therapeutic doses, e.g., doses of 30 mg/kg). As another non-limiting example to illustrate escalating concentration (i.e., increasing doses), a therapeutically effective dose can be administered weekly, beginning with a therapeutic dose (e.g., a dose of 10 mg/kg), and each subsequent dose can be increased by a particular increment (e.g., by 10 mg/kg), or by variable increments, until a therapeutic dose (e.g., 30 mg/kg, 100 mg/kg, etc.) is reached, at which point administration may cease or may continue (e.g., continued therapeutic doses, e.g., doses of 30 mg/kg, 100 mg/kg, etc.). In some embodiments, administration of a therapeutically effective dose can be a continuous infusion and the dose can altered (e.g., escalated) over time.

Dosage and frequency may vary depending on the half-life of the anti-CD47 agent in the patient. It will be understood by one of skill in the art that such guidelines will be adjusted for the molecular weight of the active agent, e.g. in the use of antibody fragments, in the use of antibody conjugates, in the use of SIRPα reagents, in the use of soluble CD47 peptides etc. The dosage may also be varied for localized administration, e.g. intranasal, inhalation, etc., or for systemic administration, e.g. i.m., i.p., i.v., s.c., and the like.

An initial dose of a CD47 binding agent, including but not limited to a priming dose, may lead to hemagglutination for a period of time immediately following infusion. Without being bound by the theory, it is believed that the initial dose of a multivalent CD47 binding agent may cause cross-linking of RBC bound to the agent. In certain embodiments of the invention, a CD47 binding agent is infused to a patient in an initial dose, and optionally in subsequent doses, over a period of time and/or concentration that reduces the possibility of hematologic microenvironments where there is a high local concentration of RBC and the agent.

In some embodiments, an initial dose of a CD47 binding agent is infused over a period of at least about 2 hours, at least about 2.5 hours, at least about 3 hours, at least about 3.5 hours, at least about 4 hours, at least about 4.5 hours, at least about 5 hours, at least about 6 hours or more. In some embodiments an initial dose is infused over a period of time from about 2.5 hours to about 6 hours; for example from about 3 hours to about 4 hours. In some such embodiments, the dose of agent in the infusate is from about 0.05 mg/ml to about 0.5 mg/ml; for example from about 0.1 mg/ml to about 0.25 mg/ml.

In other embodiments, an initial dose of a CD47 binding agent, e.g. a priming dose, is administered by continuous fusion, e.g. as an osmotic pump, delivery patch, etc., where the dose is administered over a period of at least about 6 hours, at least about 12 hours, at least about 24 hours, at least about 2 days, at least about 3 days. Many such systems are known in the art. For example DUROS technology, provides a bi-compartment system separated by a piston. One of the compartments consists of osmotic engine specifically formulated with an excess of solid NaCl, such that it remains present throughout the delivery period and results in a constant osmotic gradient. It also consists of a semi permeable membrane on one end through which water is drawn into the osmotic engine and establishes a large and constant osmotic gradient between the tissue water and the osmotic engine. Other compartment consists of a drug solution with an orifice from which the drug is released due to the osmotic gradient. This helps to provide site specific and systemic drug delivery when implanted in humans. The preferred site of implantation is subcutaneous placement in the inside of the upper arm.

Following administration of the priming agent, and allowing a period of time effective for an increase in reticulocyte production, a therapeutic dose of an anti-CD47 agent is administered. The therapeutic dose can be administered in number of different ways. In some embodiments, two or more therapeutically effective doses are administered after a primer agent is administered, e.g. in a weekly dosing schedule. In some embodiments a therapeutically effective dose of an anti-CD47 agent is administered as two or more doses of escalating concentration, in others the doses are equivalent. There is reduced hemagglutination after the priming dose.

Additional agents can enhance the efficacy of anti-CD47 agents. The anti-CD47 antibody can be administered in combination or prior to the additional agent.

A combination of an anti-CD47 antibody with an additional agent described herein is given to patients with tumors subtypes that are responsive to these therapies. These tumors may be defined by a higher frequency of mutations, resulting in more tumor antigens, therefore being more immunogenic, as described herein. In some embodiments patients treated with combination therapy are responsive to treatment with an immune activator or checkpoint inhibitor; however this represents a subset of approximately 25% of patients within a specific potentially responsive tumor subtype. In some embodiments, the individuals may be platinum therapy sensitive or resistant.

In some embodiments, the subject methods include a step of administering a primer agent to subject, followed by a step of administering a therapeutically effective dose of an anti-CD47 antibody and an additional agent to the subject.

In some embodiments, the step of administering a therapeutically effective dose is performed after at least about 3 days (e.g., at least about 4 days, at least about 5 days, at least about 6 days, at least about 7 days, at least about 8 days, at least about 9 days, or at least about 10 days) after beginning the administration of a primer agent. This period of time is, for example, sufficient to provide for enhanced reticulocyte production by the individual.

The administration of a therapeutically effective dose of an anti-CD47 antibody and/or an additional agent can be achieved in a number of different ways. In some cases, two or more therapeutically effective doses are administered after a primer agent is administered. Suitable administration of a therapeutically effective dose can entail administration of a single dose, or can entail administration of doses daily, semi-weekly, weekly, once every two weeks, once a month, annually, etc. In some cases, a therapeutically effective dose is administered as two or more doses of escalating concentration (i.e., increasing doses), where (i) all of the doses are therapeutic doses, or where (ii) a sub-therapeutic dose (or two or more sub-therapeutic doses) is initially given and therapeutic doses are achieved by said escalation. As one non-limiting example to illustrate escalating concentration (i.e., increasing doses), a therapeutically effective dose can be administered weekly, beginning with a sub-therapeutic dose (e.g., a dose of 5 mg/kg), and each subsequent dose can be increased by a particular increment (e.g., by 5 mg/kg), or by variable increments, until a therapeutic dose (e.g., 30 mg/kg) is reached, at which point administration may cease or may continue (e.g., continued therapeutic doses, e.g., doses of 30 mg/kg). As another non-limiting example to illustrate escalating concentration (i.e., increasing doses), a therapeutically effective dose can be administered weekly, beginning with a therapeutic dose (e.g., a dose of 10 mg/kg), and each subsequent dose can be increased by a particular increment (e.g., by 10 mg/kg), or by variable increments, until a therapeutic dose (e.g., 30 mg/kg, 100 mg/kg, etc.) is reached, at which point administration may cease or may continue (e.g., continued therapeutic doses, e.g., doses of 30 mg/kg, 100 mg/kg, etc.). In some embodiments, administration of a therapeutically effective dose can be a continuous infusion and the dose can altered (e.g., escalated) over time.

Dosage and frequency may vary depending on the half-life of the anti-CD47 antibody and/or the additional agent in the patient. It will be understood by one of skill in the art that such guidelines will be adjusted for the molecular weight of the active agent, e.g. in the use of antibody fragments, in the use of antibody conjugates, in the use of SIRPα reagents, in the use of soluble CD47 peptides etc. The dosage may also be varied for localized administration, e.g. intranasal, inhalation, etc., or for systemic administration, e.g. i.m., i.p., i.v., s.c., and the like.

In certain embodiments of the invention, the anti-CD47 antibody is infused to a patient in an initial dose, and optionally in subsequent doses, over a period of time and/or concentration that reduces the possibility of hematologic microenvironments where there is a high local concentration of RBC and the agent.

In some embodiments of the invention, an initial dose of the anti-CD47 antibody is infused over a period of at least about 2 hours, at least about 2.5 hours, at least about 3 hours, at least about 3.5 hours, at least about 4 hours, at least about 4.5 hours, at least about 5 hours, at least about 6 hours or more. In some embodiments an initial dose is infused over a period of time from about 2.5 hours to about 6 hours; for example from about 3 hours to about 4 hours. In some such embodiments, the dose of agent in the infusate is from about 0.05 mg/ml to about 0.5 mg/ml; for example from about 0.1 mg/ml to about 0.25 mg/ml.

Cancer

The terms "cancer," "neoplasm," and "tumor" are used interchangeably herein to refer to cells which exhibit autonomous, unregulated growth, such that they exhibit an aberrant growth phenotype characterized by a significant loss of control over cell proliferation. Cells of interest for detection, analysis, or treatment in the present application include precancerous (e.g., benign), malignant, pre-metastatic, metastatic, and non-metastatic cells. Cancers of virtually every tissue are known. The phrase "cancer burden" refers to the quantum of cancer cells or cancer volume in a subject. Reducing cancer burden accordingly refers to reducing the number of cancer cells or the cancer volume in a subject. The term "cancer cell" as used herein refers to any cell that is a cancer cell or is derived from a cancer cell e.g. clone of a cancer cell. Many types of cancers are known to those of skill in the art, including solid tumors such as carcinomas, sarcomas, glioblastomas, melanomas, lymphomas, myelomas, etc., and circulating cancers such as leukemias.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, pre-malignancy, malignancy, invasion of surrounding or distant tissues or organs, such as lymph nodes, etc.

As used herein, the terms "cancer recurrence" and "tumor recurrence," and grammatical variants thereof, refer to further growth of neoplastic or cancerous cells after diagnosis of cancer. Particularly, recurrence may occur when further cancerous cell growth occurs in the cancerous tissue. "Tumor spread," similarly, occurs when the cells of a tumor disseminate into local or distant tissues and organs; therefore tumor spread encompasses tumor metastasis. "Tumor invasion" occurs when the tumor growth spread out locally to compromise the function of involved tissues by compression, destruction, or prevention of normal organ function.

As used herein, the term "metastasis" refers to the growth of a cancerous tumor in an organ or body part, which is not directly connected to the organ of the original cancerous tumor. Metastasis will be understood to include micrometastasis, which is the presence of an undetectable amount of cancerous cells in an organ or body part which is not directly connected to the organ of the original cancerous tumor. Metastasis can also be defined as several steps of a process, such as the departure of cancer cells from an original tumor site, and migration and/or invasion of cancer cells to other parts of the body.

In some embodiments, the patient has a low mutation burden. In some embodiments, the patient has a high mutation burden. As is known in the art, cancer types can vary in the average or specific degree of mutation, where higher levels of mutation are associated with increased expression of neoantigens. See, for example, Vogelstein et al., (2013), supra. A low mutation burden can be a cancer type with an average per tumor, or specific number for an individual tumor, of up to about 10, up to about 20, up to about 30, up to about 40, up to about 50 non-synonymous mutations per tumor. A high mutation burden can be a cancer type with greater than about 50, greater than about 75, greater than about 100, greater than about 125, greater than about 150 non-synonymous mutations per tumor.

CD20+ Cancer

Provided herein are methods for treating individuals having a CD20+ cancer or reducing the size of such cancer in the subject, comprising administering: a therapeutically effective amount of an anti-CD47 antibody to the subject; and, optionally a therapeutically effective amount of at least one additional agent to the subject such as an anti-CD20 agent.

In some embodiments, a CD20+ cancer is a B cell cancer. B cell cancers can include Non-Hodgkin's lymphoma (NHL).

NHL can include indolent lymphoma. Indolent lymphoma can include follicular lymphoma (FL). Indolent lymphoma can include marginal zone lymphoma.

NHL can include diffuse large B cell lymphoma (DLBCL). NHL can further include DLBCL subtypes such as de novo DLBCL or transformed DLBCL. DLBCL can be from different cells of origin including activated B cell, germinal center B cell, and double hit lymphoma.

A CD20+ cancer can include DLBCL, follicular lymphoma, marginal zone lymphoma, mantle cell lymphoma, chronic lymphocytic leukemia/small lymphocytic leukemia, waldenstrom's macroglobulinemia/lymphoplasmacytic lymphoma, primary mediastinal B-cell lymphoma, Burkitt's lymphoma, B-cell lymphoma unclassified, B-cell acute lymphoblastic leukemia, or post-transplant lymphoproliferative disease (PTLD). A given CD20+ cancer sub-type, such as those disclosed herein, can be classified based on histopathology, flow cytometry, molecular classification, one or more equivalent assays, or a combination thereof.

A CD20+ cancer can include double hit lymphoma (e.g., high grade C cell lymphoma with MYC and BCL2 and/or BCL6 rearrangement). A CD20+ cancer can include a myc-rearranged lymphoma.

Further Combination Therapies

In some embodiments, an antibody provided herein is administered with at least one additional therapeutic agent. Any suitable additional therapeutic agent may be administered with an antibody provided herein.

In some embodiments, the additional therapeutic agent comprises an immunostimulatory agent. In some embodiments, the immunostimulatory agent is an agent that blocks signaling of an inhibitory receptor of an immune cell, or a ligand thereof. In some aspects, the inhibitory receptor or ligand is PD-1 or PD-L1. In some aspects, the agent is selected from an anti-PD-1 antibody (e.g., pembrolizumab or nivolumab), and anti-PD-L1 antibody (e.g., atezolizumab), and combinations thereof. In some aspects, the agent is pembrolizumab. In some aspects, the agent is nivolumab. In some aspects, the agent is atezolizumab.

Table 3 contains the heavy and light chain sequences of atezolizumab.

TABLE 3

Atezolizumab sequences

| SEQ ID NO | Description and Sequence |
|---|---|
| 5 | >Heavy Chain Sequence<br>EVQLVESGGGLVQPGGSLRLSCAASGFTFSDSWIHWVRQAPG<br>KGLEWVAWISPYGGSTYYADSVKGRFTISADTSKNTAYLQMN<br>SLRAEDTAVYYCARRHWPGGFDYWGQGTLVTVSSASTKGPSV<br>FPLAPSSKSTSGGTAALGCLVKDYFPEPVTVSWNSGALTSGV<br>HTFPAVLQSSGLYSLSSVVTVPSSSLGTQTYICNVNHKPSNT<br>KVDKKVEPKSCDKTHTCPPCPAPELLGGPSVFLFPPKPKDTL<br>MISRTPEVTCVVVDVSHEDPEVKFNWYVDGVEVHNAKTKPRE<br>EQYASTYRVVSVLTVLHQDWLNGKEYKCKVSNKALPAPIEKT<br>ISKAKGQPREPQVYTLPPSREEMTKNQVSLTCLVKGFYPSDI<br>AVEWESNGQPENNYKTTPPVLDSDGSFFLYSKLTVDKSRWQQ<br>GNVFSCSVMHEALHNHYTQKSLSLSPGK |
| 6 | >Light Chain Sequence<br>DIQMTQSPSSLSASVGDRVTITCRASQDVSTAVAWYQQKPGK<br>APKLLIYSASFLYSGVPSRFSGSGSGTDFTLTISSLQPEDFA<br>TYYCQQYLYHPATFGQGTKVEIKRTVAAPSVFIFPPSDEQLK<br>SGTASVVCLLNNFYPREAKVQWKVDNALQSGNSQESVTEQDS<br>KDSTYSLSSTLTLSKADYEKHKVYACEVTHQGLSSPVTKSFN<br>RGEC |

In some embodiments, the additional therapeutic agent is an agent that inhibits the interaction between PD-1 and PD-L1. In some aspects, the additional therapeutic agent that inhibits the interaction between PD-1 and PD-L1 is selected from an antibody, a peptidomimetic and a small molecule. In some aspects, the additional therapeutic agent that inhibits the interaction between PD-1 and PD-L1 is selected from pembrolizumab, nivolumab, atezolizumab, avelumab, durvalumab, tislelizumab, cemiplimab, BMS-936559, sulfamonomethoxine 1, sulfamethizole 2, and combinations thereof. In some embodiments, the additional therapeutic agent that inhibits the interaction between PD-1 and PD-L1 is any therapeutic known in the art to have such activity, for example as described in Weinmann et al., Chem Med Chem, 2016, 14:1576 (DOI: 10.1002/cmdc.201500566), incorporated by reference in its entirety. In some embodiments, the agent that inhibits the interaction between PD-1 and PD-L1 is formulated in the same pharmaceutical composition and an antibody provided herein. In some embodiments, the agent that inhibits the interaction between PD-1 and PD-L1 is formulated in a different pharmaceutical composition from an antibody provided herein. In some embodiments, the agent that inhibits the interaction between PD-1 and PD-L1 is administered prior to administration of an antibody provided herein. In some embodiments, the agent that inhibits the interaction between PD-1 and PD-L1 is administered after administration of an antibody provided herein. In some embodiments, the agent that inhibits the interaction between PD-1 and PD-L1 is administered contemporaneously with an antibody provided herein, but the agent and antibody are administered in separate pharmaceutical compositions.

In some embodiments, the additional therapeutic agent comprises a Bcl-2/Bcl-xL inhibitor. The Bcl-2/Bcl-xL inhibitor can include venetoclax, navitoclax, and/or AZD0466, or others. In some embodiments, the Bcl-2/Bcl-xL inhibitor is formulated in the same pharmaceutical composition and an antibody provided herein. In some embodiments, the Bcl-2/Bcl-xL inhibitor is formulated in a different pharmaceutical composition from an antibody provided herein. In some embodiments, the Bcl-2/Bcl-xL inhibitor is administered prior to administration of an antibody provided herein. In some embodiments, the Bcl-2/Bcl-xL inhibitor is administered after administration of an antibody provided herein. In some embodiments, the Bcl-2/Bcl-xL inhibitor is administered contemporaneously with an antibody provided herein, but the Bcl-2/Bcl-xL inhibitor and antibody are administered in separate pharmaceutical compositions.

Subject Status and Selection

A subject with cancer that is administered an anti-CD47 agent and an anti-CD20 agent can have a certain status. The status can be used for selection of the subject. A status can make a given subject more likely to benefit from administration of both agents.

A subject can be relapsed or refractory to at least 1, 2, 3, 4, 5, 6, 7, 8, 9, 10 or greater than 10 prior lines of cancer therapy.

A subject can be refractory to rituximab. A subject can be resistant to rituximab.

Rituximab refractory status can be a failure to respond to, or progression during, any previous rituximab-containing regimen, or progression within 6 months of the last rituximab dose.

Rituximab refractory status can be a failure to respond to, or progression during, last previous rituximab-containing regimen, or progression within 6 months of the last rituximab dose.

In some aspects, a subject has follicular lymphoma (FL) and has received at least two prior systemic therapies. In some aspects, a subject has follicular lymphoma (FL) and relapsed after, or is refractory to, a rituximab-containing regimen.

In some aspects, a subject has relapsed or refractory large-B cell lymphoma after two or more lines of systemic therapy. In some aspects, a subject has de novo or transformed large-B cell lymphoma refractory to frontline therapy, or relapsed or refractory to second line salvage regimens or autologous hematopoietic cell transplantation. In some aspects, a subject has large-B cell lymphoma and relapsed after, or is refractory after two or more lines of systemic therapy including a rituximab-containing regimen.

In some aspects, the expression level of CD47 in lymphoma tissue of a subject can be determined by an assay. CD47 expression can be protein expression by immunohistochemistry, flow cytometry, mass cytometry (CyTOF), or gene expression by RNA sequencing, microarray analysis or other gene expression profiling method.

Examples of assays for CD47 include DNA assays (including whole genome or exome sequencing), microarrays, polymerase chain reaction (PCR), RT-PCR, Southern blots, Northern blots, antibody-binding assays, enzyme-linked immunosorbent assays (ELISAs), flow cytometry, protein assays, Western blots, nephelometry, turbidimetry, chromatography, mass spectrometry, immunoassays, including, by way of example, but not limitation, RIA, immunofluorescence, immunochemiluminescence, immunoelectrochemiluminescence, or competitive immunoassays, and immunoprecipitation. The information from the assay can be quantitative and sent to a computer system of the invention. The information can also be qualitative, such as observing patterns or fluorescence, which can be translated into a quantitative measure by a user or automatically by a reader or computer system. In an embodiment, the subject can also provide information other than assay information to a computer system, such as race, height, weight, age, gender, eye color, hair color, family medical history and any other information that may be useful to a user, such as a clinical factor.

Protein detection assays are assays used to detect the expression level of a given protein from a sample. Protein detection assays are generally known in the art and can include an immunoassay, a protein-binding assay, an antibody-based assay, an antigen-binding protein-based assay, a protein-based array, an enzyme-linked immunosorbent assay (ELISA), flow cytometry, a protein array, a blot, a Western blot, nephelometry, turbidimetry, chromatography, mass spectrometry, enzymatic activity, and an immunoassays selected from RIA, immunofluorescence, immunochemiluminescence, immunoelectrochemiluminescence, immunoelectrophoretic, a competitive immunoassay, and immunoprecipitation.

Protein based analysis, using an antibody as described above that specifically binds to a polypeptide encoded by an altered nucleic acid or an antibody that specifically binds to a polypeptide encoded by a non-altered nucleic acid, or an antibody that specifically binds to a particular splicing variant encoded by a nucleic acid, can be used to identify the presence in a test sample of a particular splicing variant or of a polypeptide encoded by a polymorphic or altered nucleic acid, or the absence in a test sample of a particular splicing variant or of a polypeptide encoded by a non-polymorphic or non-altered nucleic acid. The presence of a polypeptide encoded by a polymorphic or altered nucleic acid, or the absence of a polypeptide encoded by a non-polymorphic or non-altered nucleic acid, is diagnostic for a susceptibility to coronary artery disease.

In one aspect, the level or amount of polypeptide encoded by a nucleic acid in a test sample is compared with the level or amount of the polypeptide encoded by the nucleic acid in a control sample. A level or amount of the polypeptide in the test sample that is higher or lower than the level or amount of the polypeptide in the control sample, such that the difference is statistically significant, is indicative of an alteration in the expression of the polypeptide encoded by the nucleic acid, and is diagnostic. Alternatively, the composition of the polypeptide encoded by a nucleic acid in a test sample is compared with the composition of the polypeptide encoded by the nucleic acid in a control sample (e.g., the presence of different splicing variants). A difference in the composition of the polypeptide in the test sample, as compared with the composition of the polypeptide in the control sample, is diagnostic. In another aspect, both the level or amount and the composition of the polypeptide can be assessed in the test sample and in the control sample. A difference in the amount or level of the polypeptide in the test sample, compared to the control sample; a difference in composition in the test sample, compared to the control sample; or both a difference in the amount or level, and a difference in the composition, is indicative of whether a subject should be treated with an anti-CD47 antibody, either increased or decreased.

In addition, one of skill will also understand that the above described methods can also generally be used to detect markers that do not include a polymorphism. In some aspects the subject from whom a sample is taken for an assay has activated B-cell (ABC) DLBCL. In some aspects the subject from whom a sample is taken for an assay has non-germinal center B cell (GCB) DLBCL. In some aspects, the subject has increased expression of CD47 relative to (normal) control and the anti-CD47 antibody is administered to the subject, optionally the subject has ABC or non-germinal center B cell (GCB) DLBCL. Determination of ABC or GCB status can be performed, e.g., by gene expression profiling.

Dosing

The methods described herein include administration of a therapeutically effective dose of compositions, i.e., a therapeutically effective dose of an anti-CD47 antibody and, optionally, an additional agent.

Compositions are administered to a patient in an amount sufficient to substantially ablate targeted cells, as described above. An amount adequate to accomplish this is defined as a "therapeutically effective dose", which may provide for an improvement in overall survival rates. Single or multiple administrations of the compositions may be administered depending on the dosage and frequency as needed and tolerated by the patient. The particular dose used for a treatment will depend upon the medical condition and history of the mammal, as well as other factors such as age, weight, gender, administration route, efficiency, etc.

Effective doses of the combined agents of the present invention for the treatment of cancer vary depending upon many different factors, including means of administration, target site, physiological state of the patient, whether the patient is human or an animal, other medications administered, and whether treatment is prophylactic or therapeutic. Usually, the patient is a human, but nonhuman mammals may also be treated, e.g. companion animals such as dogs, cats, horses, etc., laboratory mammals such as rabbits, mice, rats, etc., and the like. Treatment dosages can be titrated to optimize safety and efficacy.

A therapeutically effective dose of the anti-CD47 antibody can depend on the specific agent used, but is usually about 20 mg/kg body weight or more (e.g., about 20 mg/kg or more, about 25 mg/kg or more, about 30 mg/kg or more, about 35 mg/kg or more, about 40 mg/kg or more, about 45 mg/kg or more, about 50 mg/kg or more, or about 55 mg/kg or more, or about 60 mg/kg or more, or about 65 mg/kg or more, or about 70 mg/kg or more), or from about 20 mg/kg to about 70 mg/kg (e.g., from about 20 mg/kg to about 67.5 mg/kg, or from about 20 mg/kg to about 60 mg/kg).

In some embodiments, the therapeutically effective dose of the anti-CD47 antibody is 20, 30, 45, 60, or 67.5 mg/kg. In some embodiments, the therapeutically effective dose of the anti-CD47 antibody is 20 to 60 mg/kg. In some embodiments, the therapeutically effective dose of the anti-CD47 antibody is 20 to 67.5 mg/kg.

A dose of an anti-CD47 antibody can be a flat dose. For example, a flat dose can be given irrespective of a particular subject's weight. Alternatively a flat dose can be given based on a particular subject's weight falling within a particular weight range, e.g., a first range of less than or equal to 100 kg; or a second range of greater than 100 kg. A flat dose can be, e.g., 1000-5000, 2000-4000, 2000-3500, 2400-3500, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000 mg, or an interim number of mg thereof.

The dose needed to achieve and/or maintain a particular serum level of the administered composition is proportional to the amount of time between doses and inversely proportional to the number of doses administered. Thus, as the frequency of dosing increases, the needed dose decreases. The optimization of dosing strategies will be readily understood and practiced by one of ordinary skill in the art. An exemplary treatment regime entails administration once every two weeks or once a month or once every 3 to 6 months. Therapeutic entities of the present invention are usually administered on multiple occasions. Intervals between single dosages can be weekly, monthly or yearly. Intervals can also be irregular as indicated by measuring blood levels of the therapeutic entity in the patient. Alternatively, therapeutic entities of the present invention can be administered as a sustained release formulation, in which case less frequent administration is used. Dosage and frequency vary depending on the half-life of the polypeptide in the patient.

A "maintenance dose" is a dose intended to be a therapeutically effective dose. For example, in experiments to determine the therapeutically effective dose, multiple different maintenance doses may be administered to different subjects. As such, some of the maintenance doses may be therapeutically effective doses and others may be sub-therapeutic doses.

In prophylactic applications, a relatively low dosage may be administered at relatively infrequent intervals over a long period of time. Some patients continue to receive treatment for the rest of their lives. In other therapeutic applications, a relatively high dosage at relatively short intervals is sometimes used until progression of the disease is reduced or terminated, and preferably until the patient shows partial or complete amelioration of symptoms of disease. Thereafter, the patent can be administered a prophylactic regime.

In still other embodiments, methods of the present invention include treating, reducing or preventing tumor growth, tumor metastasis or tumor invasion of cancers including carcinomas, hematologic cancers, melanomas, sarcomas, gliomas, etc. For prophylactic applications, pharmaceutical compositions or medicaments are administered to a patient susceptible to, or otherwise at risk of disease in an amount sufficient to eliminate or reduce the risk, lessen the severity, or delay the outset of the disease, including biochemical, histologic and/or behavioral symptoms of the disease, its complications and intermediate pathological phenotypes presenting during development of the disease.

Toxicity of the combined agents described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the proteins described herein lies preferably within a range of circulating concentrations that include the effective dose with little or no toxicity. The dosage can vary within this range depending upon the dosage form employed and the route of administration utilized. The exact formulation, route of administration and dosage can be chosen by the individual physician in view of the patient's condition.

Primer Agents and Priming Dose

In some embodiments of the methods described herein, a primer agent is administered prior to administering a therapeutically effective dose of an anti-CD47 antibody to the individual. Suitable primer agents include an erythropoiesis-stimulating agent (ESA), and/or a priming dose of an anti-CD47 antibody. Following administration of the priming agent, and allowing a period of time effective for an increase in reticulocyte production, a therapeutic dose of an anti-CD47 antibody is administered. Administration may be made in accordance with the methods described in copending patent application U.S. Ser. No. 14/769,069, herein specifically incorporated by reference.

In some embodiments, administration of a combination of agents of the invention is combined with an effective dose of an agent that increases patient hematocrit, for example erythropoietin stimulating agents (ESA). Such agents are known and used in the art, including, for example, Aranesp→ (darbepoetin alfa), Epogen→NF/Procrit→NF (epoetin alfa), Omontys→(peginesatide), Procrit→, etc.

The term "priming dose" or as used herein refers to a dose of an anti-CD47 agent that primes a subject for administration of a therapeutically effective dose of anti-CD47 agent such that the therapeutically effective dose does not result in a severe loss of RBCs (reduced hematocrit or reduced hemoglobin). The specific appropriate priming dose of an anti-CD47 agent can vary depending on the nature of the agent used and on numerous subject-specific factors (e.g., age, weight, etc.). Examples of suitable priming doses of an anti-CD47 agent include from about 0.5 mg/kg to about 5 mg/kg, from about 0.5 mg/kg to about 4 mg/kg, from about 0.5 mg/kg to about 3 mg/kg, from about 1 mg/kg to about 5 mg/kg, from about 1 mg/kg to about 4 mg/kg, from about 1 mg/kg to about 3 mg/kg, about 1 mg/kg, about 2 mg/kg, about 3 mg/kg, about 4 mg/kg, about 5 mg/kg. In some embodiments, the priming does is preferably 1 mg/kg.

In some embodiments of the methods described herein, the anti-CD47 antibody is administered to the subject as a priming dose ranging from about 0.5 to about 5 mg/kg of antibody, optionally 1 mg/kg of antibody. In some embodiments, the anti-CD47 antibody is administered to the subject as a dose ranging from about 20 to about 67.5 mg/kg of antibody, optionally 20 mg/kg of antibody, 30 mg/kg of antibody, 45 mg/kg of antibody, 60 mg/kg of antibody, or 67.5 mg/kg of antibody.

A priming dose of an anti-CD47 antibody can be a flat priming dose. For example, a flat priming dose can be given irrespective of a particular subject's weight. Alternatively a flat priming dose can be given based on a particular subject's weight falling within a particular weight range, e.g., a first range of less than or equal to 100 kg; or a second range of greater than 100 kg. A flat priming dose can be, e.g., 10-200, 50-100, 70-90, 75-85, 10, 20, 30, 40, 50, 60, 70, 80, 90, 100, 110, 120, 130, 140, 150, 160, 170, 180, 190, or 200 mg, or an interim number of mg thereof.

In some embodiments of the invention, a primer agent is administered prior to administering a therapeutically effective dose of an anti-CD47 agent to the individual. Suitable primer agents include an erythropoiesis-stimulating agent (ESA), and/or a priming dose of an anti-CD47 agent. Following administration of the priming agent, and allowing a period of time effective for an increase in reticulocyte production, a therapeutic dose of an anti-CD47 agent is administered. The therapeutic dose can be administered in number of different ways. In some embodiments, two or more therapeutically effective doses are administered after a primer agent is administered. In some embodiments a therapeutically effective dose of an anti-CD47 agent is administered as two or more doses of escalating concentration, in others the doses are equivalent.

In some embodiments of the invention, an effective priming dose of Hu-5F9G4 is provided, where the effective priming dose for a human is around about 1 mg/kg, e.g. from at least about 0.5 mg/kg up to not more than about 5 mg/kg; from at least about 0.75 mg/kg up to not more than about 1.25 mg/kg; from at least about 0.95 mg/kg up to not more than about 1.05 mg/kg; and may be around about 1 mg/kg.

In some embodiments of the invention, an initial dose of a CD47 binding agent is infused over a period of at least about 2 hours, at least about 2.5 hours, at least about 3 hours, at least about 3.5 hours, at least about 4 hours, at least about 4.5 hours, at least about 5 hours, at least about 6 hours or more. In some embodiments an initial dose is infused over a period of time from about 2.5 hours to about 6 hours; for example from about 3 hours to about 4 hours. In some such embodiments, the dose of agent in the infusate is from about 0.05 mg/ml to about 0.5 mg/ml; for example from about 0.1 mg/ml to about 0.25 mg/ml.

In some embodiments a priming dose may be delivered through a sub-cutaneous route, by injection, patch, osmotic pump, and the like as known in the art.

Following administration of the priming agent, and allowing a period of time effective for an increase in reticulocyte production, a therapeutic dose of an anti-CD47 agent is administered. The therapeutic dose can be administered in number of different ways. In some embodiments, two or more therapeutically effective doses are administered after a primer agent is administered, e.g. in a weekly dosing schedule. In some embodiments a therapeutically effective dose of an anti-CD47 agent is administered as two or more doses of escalating concentration, in others the doses are equivalent.

In other embodiments, an initial dose of a CD47 binding agent, e.g. a priming dose, is administered by continuous fusion, e.g. as an osmotic pump, delivery patch, etc., where the dose is administered over a period of at least about 6 hours, at least about 12 hours, at least about 24 hours, at least about 2 days, at least about 3 days. Many such systems are known in the art. For example DUROS technology, provides a bi-compartment system separated by a piston. One of the compartments consists of osmotic engine specifically formulated with an excess of solid NaCl, such that it remains present throughout the delivery period and results in a constant osmotic gradient. It also consists of a semi permeable membrane on one end through which water is drawn into the osmotic engine and establishes a large and constant osmotic gradient between the tissue water and the osmotic engine. Other compartment consists of a drug solution with an orifice from which the drug is released due to the osmotic gradient. This helps to provide site specific and systemic drug delivery when implanted in humans. The preferred site of implantation is subcutaneous placement in the inside of the upper arm.

Following administration of the priming agent, and allowing a period of time effective for an increase in reticulocyte production, a therapeutic dose of the anti-CD47 antibody is administered. The therapeutic dose can be administered in number of different ways. In some embodiments, two or more therapeutically effective doses are administered after a primer agent is administered, e.g. in a weekly dosing schedule. In some embodiments a therapeutically effective dose of the anti-CD47 antibody is administered as two or more doses of escalating concentration, in others the doses are equivalent. There is reduced hemagglutination after the priming dose.

Dosing Cycles

A method of treating a human subject having a CD20+ cancer or reducing the size of the CD20+ cancer in the human subject can include at least one cycle of (a) administering an anti-CD47 antibody to the subject at a dose of greater than or equal to 10 mg of antibody per kg of body weight; and (b) administering an anti-CD20 antibody to the subject.

Administration can occur in one or more cycles, for example, a first cycle can have a first dosing scheme and one or more subsequent cycles can have dosing scheme(s) that are distinct from (or the same as) the first cycle.

An anti-CD47 antibody can be administered to a subject in a given cycle as a dose ranging from about 20 to about 67.5 mg of antibody per kg of body weight, optionally 20 to 30 mg of antibody per kg of body weight, optionally 20 mg of antibody per kg of body weight, 30 mg of antibody per kg of body weight, 45 mg of antibody per kg of body weight, 60 mg of antibody per kg of body weight, or 67.5 mg of antibody per kg of body weight.

An anti-CD47 antibody can be administered to a subject in a given cycle, e.g., once every week, once every 2 weeks, or once every 3 weeks.

A priming dose of an anti-CD47 antibody to a subject in a given cycle prior to administering an anti-CD47 antibody to the subject at a dose of greater than or equal to 10 mg of antibody per kg of body weight. A priming dose can be 1 mg of antibody per kg of body weight. A priming dose can be administered to a subject for about 3 hours.

An anti-CD47 antibody can be administered to a subject in a first cycle comprising a priming dose of 1 mg of antibody per kg of body weight on day 1 followed by a dose of 30 mg of antibody per kg of body weight once every week. The first cycle can be 4 weeks in duration. An anti-CD20 antibody can be administered to the subject in the first cycle once every week at a dose of 375 mg/m$^2$ of antibody.

An anti-CD47 antibody can be administered in a second cycle comprising a dose of 30 mg of antibody per kg of body weight once every 2 weeks. The second cycle can be 4 weeks in duration. An anti-CD20 antibody can be administered in the second cycle once every four weeks at a dose of 375 mg/m$^2$ of antibody.

Additional cycles can be used. For example, at least one additional cycle, optionally 1, 2, 3, 4, 5, 6, 7, 8, 9, 10, 11, 12, 13, 14, 15, 16, 17, 18, 19, 20, or greater than 20 additional cycles can be used. The dosing regimen of the at least one additional cycle can be the same as the second cycle, optionally wherein the anti-CD20 antibody portion of the dosing regimen is discontinued after completing 6 total cycles. Optionally the anti-CD20 portion of a given cycle can be continued after completing 6 total cycles, e.g., by pursuing a once per month or a once every other month dosing protocol. An at least one additional cycle can be 4 weeks in duration.

Also disclosed herein is a method of treating or reducing the size of a cancer in a human subject, comprising administering an anti-CD47 antibody (e.g., Hu5F9-G4) and an anti-CD20 antibody (e.g., rituximab) to the subject for at least two distinct cycles of four weeks each, the first cycle comprising (1) administering a priming dose of anti-CD47 antibody at 1 mg of antibody per kg of body weight at time 0 (T0), (2) administering a dose of at least 30 mg (e.g., 30-50, 30, 35, 40, 45, 50 mg) of anti-CD47 antibody per kg of body weight once every week beginning one week after T0 with an additional (optional) loading dose of at least 30 mg/kg (e.g., 30-50, 30, 35, 40, 45, 50 mg) on Day 11 (week 2), and (3) administering a dose of 375 mg/m$^2$ of anti-CD20 antibody once every week; and the second cycle comprising (1) administering a dose of at least 30 mg (e.g., 30-50, 30, 35, 40, 45, 50 mg) of anti-CD47 antibody per kg of body weight once every two weeks, and (2) administering a dose of 375 mg/m$^2$ of anti-CD20 antibody once every four weeks. The second cycle can be repeated as additional cycles (e.g., third, fourth, fifth, sixth, seventh, eighth, ninth, tenth, etc.) without limit or, for example, until clinical benefit is reduced or lost. When reached and starting at Cycle 6 and beyond, anti-CD20 antibody can instead be administered to the subject at a dose of 375 mg/m$^2$ once every eight weeks. Generally, anti-CD47 antibody and anti-CD20 antibody will continue to be administered to the subject as above until the subject loses clinical benefit, e.g., via CR or death. The anti-CD47 antibody can be Hu5F9-G4. The anti-CD20 antibody can be rituximab. The cancer can be at least one of: a CD20+ cancer, a B cell cancer, Non-Hodgkin's lymphoma (NHL), indolent lymphoma, follicular lymphoma (FL), marginal zone lymphoma, or diffuse large B cell lymphoma (DLBCL).

Also disclosed herein is a method of treating or reducing the size of a CD20+ cancer in a human subject, comprising administering an anti-CD47 antibody that is Hu5F9-G4 and an anti-CD20 antibody that is rituximab to the subject for at least two distinct cycles of four weeks each, the first cycle comprising (1) administering a priming dose of anti-CD47 antibody at 1 mg of antibody per kg of body weight at time 0 (T0), (2) administering a dose of at least 30 mg (e.g., 30-50, 30, 35, 40, 45, 50 mg) of anti-CD47 antibody per kg of body weight once every week beginning one week after T0 with an additional (optional) loading dose of at least 30 mg/kg (e.g., 30-50, 30, 35, 40, 45, 50 mg) on Day 11 (week 2), and (3) administering a dose of 375 mg/m$^2$ of anti-CD20 antibody once every week; and the second cycle comprising (1) administering a dose of at least 30 mg (e.g., 30-50, 30, 35, 40, 45, 50 mg) of anti-CD47 antibody per kg of body weight once every two weeks, and (2) administering a dose of 375 mg/m$^2$ of anti-CD20 antibody once every four weeks. The second cycle can be repeated as additional cycles (e.g., third, fourth, fifth, sixth, seventh, eighth, ninth, tenth, etc.) without limit or, for example, until clinical benefit is reduced or lost. When reached and starting at Cycle 6 and beyond, anti-CD20 antibody can instead be administered to the subject at a dose of 375 mg/m$^2$ once every eight weeks. Generally, anti-CD47 antibody and anti-CD20 antibody will continue to be administered to the subject as above until the subject loses clinical benefit, e.g., via CR or death. The CD20+ cancer can be at least one of: a B cell cancer, Non-Hodgkin's lymphoma (NHL), indolent lymphoma, follicular lymphoma (FL), marginal zone lymphoma, or diffuse large B cell lymphoma (DLBCL).

Also disclosed herein is a method of treating a human subject having a CD20+ cancer, comprising administering an anti-CD47 antibody (e.g., Hu5F9-G4) and an anti-CD20 antibody (e.g., rituximab) to the subject for at least two distinct cycles of four weeks each, the first cycle comprising (1) administering a priming dose of anti-CD47 antibody at 1 mg of antibody per kg of body weight at time 0 (T0), (2) administering a dose of at least 30 mg (e.g., 30-50, 30, 35, 40, 45, 50 mg) of anti-CD47 antibody per kg of body weight once every week beginning one week after T0 with an additional (optional) loading dose of at least 30 mg/kg (e.g., 30-50, 30, 35, 40, 45, 50 mg) on Day 11 (week 2), and (3) administering a dose of 375 mg/m$^2$ of anti-CD20 antibody once every week; and the second cycle comprising (1) administering a dose of at least 30 mg (e.g., 30-50, 30, 35, 40, 45, 50 mg) of anti-CD47 antibody per kg of body weight once every two weeks, and (2) administering a dose of 375 mg/m$^2$ of anti-CD20 antibody once every four weeks. The second cycle can be repeated as additional cycles (e.g., third, fourth, fifth, sixth, seventh, eighth, ninth, tenth, etc.) without limit or, for example, until clinical benefit is reduced or lost. When reached and starting at Cycle 6 and beyond, anti-CD20 antibody can instead be administered to the subject at a dose of 375 mg/m² once every eight weeks. Generally, anti-CD47 antibody and anti-CD20 antibody will continue to be administered to the subject as above until the subject loses clinical benefit, e.g., via CR or death. The anti-CD47 antibody can be Hu5F9-G4. The anti-CD20 antibody can be rituximab.

Also disclosed herein is a method of treating a human subject having lymphoma, comprising administering an anti-CD47 antibody (e.g., Hu5F9-G4) and an anti-CD20 antibody (e.g., rituximab) to the subject for at least two distinct cycles of four weeks each, the first cycle comprising (1) administering a priming dose of anti-CD47 antibody at 1 mg of antibody per kg of body weight at time 0 (T0), (2) administering a dose of at least 30 mg (e.g., 30-50, 30, 35, 40, 45, 50 mg) of anti-CD47 antibody per kg of body weight once every week beginning one week after T0 with an additional (optional) loading dose of at least 30 mg/kg (e.g., 30-50, 30, 35, 40, 45, 50 mg) on Day 11 (week 2), and (3) administering a dose of 375 mg/m² of anti-CD20 antibody once every week; and the second cycle comprising (1) administering a dose of at least 30 mg (e.g., 30-50, 30, 35, 40, 45, 50 mg) of anti-CD47 antibody per kg of body weight once every two weeks, and (2) administering a dose of 375 mg/m² of anti-CD20 antibody once every four weeks. The second cycle can be repeated as additional cycles (e.g., third, fourth, fifth, sixth, seventh, eighth, ninth, tenth, etc.) without limit or, for example, until clinical benefit is reduced or lost. When reached and starting at Cycle 6 and beyond, anti-CD20 antibody can instead be administered to the subject at a dose of 375 mg/m² once every eight weeks. Generally, anti-CD47 antibody and anti-CD20 antibody will continue to be administered to the subject as above until the subject loses clinical benefit, e.g., via CR or death. The anti-CD47 antibody can be Hu5F9-G4. The anti-CD20 antibody can be rituximab.

Also disclosed herein is a method of treating a human subject having NHL, comprising administering an anti-CD47 antibody (e.g., Hu5F9-G4) and an anti-CD20 antibody (e.g., rituximab) to the subject for at least two distinct cycles of four weeks each, the first cycle comprising (1) administering a priming dose of anti-CD47 antibody at 1 mg of antibody per kg of body weight at time 0 (T0), (2) administering a dose of at least 30 mg (e.g., 30-50, 30, 35, 40, 45, 50 mg) of anti-CD47 antibody per kg of body weight once every week beginning one week after T0 with an additional (optional) loading dose of at least 30 mg/kg (e.g., 30-50, 30, 35, 40, 45, 50 mg) on Day 11 (week 2), and (3) administering a dose of 375 mg/m² of anti-CD20 antibody once every week; and the second cycle comprising (1) administering a dose of at least 30 mg (e.g., 30-50, 30, 35, 40, 45, 50 mg) of anti-CD47 antibody per kg of body weight once every two weeks, and (2) administering a dose of 375 mg/m² of anti-CD20 antibody once every four weeks. The second cycle can be repeated as additional cycles (e.g., third, fourth, fifth, sixth, seventh, eighth, ninth, tenth, etc.) without limit or, for example, until clinical benefit is reduced or lost. When reached and starting at Cycle 6 and beyond, anti-CD20 antibody can instead be administered to the subject at a dose of 375 mg/m² once every eight weeks. Generally, anti-CD47 antibody and anti-CD20 antibody will continue to be administered to the subject as above until the subject loses clinical benefit, e.g., via CR or death. The anti-CD47 antibody can be Hu5F9-G4. The anti-CD20 antibody can be rituximab.

Also disclosed herein is a method of treating a human subject having diffuse large B cell lymphoma (DLBCL), comprising administering an anti-CD47 antibody (e.g., Hu5F9-G4) and an anti-CD20 antibody (e.g., rituximab) to the subject for at least two distinct cycles of four weeks each, the first cycle comprising (1) administering a priming dose of anti-CD47 antibody at 1 mg of antibody per kg of body weight at time 0 (T0), (2) administering a dose of at least 30 mg (e.g., 30-50, 30, 35, 40, 45, 50 mg) of anti-CD47 antibody per kg of body weight once every week beginning one week after T0 with an additional (optional) loading dose of at least 30 mg/kg (e.g., 30-50, 30, 35, 40, 45, 50 mg) on Day 11 (week 2), and (3) administering a dose of 375 mg/m² of anti-CD20 antibody once every week; and the second cycle comprising (1) administering a dose of at least 30 mg (e.g., 30-50, 30, 35, 40, 45, 50 mg) of anti-CD47 antibody per kg of body weight once every two weeks, and (2) administering a dose of 375 mg/m² of anti-CD20 antibody once every four weeks. The second cycle can be repeated as additional cycles (e.g., third, fourth, fifth, sixth, seventh, eighth, ninth, tenth, etc.) without limit or, for example, until clinical benefit is reduced or lost. When reached and starting at Cycle 6 and beyond, anti-CD20 antibody can instead be administered to the subject at a dose of 375 mg/m² once every eight weeks. Generally, anti-CD47 antibody and anti-CD20 antibody will continue to be administered to the subject as above until the subject loses clinical benefit, e.g., via CR or death. The anti-CD47 antibody can be Hu5F9-G4. The anti-CD20 antibody can be rituximab.

Also disclosed herein is a method of treating a human subject having indolent lymphoma comprising administering an anti-CD47 antibody (e.g., Hu5F9-G4) and an anti-CD20 antibody (e.g., rituximab) to the subject for at least two distinct cycles of four weeks each, the first cycle comprising (1) administering a priming dose of anti-CD47 antibody at 1 mg of antibody per kg of body weight at time 0 (T0), (2) administering a dose of at least 30 mg (e.g., 30-50, 30, 35, 40, 45, 50 mg) of anti-CD47 antibody per kg of body weight once every week beginning one week after T0 with an additional (optional) loading dose of at least 30 mg/kg (e.g., 30-50, 30, 35, 40, 45, 50 mg) on Day 11 (week 2), and (3) administering a dose of 375 mg/m² of anti-CD20 antibody once every week; and the second cycle comprising (1) administering a dose of at least 30 mg (e.g., 30-50, 30, 35, 40, 45, 50 mg) of anti-CD47 antibody per kg of body weight once every two weeks, and (2) administering a dose of 375 mg/m² of anti-CD20 antibody once every four weeks. The second cycle can be repeated as additional cycles (e.g., third, fourth, fifth, sixth, seventh, eighth, ninth, tenth, etc.) without limit or, for example, until clinical benefit is reduced or lost. When reached and starting at Cycle 6 and beyond, anti-CD20 antibody can instead be administered to the subject at a dose of 375 mg/m² once every eight weeks. Generally, anti-CD47 antibody and anti-CD20 antibody will continue to be administered to the subject as above until the subject loses clinical benefit, e.g., via CR or death. The anti-CD47 antibody can be Hu5F9-G4. The anti-CD20 antibody can be rituximab.

Also disclosed herein is a method of treating a human subject having follicular lymphoma (FL), comprising administering an anti-CD47 antibody (e.g., Hu5F9-G4) and an anti-CD20 antibody (e.g., rituximab) to the subject for at least two distinct cycles of four weeks each, the first cycle comprising (1) administering a priming dose of anti-CD47 antibody at 1 mg of antibody per kg of body weight at time 0 (T0), (2) administering a dose of at least 30 mg (e.g., 30-50, 30, 35, 40, 45, 50 mg) of anti-CD47 antibody per kg of body weight once every week beginning one week after T0 with an additional (optional) loading dose of at least 30 mg/kg (e.g., 30-50, 30, 35, 40, 45, 50 mg) on Day 11 (week 2), and (3) administering a dose of 375 mg/m² of anti-CD20 antibody once every week; and the second cycle comprising (1) administering a dose of at least 30 mg (e.g., 30-50, 30, 35, 40, 45, 50 mg) of anti-CD47 antibody per kg of body weight once every two weeks, and (2) administering a dose of 375 mg/m² of anti-CD20 antibody once every four weeks. The second cycle can be repeated as additional cycles (e.g., third, fourth, fifth, sixth, seventh, eighth, ninth, tenth, etc.) without limit or, for example, until clinical benefit is reduced or lost. When reached and starting at Cycle 6 and beyond, anti-CD20 antibody can instead be administered to the subject at a dose of 375 mg/m² once every eight weeks. Generally, anti-CD47 antibody and anti-CD20 antibody will continue to be administered to the subject as above until the subject loses clinical benefit, e.g., via CR or death. The anti-CD47 antibody can be Hu5F9-G4. The anti-CD20 antibody can be rituximab.

Also disclosed herein is a method of treating a human subject having marginal zone lymphoma, comprising administering an anti-CD47 antibody (e.g., Hu5F9-G4) and an anti-CD20 antibody (e.g., rituximab) to the subject for at least two distinct cycles of four weeks each, the first cycle comprising (1) administering a priming dose of anti-CD47 antibody at 1 mg of antibody per kg of body weight at time 0 (T0), (2) administering a dose of at least 30 mg (e.g., 30-50, 30, 35, 40, 45, 50 mg) of anti-CD47 antibody per kg of body weight once every week beginning one week after T0 with an additional (optional) loading dose of at least 30 mg/kg (e.g., 30-50, 30, 35, 40, 45, 50 mg) on Day 11 (week 2), and (3) administering a dose of 375 mg/m² of anti-CD20 antibody once every week; and the second cycle comprising (1) administering a dose of at least 30 mg (e.g., 30-50, 30, 35, 40, 45, 50 mg) of anti-CD47 antibody per kg of body weight once every two weeks, and (2) administering a dose of 375 mg/m² of anti-CD20 antibody once every four weeks. The second cycle can be repeated as additional cycles (e.g., third, fourth, fifth, sixth, seventh, eighth, ninth, tenth, etc.) without limit or, for example, until clinical benefit is reduced or lost. When reached and starting at Cycle 6 and beyond, anti-CD20 antibody can instead be administered to the subject at a dose of 375 mg/m² once every eight weeks. Generally, anti-CD47 antibody and anti-CD20 antibody will continue to be administered to the subject as above until the subject loses clinical benefit, e.g., via CR or death. The anti-CD47 antibody can be Hu5F9-G4. The anti-CD20 antibody can be rituximab.

Administration

In the methods described herein, compositions, e.g., an anti-CD47 antibody and, optionally, an additional agent, are administered to a subject. The compositions can be administered by parenteral, topical, intravenous, intra-abdominal, intra-tumoral, oral, subcutaneous, intra-arterial, intracranial, intraperitoneal, intranasal or intramuscular means. A typical route of administration is intravenous or intra-tumoral, although other routes can be equally effective.

In some embodiments the anti-CD47 antibody and/or the additional agent is administered intra-abdominally. In some embodiments the anti-CD47 antibody and/or the additional agent is administered intravenously. In some embodiments the anti-CD47 antibody and/or the additional agent is administered intra-tumorally. In one embodiment, a priming dose of the anti-CD47 antibody is administered, and the priming dose is delivered subcutaneously. In some embodiments, the anti-CD47 antibody and the additional agent are administered concurrently. In some embodiments, the anti-CD47 antibody and the additional agent are administered sequentially.

The active agents are administered within a period of time to produce an additive or synergistic effect on depletion of cancer cells in the host. Methods of administration include, without limitation, systemic administration, intra-tumoral administration, etc. Usually the anti-CD47 antibody is administered within about a period of about 45 days, about 30 days, about 21 days, about 14 days, about 10 days, about 8 days, about 7 days, about 6 days, about 5 days, about 4 days, about 3 days, about 2 days, about 1 day or substantially the same day as the additional agent. In some embodiments the anti-CD47 antibody is administered prior to the additional agent. In some embodiments the anti-CD47 antibody is administered after the additional agent. The agents can be considered to be combined if administration scheduling is such that the serum level of both agents is at a therapeutic level at the same time. Administration may be repeated as necessary for depletion of the cancer cell population.

One or more antibodies disclosed herein can be administered by a medical professional, optionally a physician.

One or more antibodies disclosed herein can be administered by the subject.

Clinical Endpoints

The methods described herein result in at least one improved endpoint compared to baseline.

A method disclosed herein can result in an objective response (OR) in a subject. An objective response is a partial response or complete remission as defined by Cheson, Lugano, or similar NHL response criteria.

A method disclosed herein can result disease control in a subject. Disease control is stable disease plus objective response.

A method disclosed herein can result in a partial response (PR) in a subject. PR is a shrinkage of the tumor by at least 50% by imaging criteria (CT or PET/CT) without complete disappearance of tumor lesions. By PET/CT criteria, a PR is as described above or by reduced metabolic uptake compared with baseline and residual masses of any size (Lugano criteria, Cheson et al., JCO 2014).

A method disclosed herein can result in a complete response (CR) in a subject. Cheson et al., JCO 2014.

A method disclosed herein can result in stable disease (SD) in a subject. Cheson et al., JCO 2014.

A method disclosed herein can reduce the size of a subject's cancer relative to baseline where baseline is determined prior to administration of anti-CD47 antibody.

A method disclosed herein can result in a reversal of refractoriness to rituximab in a subject.

Pharmaceutical Compositions

The methods described herein include administration of pharmaceutical compositions comprising the anti-CD47 antibody and/or the additional agent.

Typically, the compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. Langer, Science 249: 1527, 1990 and Hanes, Advanced Drug Delivery Reviews 28: 97-119, 1997. The agents of this invention can be administered in the form of a depot injection or implant preparation which can be formulated in such a manner as to permit a sustained or pulsatile release of the active ingredient. The pharmaceutical compositions are generally formulated as sterile, substantially isotonic and in full compliance with all Good Manufacturing Practice (GMP) regulations of the U.S. Food and Drug Administration.

The pharmaceutical compositions can be administered in a variety of unit dosage forms depending upon the method of administration. For example, unit dosage forms suitable for oral administration include, but are not limited to, powder, tablets, pills, capsules and lozenges. It is recognized that compositions of the invention when administered orally, should be protected from digestion. This is typically accomplished either by complexing the molecules with a composition to render them resistant to acidic and enzymatic hydrolysis, or by packaging the molecules in an appropriately resistant carrier, such as a liposome or a protection barrier. Means of protecting agents from digestion are well known in the art.

The compositions for administration will commonly comprise an antibody or other ablative agent dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as needed to approximate physiological conditions such as pH adjusting and buffering agents, toxicity adjusting agents and the like, e.g., sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs (e.g., Remington's Pharmaceutical Science (15th ed., 1980) and Goodman & Gillman, The Pharmacological Basis of Therapeutics (Hardman et al., eds., 1996)).

"Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

"Pharmaceutically acceptable salts and esters" means salts and esters that are pharmaceutically acceptable and have the desired pharmacological properties. Such salts include salts that can be formed where acidic protons present in the compounds are capable of reacting with inorganic or organic bases. Suitable inorganic salts include those formed with the alkali metals, e.g. sodium and potassium, magnesium, calcium, and aluminum. Suitable organic salts include those formed with organic bases such as the amine bases, e.g., ethanolamine, diethanolamine, triethanolamine, tromethamine, N methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). Pharmaceutically acceptable esters include esters formed from carboxy, sulfonyloxy, and phosphonoxy groups present in the compounds, e.g., $C_{1-6}$ alkyl esters. When there are two acidic groups present, a pharmaceutically acceptable salt or ester can be a mono-acid-mono-salt or ester or a di-salt or ester; and similarly where there are more than two acidic groups present, some or all of such groups can be salified or esterified. Compounds named in this invention can be present in unsalified or unesterified form, or in salified and/or esterified form, and the naming of such compounds is intended to include both the original (unsalified and unesterified) compound and its pharmaceutically acceptable salts and esters. Also, certain compounds named in this invention may be present in more than one stereoisomeric form, and the naming of such compounds is intended to include all single stereoisomers and all mixtures (whether racemic or otherwise) of such stereoisomers.

The terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects to a degree that would prohibit administration of the composition.

Kits

Also described herein are kits comprising the active agents, e.g., an anti-CD47 antibody and, optionally, an additional agent, and formulations thereof, and instructions for use. The kit can further contain a least one additional reagent, e.g. an anti-CD20 agent such as rituximab. Kits typically include a label indicating the intended use of the contents of the kit. The term label includes any writing, or recorded material supplied on or with the kit, or which otherwise accompanies the kit.

Also provided are kits for use in the various methods disclosed herein. The subject kits include a primer agent and an anti-CD47 agent. In some embodiments, a kit comprises two or more primer agents. In some embodiments, a kit comprises two or more anti-CD47 agents. In some embodiments, a primer agent is provided in a dosage form (e.g., a priming dosage form). In some embodiments, a primer agent is provided in two or more different dosage forms (e.g., two or more different priming dosage forms). In some embodiments, an anti-CD47 agent is provided in a dosage form (e.g., a therapeutically effective dosage form). In some embodiments, an anti-CD47 agent is provided in two or more different dosage forms (e.g., two or more different therapeutically effective dosage forms). In the context of a kit, a primer agent and/or an anti-CD47 agent can be provided in liquid or sold form in any convenient packaging (e.g., stick pack, dose pack, etc.).

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), flash drive, and the like, on which the information has been recorded. Yet another form of these instructions that may be present is a website address which may be used via the internet to access the information at a removed site.

Sequences

In some embodiments, the methods described herein include administration of antibodies with sequences described herein; e.g., the heavy chain, light chain, and/or CDR sequences described herein. The sequences of the administered antibodies can be, e.g., at least 95, 96, 97, 98, 99, or 100% identical to the sequences described herein.

The term percent "identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (<www.ncbi.nlm.nih.gov/>).

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W. H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences,* 18th Edition (Easton, Pennsylvania: Mack Publishing Company, 1990); Carey and Sundberg *Advanced Organic Chemistry* $3^{rd}$ Ed. (Plenum Press) Vols A and B(1992).

Example 1: Hu5F9-G4 in Combination with Rituximab in Human Patients with Relapsed/Refractory B-Cell Non-Hodgkin's Lymphoma Introduction Non-Hodgkin's lymphoma (NHL) is among the most common cancers in the USA and Europe, with more than 70,000 and 93,000 new cases diagnosed every year, respectively. Diffuse large B-cell lymphoma (DLBCL) is an aggressive subtype of NHL with high relapse rate and poor long-term survival. In addition, few treatment options are available to patients with indolent lymphoma who have relapsed or are refractory to rituximab. Novel and effective therapies are needed to address these high unmet medical needs. Hu5F9-G4 is a monoclonal antibody that targets CD47, an anti-phagocytic cell surface protein. Nonclinical studies have demonstrated that blockade of CD47 signaling through this antibody eliminates human tumor cells including NHL, through facilitating phagocytosis by macrophages. Additional nonclinical studies demonstrate that anti-CD47 antibodies can synergize with Fc receptor-activating anti-cancer antibodies including rituximab. Combination therapy with Hu5F9-G4 and rituximab, an anti-CD20 monoclonal antibody, demonstrated a synergistic anti-cancer response compared to either agent alone in nonclinical models of NHL.

This Phase 1b/2 trial establishes the safety and tolerability and dosing strategy of Hu5F9-G4 in combination with rituximab in patients with relapsed/refractory B-cell NHL. Hu5F9-G4 and rituximab were both administered intravenously. Initially, this trial utilized a reduced starting dose of Hu5F9-G4 in combination with full doses of rituximab. Subsequent dose cohorts escalated the dose of Hu5F9-G4. In addition, preliminary anti-cancer activity was investigated with this antibody combination.

Patient Eligibility

Inclusion Criteria were as follows:
1. Adults≥18 years
2. Phase 1b only: B-cell NHL expressing CD20 by immunohistochemistry (IHC) or flow cytometry, relapsed or refractory to at least 2 prior lines of therapy
3. DLBCL Phase 2 cohort: Histologically confirmed de novo or transformed DLBCL expressing CD20 by IHC or flow cytometry, refractory to frontline therapy; or relapsed or refractory to second line salvage regimens or autologous hematopoietic cell transplantation
4. Indolent lymphoma Phase 2 cohort: Histologically confirmed marginal zone or follicular lymphoma (Grade 1-3a) expressing CD20 by IHC or flow cytometry, relapsed or refractory to at least 2 prior lines of therapy
5. Eastern Cooperative Oncology Group (ECOG) score 0-2
6. Disease that is measurable or assessable for response per Lugano Classification for lymphomas
7. Laboratory measurements, blood counts:
   Hemoglobin≥9.5 g/dL
   Absolute neutrophil count (ANC)≥$1.0\times10^9$/mL
   Platelets≥$50\times10^9$/mL 8. Laboratory measurements, hepatic function:
    Aspartate aminotransferase (AST)/alanine aminotransferase (ALT)<5×upper limit of normal (ULN)
    Bilirubin≤1.5× or 3.0×ULN and primarily unconjugated if patient has a documented history of Gilbert's syndrome or a genetic equivalent
9. Laboratory measurements, renal function:
    Serum creatinine≤1.5×ULN or calculated glomerular filtration rate (GFR)>40 mL/min/1.73 m2
10. Negative urine or serum pregnancy test within 30 days before enrollment and within 72 hours before the first administration of Hu5F9-G4 for women of childbearing potential.
11. Females of childbearing potential should be willing to use 1 highly effective method of contraception during the study and for 12 months after the last dose of rituximab or 4 months after the last dose of Hu5F9-G4, whichever occurs later
12. Males should be willing to use 1 effective method of contraception during the study and for 12 months after the last dose of rituximab or 4 months after the last dose of Hu5F9-G4, whichever occurs later, if the partner is a female of childbearing potential
13. Subject has provided informed consent
14. Should be willing and able to comply with clinic visits and procedures outlined in the study protocol
15. Phase 2 only: Willing to consent to 1 mandatory pre-treatment and 1 on-treatment tumor biopsy, unless not feasible as determined by the Investigator (reasons include but are not limited to lack of accessible tumor tissue to biopsy and patient safety issues)

Exclusion Criteria were as follows:
1. Patients with active brain metastases. (Patients with stable treated central nervous system [CNS] lesions who are off corticosteroid therapy for at least 3 weeks are not considered active.)
2. Prior anti-cancer therapy including chemotherapy, hormonal therapy, or investigational agents within 2 weeks or within at least 4 half-lives prior to Hu5F9-G4 dosing (up to a maximum of 4 weeks), whichever is longer. In all situations, the maximum required washout period will not exceed 4 weeks prior to the day of first treatment with Hu5F9-G4. Low dose steroids (oral prednisone or equivalent≤20 mg per day), localized non-CNS radiotherapy, pre-existing previous hormonal therapy with LHRH agonists for prostate cancer, and treatment with bisphosphonates and RANKL inhibitors are not criteria for exclusion.
3. Known active or chronic hepatitis B or C infection or human immunodeficiency virus (HIV).
4. Red blood cell (RBC) transfusion dependence, defined as requiring more than 2 units of RBC transfusions during the 4-week period prior to screening. RBC transfusions are permitted during screening and prior to enrollment to meet the hemoglobin inclusion criteria.
5. History of hemolytic anemia or Evans syndrome in the last 3 months.
6. Positive Direct Antiglobulin Test (DAT).
7. Prior treatment with CD47 or signal regulatory protein alpha (SIRPα) targeting agents.
8. Second malignancy, except treated basal cell or localized squamous skin carcinomas, localized prostate cancer, or other malignancy for which patients are not on active anti-cancer therapy as defined in Exclusion Criterion 2.
9. Hypersensitivity to the active substance, to murine proteins, or to any of the other excipients of rituximab listed at: RITUXAN® (rituximab) prescribing information http://www.gene.com/download/pdf/rituxan_prescribing.pdf; MabThera® (rituximab) prescribing information http://www.ema.europa.eu/docs/en_GB/document_library/EPAR_-Product_Information/human/000165/WC500025821.pdf. Each link is as of Apr. 27, 2017.
10. Significant medical diseases or conditions, as assessed by the Investigators and
    Sponsor that would substantially increase the risk-benefit ratio of participating in the study. This includes but is not limited to acute myocardial infarction within the last 6 months, unstable angina, uncontrolled diabetes mellitus, significant active infections, severely immunocompromised state, and congestive heart failure New York Heart Association (NYHA) Class II-IV.
11. History of psychiatric illness or substance abuse likely to interfere with ability to comply with protocol requirements or give informed consent.
12. Pregnancy or active breastfeeding.

Study Objectives

Primary Objectives (1) Investigation of the safety and tolerability, and definition of Phase 2 dose for Hu5F9-G4 in combination with rituximab.

(2) In Phase 2, evaluation of efficacy of Hu5F9-G4 in combination with rituximab in patients with indolent lymphoma and DLBCL as measured by the overall response rate (ORR).

Secondary Objectives (1) In Phase 1b and 2, evaluation of pharmacokinetic (PK) profile of Hu5F9-G4 in combination with rituximab.

(2) In Phase 1b and 2, evaluation of immunogenicity of Hu5F9-G4 in combination with rituximab.

(3) In Phase 2, evaluation of efficacy of Hu5F9-G4 in combination with rituximab in indolent lymphoma and DLBCL as measured by the duration of response, best overall response, progression free survival, and overall survival.

(4) Evaluation of response rates according to LYRIC criteria for lymphomas.

Exploratory Objectives (1) Assessment of biomarkers of immune cell efficacy and tumor penetration of Hu5F9-G4 in combination with rituximab.

(2) Assessment of efficacy in molecular subtypes of NHL.

Endpoints

Primary (1) Dose-limiting toxicities (DLTs) (Phase 1b only) and adverse events (AEs) according to NCI CTCAE, Version 4.03.

(2) Phase 2: Objective response according to the Lugano Classification for lymphomas.

Secondary (1) Phase 1b and 2: Concentration versus time measurements for Hu5F9-G4 in combination with rituximab and PK parameters, including maximum plasma concentration ($C_{max}$), time to maximum concentration ($T_{max}$), terminal half-life ($t_{1/2}$), area under the curve (AUC), clearance (CL), and volume of distribution during the terminal phase ($V_z$).

(2) Phase 1b and 2: Anti-drug antibodies to Hu5F9-G4 and rituximab.

(3) Phase 2: Duration of response (DOR), best overall response (BOR), progression-free survival (PFS), and overall survival (OS).

(4) Objective response according to the LYRIC criteria for lymphomas.

Exploratory (1) CD47 receptor occupancy on peripheral RBCs and white blood cells (WBCs), and lymphoma cells, where applicable.

(2) Pharmacodynamic markers of Hu5F9-G4 biological activity potentially including, but not limited to, circulating cytokine profiles, T-cell receptor sequencing on circulating T cells, mass cytometry (CyTOF)/flow cytometry of circulating leukocytes, and T-cell activation studies.

(3) In patients undergoing tumor biopsies, Hu5F9-G4 saturation of tumor cells and changes in the tumor microenvironment including, but not limited to, macrophage and T-cell tumor infiltration.

(4) In patients undergoing tumor biopsies, correlation of anti-cancer response to molecular subtypes of NHL including, but not limited to, cell-of-origin in DLBCL and BCL2, BCL6, and MYC mutation/expression status.

Intervention and Mode of Delivery

Hu5F9-G4 is a humanized monoclonal antibody against CD47 and rituximab is a chimeric monoclonal antibody against CD20. Both drugs were administered intravenously. Hu5F9-G4 was administered on Days 1, 8, 15, and 22 for all Phase 1b cycles while rituximab was administered on Days 8, 15, and 22 for the first cycle followed by Day 1 for Cycles 2-6.

Duration of Intervention and Evaluation

Phase 1b/2: For the Phase 1b part of the study, patients were treated with Hu5F9-G4 and rituximab in a standard 3+3 dose escalation design. DLT safety evaluation used for determination of the maximum tolerated dose (MTD) occurred within the first 4 weeks. A response assessment occurred every 2 cycles (8 weeks) until disease progression. Rituximab was or is administered for a total of 6 cycles, while Hu5F9-G4 treatment was or is extended beyond 6 cycles for those who do not have disease progression.

Number of Patients

Phase 1b: 9 to 18 patients total

Per dose level:

Level 1: 3-6

Level 2: 3-6

Level 3: 3-6

Phase 2: 48 patients (24 patients for indolent lymphoma; 24 patients for DLBCL)

Study Total: 57-66 patients (assuming progression to Stage 2 of Phase 2)

Statistical Methods

The Efficacy Analysis Set (EAS) will be used for the analysis of the primary efficacy endpoint in Phase 2. The DLT Analysis Set was used in Phase 1b to determine the MTD. The Full Analysis Set (FAS) will be used for OS, PFS, and safety analysis in Phase 2. Per Protocol (PP) set and PK analysis set (PAS) was or will be used for additional analyses. The PAS was or will be used for summaries of PK concentration data and PK parameters. Data from Phase 1b and Phase 2 are or will be summarized separately. In Phase 2, data for indolent lymphoma and DLBCL will be summarized separately.

Sample Size Calculations

Phase 1b: The sample size was determined based on the number of dose levels evaluated and the emerging study drug-related toxicities. This phase includes up to 18 patients.

Phase 2: Simon Two-Stage Minimax Design

Indolent lymphoma: The null hypothesis that the true response rate is 20% will be tested against a one-sided alternative. The null hypothesis of 20% is based on single agent rituximab activity in patients previously treated and refractory to rituximab. The assumption is that Hu5F9-G4 in combination with rituximab will result in an overall response rate (ORR) of at least 40%. In the first stage, 14 patients will be accrued. If there are 2 or fewer responses in these 14 patients after at least 8 weeks of study participation, enrollment into this arm will be stopped. Otherwise, 10 additional patients will be accrued for a total of 28. The null hypothesis will be rejected if 8 or more responses are observed in 24 patients. This design yields a type I error rate of 0.10 and power of 0.80 when the true response rate is 40%.

DLBCL: The null hypothesis that the true response rate is 20% will be tested against a one-sided alternative. The null hypothesis of 20% is based on single agent rituximab activity in patients receiving at least 2 prior lines of rituximab-containing therapies. The assumption is that Hu5F9-G4 in combination with rituximab will result in an ORR of at least 40%. In the first stage, 14 patients will be accrued. If there are 2 or fewer responses in these 14 patients after at least 8 weeks of study participation, enrollment into this arm will be stopped. Otherwise, 10 additional patients will be accrued for a total of 24. The null hypothesis will be rejected if 8 or more responses are observed in 24 patients. This design yields a type I error rate of 0.10 and power of 0.80 when the true response rate is 40%.

Study Design Schema and Summary

FIG. 1 shows the study design schema for: Phase 1b/2 Trial of Hu5F9-G4 in Combination with Rituximab in Patients with Relapsed/Refractory B-cell Non-Hodgkin's Lymphoma.

Eligible patients had CD20-expressing B-cell lymphoma relapsed/refractory to at least 2 prior lines of therapy, an Eastern Cooperative Oncology Group (ECOG) (Oken M M, Creech R H, Tormey D C, et al. Toxicity and response criteria of the Eastern Cooperative Oncology Group. Am J Clin Oncol 1982; 5:649-55.) performance status score of 0-2 (a 5-point scale where higher numbers reflect greater disability), hemoglobin≥9.5 g/dL, absolute neutrophil count≥1×10$^9$/mL and platelets≥50×10$^9$/mL.

The Phase 1b study had 3 dose-escalation cohorts using a 3+3 design, which enrolls a minimum of 3 patients per cohort for every dose level, with the safety profile informing the dose escalation for the next cohort (Le Tourneau C, Lee J J, Siu L L. Dose escalation methods in phase I cancer clinical trials. J Natl Cancer Inst 2009; 101:708-20.). Dose-limiting toxicities were assessed during the first 28 days. All patients received a 5F9 priming dose of 1 mg/kg intravenously followed 1 week later by escalating maintenance doses of 10, 20 or 30 mg/kg weekly. In the 30 mg/kg cohort, an additional 30 mg/kg dose was given on day 11. For all cohorts, rituximab was given weekly at a 375 mg/m² dose intravenously in cycle 1 starting week 2, and then monthly through cycles 2-6. 5F9 was administered until disease progression, lack of clinical benefit or unacceptable toxicity. Primary objectives evaluated safety, tolerability, and determining the recommended Phase 2 dose range of 5F9 in combination with rituximab. Secondary objectives evaluated efficacy, and pharmacokinetic (PK) and immunogenicity profiles of 5F9.

Adverse events were assessed throughout the study and 30 days after the last study drug dose by the National Cancer Institute Common Terminology Criteria for Adverse Events, version 4.03 (Services USDoHaH. Common Terminology Criteria for Adverse Events (CTCAE). Version 4.03. 2010). A treatment-emergent adverse event was defined as an adverse event that occured or worsened in intensity or frequency following initiation of treatment (regardless of causality). A treatment-related adverse event was defined as an adverse event as described above that is related to study drug (either 5F9 and/or rituximab) as assessed by the investigator. Patients were evaluated for efficacy every 8 weeks with computed tomography and 18F-fluorodeoxyglucose-position-emission tomography. Investigator-assessed efficacy was evaluated by Lugano Criteria (Cheson B D, Fisher R I, Barrington S F, et al. Recommendations for initial evaluation, staging, and response assessment of Hodgkin and non-Hodgkin lymphoma: the Lugano classification. J Clin Oncol 2014; 32:3059-68). Bone marrow biopsies were required to confirm complete response if disease involvement was present at screening. Rituximab-refractory status was defined as failure to respond to, or progression during, any previous rituximab-containing regimen (monotherapy or combined with chemotherapy), or progression within 6 months of the last rituximab dose (Sehn L H, Chua N, Mayer J, et al. Obinutuzumab plus bendamustine versus bendamustine monotherapy in patients with rituximab-refractory indolent non-Hodgkin lymphoma (GADOLIN): a randomised, controlled, open-label, multicentre, phase 3 trial. The lancet oncology 2016; 17:1081-93.).

5F9 serum levels were measured using a validated ELISA assay. Anti-drug antibodies were measured using a tiered (screening, confirmatory, and titer) approach using a validated electrochemiluminescence assay. CD47 receptor occupancy on target cells was evaluated using a flow cytometry-based assay. 5F9 antibody tumor penetrance was detected using an anti-human IgG4 antibody measured by immunohistochemistry.

Example 2: Human Results

Safety of Hu5F9-G4

Table A shows that Hu5F9-G4 was safe and well-tolerated in a monotherapy setting.

TABLE A

SOLID TUMOR MONOTHERAPY SUMMARY

| Toxicity (Patients Treated with 1 mg/kg Prime and 20 mg/kg Maintenance Dose | Toxicity Grade | | | |
|---|---|---|---|---|
| (n = 37) | 1 | 2 | 3 | 4 |
| Anemia | 4 (11%) | 10 (27%) | 5 (14%) | 0 (0%) |
| Hemagglutination | 12 (32%) | 4 (11%) | 1 (3%) | 0 (0%) |
| Hyperbilirubinemia | 2 (5%) | 2 (5%) | 1 (3%) | 0 (0%) |
| Thrombocytopenia | 4 (11%) | 1 (3%) | 0 (0%) | 0 (0%) |
| Lymphocyte count decreased | 1 (3%) | 0 (0%) | 5 (14%) | 0 (0%) |
| Non-cardiac Chest Pain/Chest Pain | 1 (3%) | 0 (0%) | 1 (3%) | 0 (0%) |
| Headache | 14 (38%) | 1 (3%) | 0 (0%) | 0 (0%) |
| Nausea | 5 (14%) | 0 (0%) | 0 (0%) | 0 (0%) |
| Fatigue | 16 (43%) | 1 (3%) | 0 (0%) | 0 (0%) |
| Pyrexia | 10 (27%) | 1 (3%) | 0 (0%) | 0 (0%) |
| Chills | 16 (43%) | 1 (3%) | 0 (0%) | 0 (0%) |
| Photopsia | 5 (14%) | 0 (0%) | 0 (0%) | 0 (0%) |
| Infusion-related reaction | 2 (5%) | 1 (3%) | 1 (3%) | 0 (0%) |
| AST elevation | 0 (0%) | 0 (0%) | 0 (0%) | 1 (3%) |
| ALT elevation | 0 (0%) | 0 (0%) | 0 (0%) | 1 (3%) |

The red blood cell findings were not clinically significant and were easily managed by a proprietary priming dose strategy. No consistent AEs were observed at high or extended exposure and no overlapping toxicities with anti-tumor antibodies. MTD was not reached with dose escalation up to 45 mg/kg and >130 patients treated. Patients were treated over >72 weeks without increases in safety signals being observed.

Anemia

Figure 2A:
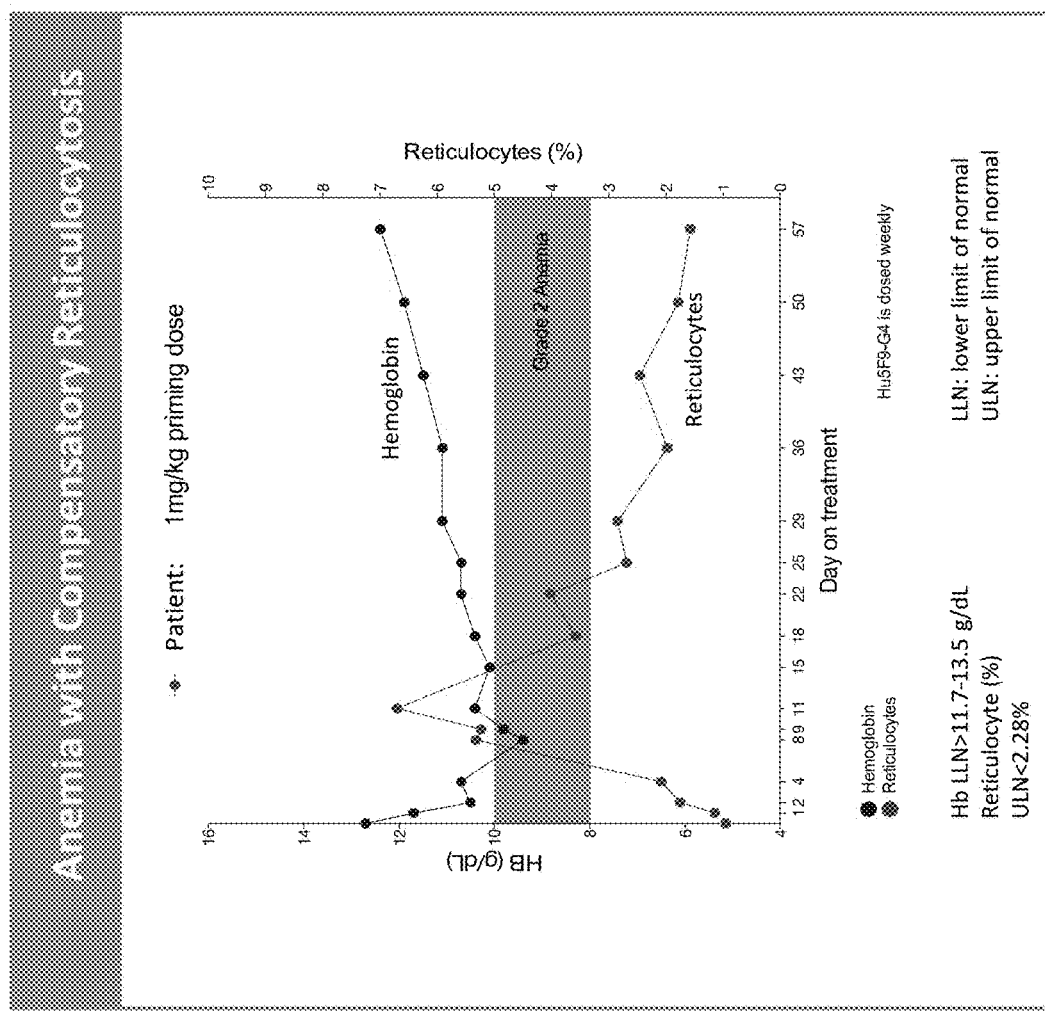
FIG. 2A shows anemia with compensatory reticulocytosis.

FIG. 2A shows anemia with compensatory reticulocytosis. An initial priming dose results in an early, temporary and mild decline in hemoglobin levels, likely through clearance of aged RBCs. Hemoglobin levels return to baseline even with continued treatment with 5F9 at significantly higher doses (e.g., up to 30 mg/kg).

Anemia: Hgb drops by 1.5-2 g/dL and then gradually resolves. Anemia Gr 1-2 was observed with an onset within 7-10 days of 1st dose. These findings are consistent with NHP toxicology studies. Associated reversible reticulocytosis was observed and resolves during the dosing period. Only one tumor patient (solid tumor) to-date (as of January 2018) needed a transfusion (n>58 patients).

Testings and Safety of Hu5F9-G4+Rituximab in B Cell NHL

Table B shows tolerability of Hu5F9-G4+Rituximab in B cell NHL

TABLE B

| ADVERSE EVENT (COHORTS 1-3, N = 22) | TOXICITY GRADE | | | | |
| --- | --- | --- | --- | --- | --- |
| | All grades | 1 | 2 | 3 | 4 |
| Subjects reporting at least one AE | 18 (81.8%) | 4 (18.2%) | 12 (54.5%) | 2 (9.1%) | 0 (0%) |
| Chills | 8 (36.4%) | 5 (22.7%) | 2 (9.1%) | 1 (4.5%) | 0 (0%) |
| Pyrexia | 5 (22.7%) | 4 (18.2%) | 1 (4.5%) | 0 (0%) | 0 (0%) |
| Headache | 8 (36.4%) | 5 (22.7%) | 3 (13.6%) | 0 (0%) | 0 (0%) |
| Infusion related reaction | 4 (18.2%) | 0 (0%) | 3 (13.6%) | 1 (4.5%) | 0 (0%) |
| Fatigue | 4 (18.2%) | 2 (9.1%) | 2 (9.1%) | 0 (0%) | 0 (0%) |
| Anemia | 4 (18.2%) | 2 (9.1%) | 1 (4.5%) | 1 (4.5%) | 0 (0%) |
| Nausea | 3 (13.6%) | 3 (13.6%) | 0 (0%) | 0 (0%) | 0 (0%) |
| Vomiting | 3 (13.6%) | 1 (4.5%) | 2 (9.1%) | 0 (0%) | 0 (0%) |
| Neutropenia/Neutrophil count decreased | 3 (13.6%) | 2 (9.1%) | 1 (4.5%) | 0 (0%) | 1* (4.5%) |
| Thrombocytopenia/ platelet count decreased | 3 (13.6%) | 2 (9.1%) | 1 (4.5%) | 0 (0%) | 0 (0%) |
| Hyperbilirubinemia | 2 (9.1%) | 0 (0%) | 2 (9.1%) | 0 (0%) | 0 (0%) |
| Blood bilirubin increased | 2 (9.1%) | 2 (9.1%) | 0 (0%) | 0 (0%) | 0 (0%) |
| Hypoasthenia | 2 (9.1%) | 2 (9.1%) | 0 (0%) | 0 (0%) | 0 (0%) |
| Arthralgia | 2 (9.1%) | 1 (4.5%) | 1 (4.5%) | 0 (0%) | 0 (0%) |
| Back pain | 2 (9.1%) | 0 (0%) | 2 (9.1%) | 0 (0%) | 0 (0%) |

Figure 2B:
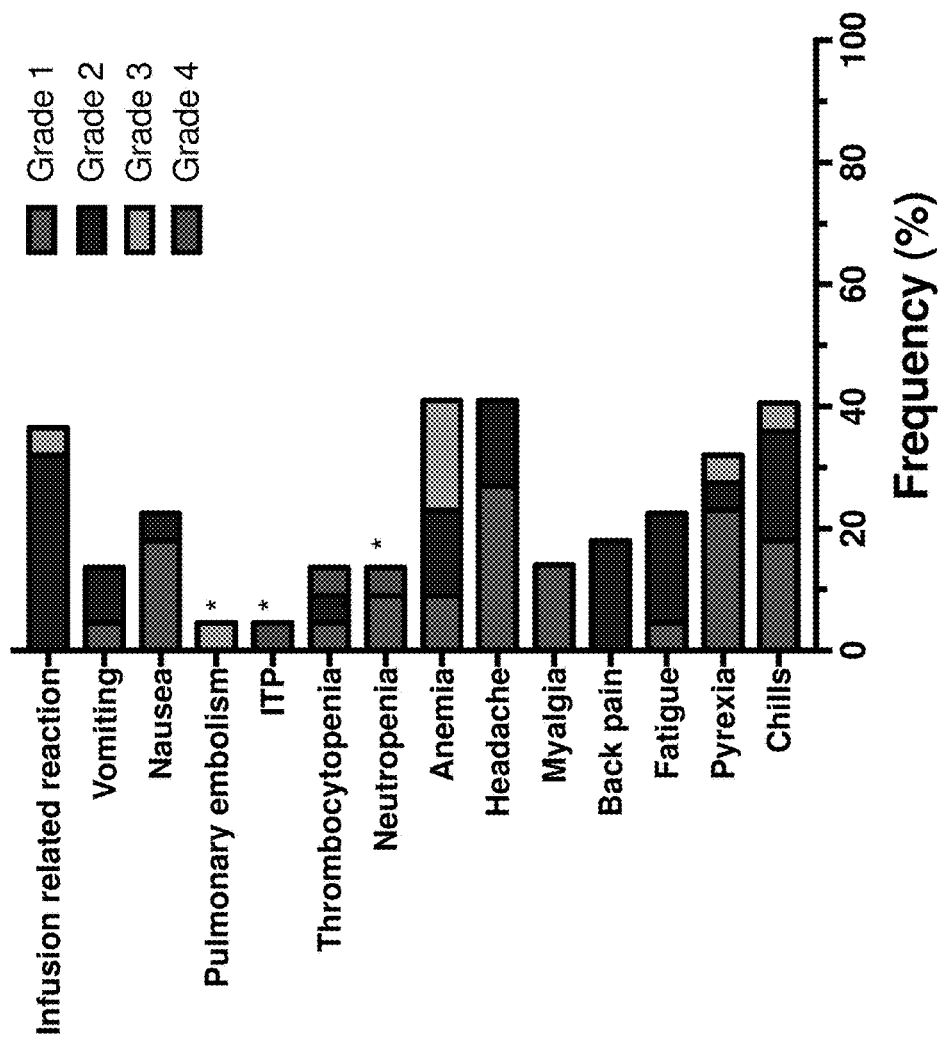
FIG. 2B shows treatment-related adverse events to 5F9 and/or rituximab. For infusion related reaction, left side of bar is Grade 2, right side is grade 3. For vomiting, left side of bar is grade 1, right side is grade 2. For nausea, left side of bar is grade 1, right side is grade 2. For pulmonary embolism, bar is grade 3. For ITP, bar is grade 4. For thrombocytopenia, left side of bar is grade 1, middle is grade 2, right is grade 4. For neutropenia, left side of bar is grade 1, right side is grade 4. For anemia, left side of bar is grade 1, middle is grade 2, right is grade 3. For headache, left side of bar is grade 1, right is grade 2. For back pain, bar is grade 2. For fatigue, left side of bar is grade 1, right is grade 2. For pyrexia, left side of bar is grade 1, middle is grade 2, right is grade 3. For chills, left side of bar is grade 1, middle is grade 2, right is grade 3.

FIG. 2B shows treatment-related adverse events to 5F9 and/or rituximab. 5F9+rituximab was well-tolerated. Common treatment-related AEs were chills, headache, anemia, and fever. All were grade 1-2 except 3 G3 AEs (chills, fever, anemia). Prime/maintenance 5F9 dosing significantly mitigated on-target anemia, a mostly first dose effect with spontaneous recovery. Only 2 patients needed a one-time transfusion. 3 separate DLTs observed across 10, 20 mg/kg and 30 mg/kg dose levels. No autoimmune AEs seen, minimal Grade 3/4 toxicities observed. Treatment discontinuation due to AE occurred in only 1 of 22 (4.5%) of patients as of April 2018. Patients treated long term (up to 18+ months) without any significant late safety signals. A maximum tolerated dose (MTD) was not reached up to 30 mg/kg weekly of 5F9 dosing.

5F9 is well-tolerated in combination with rituximab with no MTD achieved to-date. On target anemia is transient and significantly mitigated by use of a prime/maintenance dosing regimen.

Figure 2C:
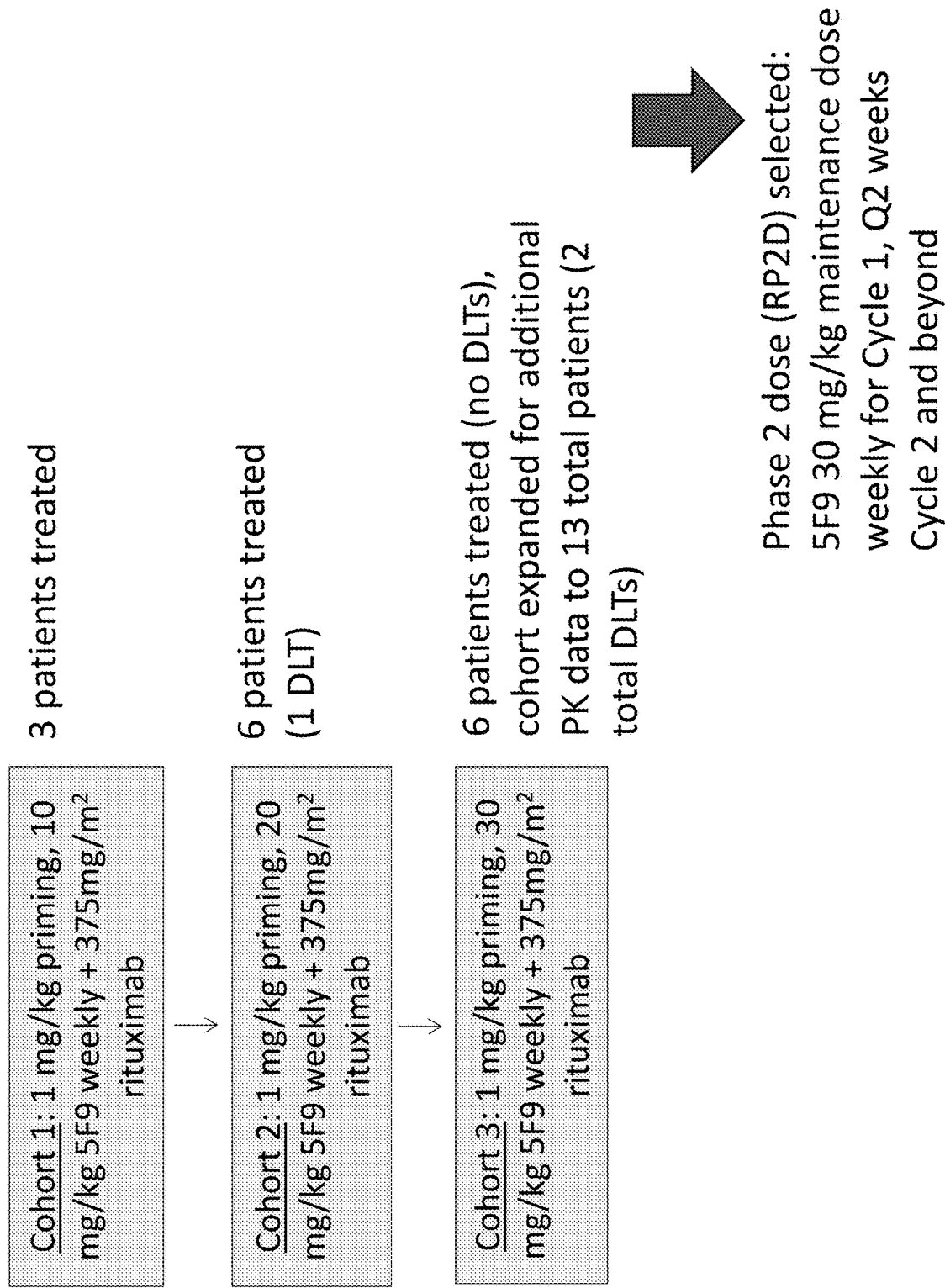
FIG. 2C shows the Phase 1B dose escalation of the 22 patients treated across cohorts.

FIG. 2C shows the Phase 1B dose escalation of the 22 patients treated across cohorts.

Hu5F9-G4 Achieves Target PK Levels at Clinical Doses

Figure 3:
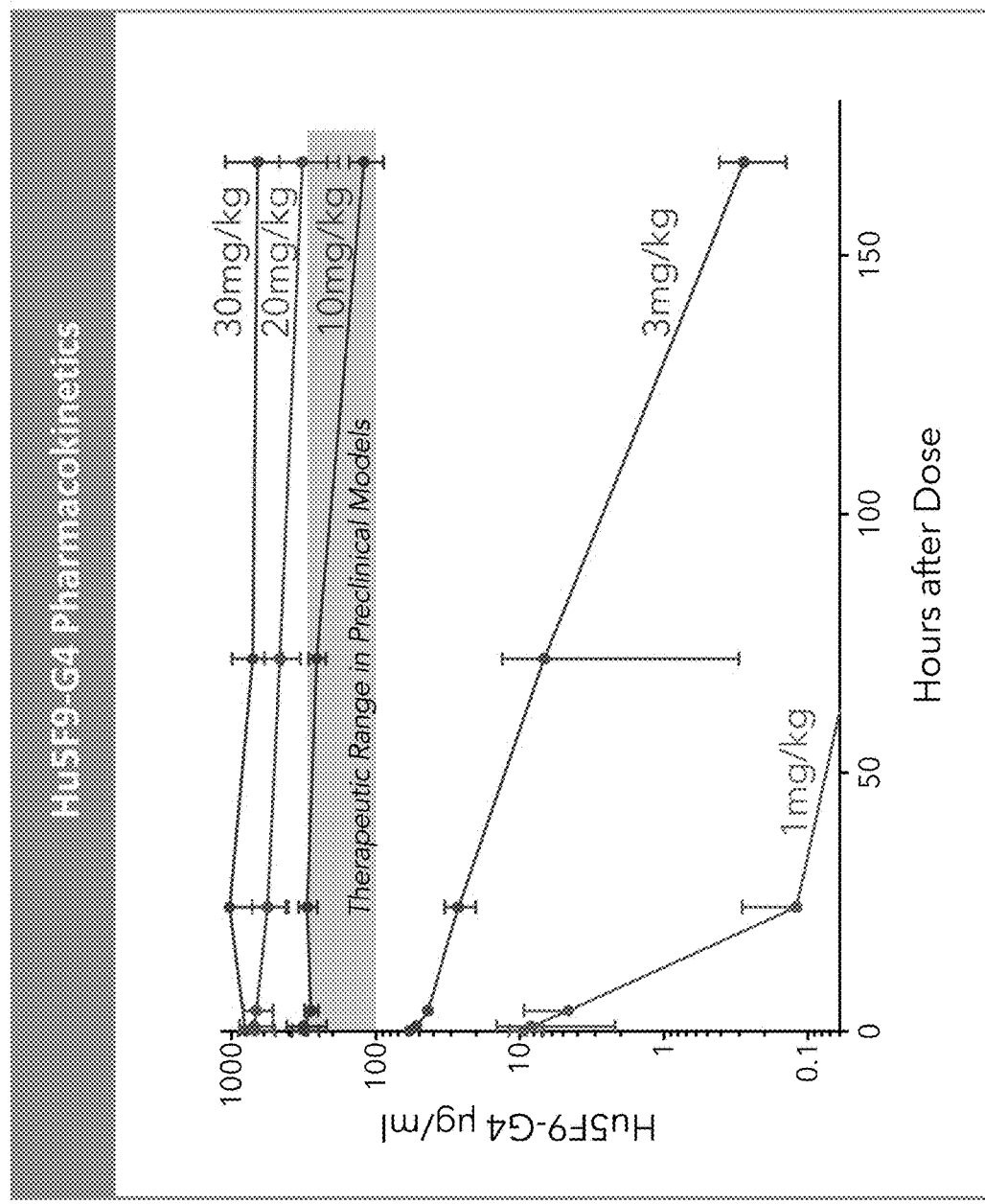
FIG. 3 shows Hu5F9-G4 pharmacokinetics.

FIG. 3 shows Hu5F9-G4 pharmacokinetics.

Hu5F9-G4 overcomes the non-linear CD47 tissue antigen sink at 10 mg/kg or higher. Antibody half-life post saturation was ~14 days. Free plasma drug levels exceeded preclinical activity thresholds (>100 to 250 μg/ml).

CD47 Receptor Occupancy and 5F9 Tumor Penetration

Figure 4A:
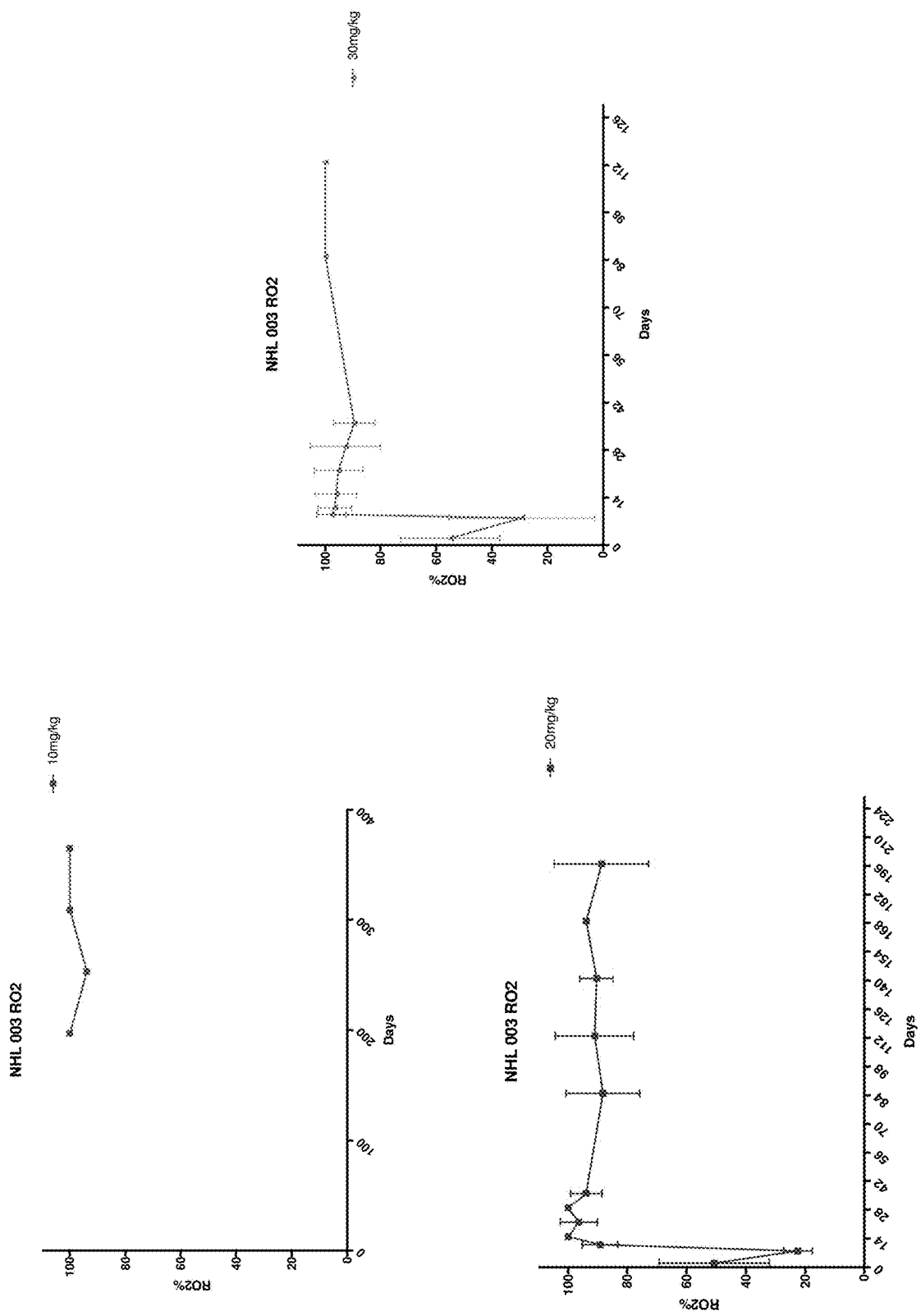
FIG. 4A shows CD47 receptor occupancy in the peripheral blood on WBCs. High CD47 target receptor occupancy was observed rapidly across dose levels; CD47 Receptor Occupancy (RO) Demonstrates>90% Saturation.

FIG. 4A shows CD47 receptor occupancy in the peripheral blood on WBCs. High CD47 target receptor occupancy was observed rapidly across dose levels; CD47 Receptor Occupancy (RO) Demonstrates>90% Saturation, approaching near 100% saturation on circulating WBCs. In addition, 5F9 tumor penetration has been observed in the tumor environment on day 36 of treatment in a DLBCL patient (data not shown; anti-IgG4 staining was used to detect 5F9 on supraclavicular lymph node 20 mg/kg 5F9 maintenance given).

Antitumor Activity and Duration

Table C1 shows a summary of Antitumor Activity Observed with Hu5F9 and Rituximab Combination in R/R-NHL as of January 2018

TABLE C1

| Response | All Patients n = 22 | DLBCL n = 15 | Follicular Lymphoma n = 7 |
| --- | --- | --- | --- |
| ORR | 50% | 40% | 71% |
| PR | 27% | 20% | 43% |
| CR | 23% | 20% | 29% |
| Disease control rate (CR + PR + SD) | 64% | 60% | 71% |

Table C2 shows a summary of Antitumor Activity Observed with Hu5F9 and Rituximab Combination in R/R-NHL as of April 2018.

TABLE C2

| Response | All n = 22 | DLBCL n = 15 | FL n = 7 |
| --- | --- | --- | --- |
| Objective Response | 11 (50%) | 6 (40%) | 5 (71%) |
| Complete Response | 8 (36%) | 5 (33%) | 3 (43%) |
| Partial Response | 3 (14%) | 1 (7%) | 2 (29%) |
| Stable Disease | 3 (14%) | 3 (20%) | 0 (0%) |
| Progressive Disease | 8 (36%) | 6 (40%) | 2 (29%) |
| Disease Control Rate (CR + PR + SD) | 14 (64%) | 9 (60%) | 5 (71%) |

90% (9/10) of evaluable responding patients (DLBCL and FL) have continued on therapy, suggesting durability; treatment has been between 9-54+ weeks and is ongoing (data not shown).

As of January 2018, 90% of responding patients continued in response, including 1 patient for 13+ months (4.4 month median follow up). As of April 2018, the ORR was 50%, 36% achieved CR. % ORR/CR was 40/33 in DLBCL and 71/43 in FL, respectively. Greater than 90% of patients continued in response with a median duration of follow up of 6.2 months for DLBCL and 8.1 months for FL. The longest patient in response at this data cut-off was 14.8 months and ongoing.

Figure 4B:
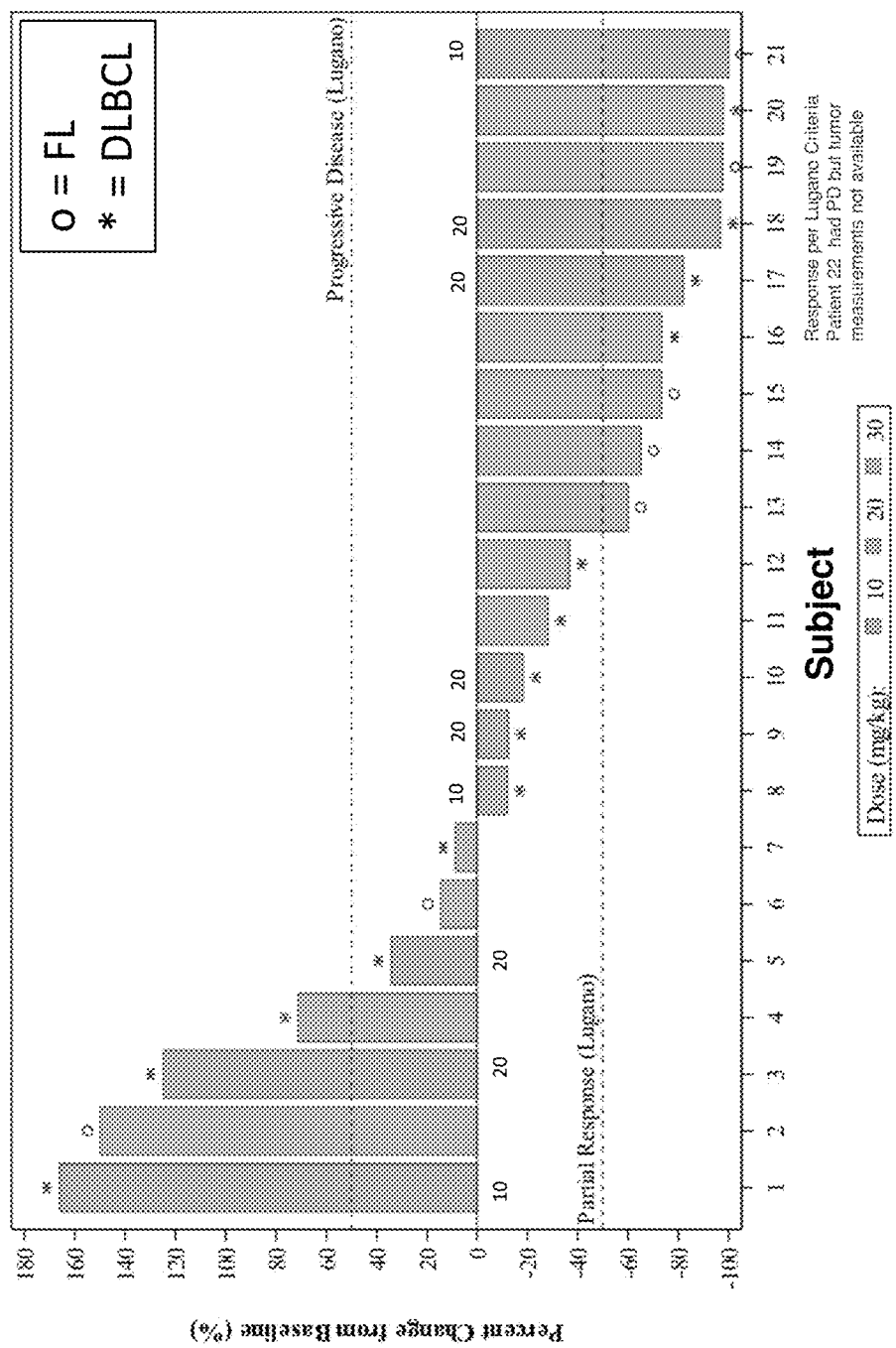
FIG. 4B shows anti-tumor activity observed with 5F9 and rituximab in relapsed or refractory NHL as of April 2018. Dosages at 10 mg/kg and 20 mg/kg are labeled on the 0 axis; the remainder of the bars are 30 mg/kg.

FIG. 4B shows anti-tumor activity observed with 5F9 and rituximab in relapsed or refractory NHL as of April 2018. Multiple CRs have been observed in both DLBCL and FL phase 1b populations. The median time to response is rapid, within the first two months. Efficacy is observed in rituximab-refractory patients.

Figure 4C:
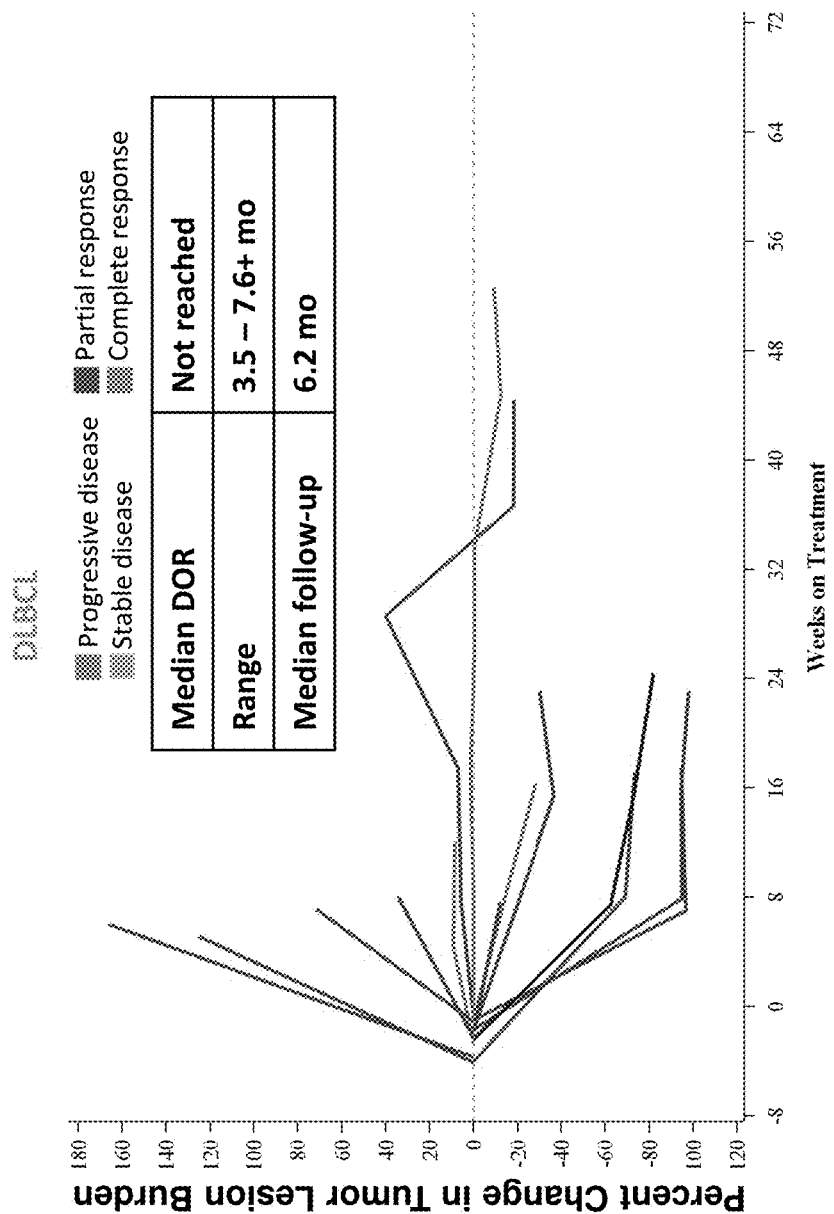
FIG. 4C shows durable responses in phase 1b DLBCL and FL patients as of April 2018.
Figure 4C:
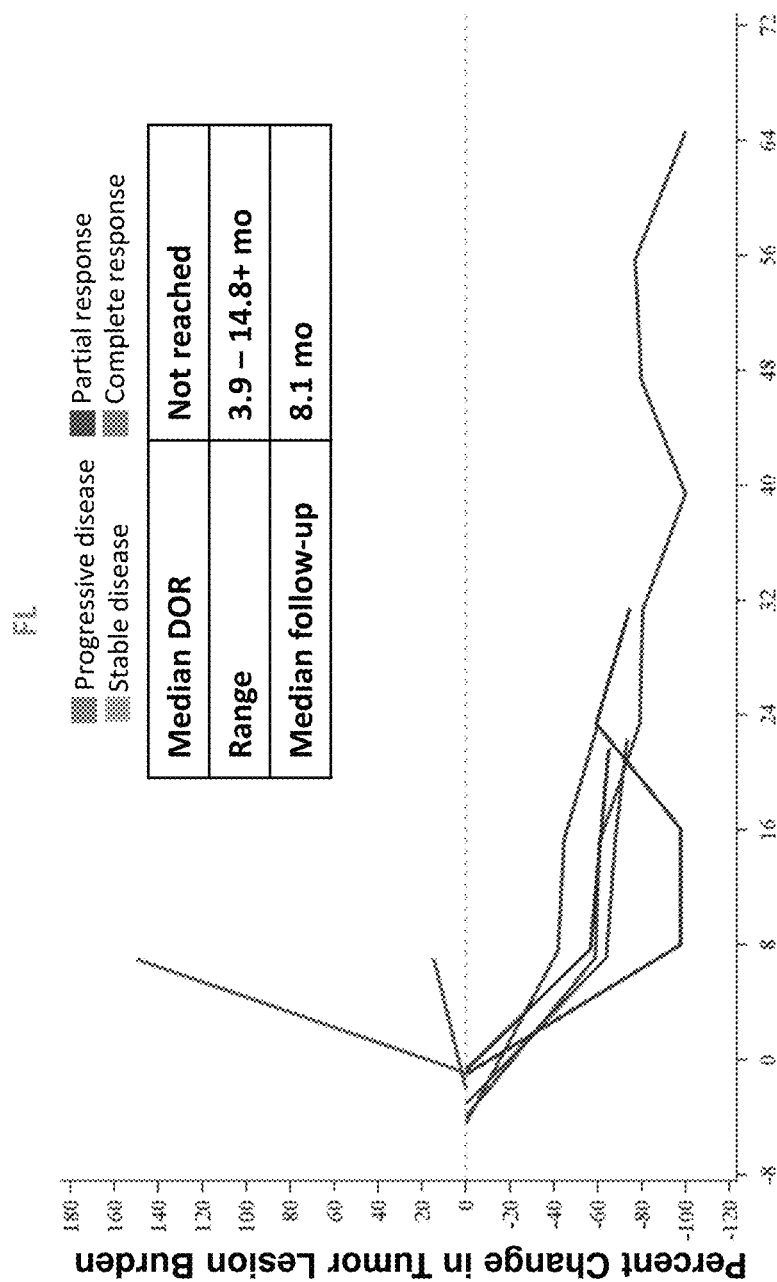

FIG. 4C shows durable responses in phase 1b DLBCL and FL patients as of April 2018. One out of 11 responding patients has had disease progression with median follow-up over 6 mos. One DLBCL patient converted from PR at 2 months to CR at 4 months (and ongoing). Median duration of response not reached in either cohort with longest patient in CR for over 14 months.

NHL Patient Demographics for Phase 1b

Table D1 shows NHL patient demographics for Phase 1b as of January 2018.

TABLE D1

| Characteristic | All Patients, n = 22 (%) | DLBCL, n = 15 (%) | FL, n = 7 (%) |
|---|---|---|---|
| Median age (range) | 59 (44-82) | 60 (44-82) | 59 (44-75) |
| Gender | | | |
| Male | 12 (55%) | 7 (47%) | 5 (71%) |
| Female | 10 (45%) | 8 (53%) | 2 (29%) |
| Diagnosis | — | 15 (68.2) | 7 (31.8) |
| Lugano Stage at Diagnosis | | | |
| I-II | 4 (18.2) | 3 (20) | 1 (14.3) |
| III-IV | 15 (68.2) | 11 (73.3) | 4 (57.1) |
| Unknown | 3 (13.6) | 1 (6.7) | 2 (28.6) |
| ECOG Performance Status: | | | |
| 0 | 7 (32%) | 3 (20%) | 4 (57%) |
| 1 | 14 (64%) | 11 (73.3) | 3 (43%) |
| 2 | 1 (5%) | 1 (7%) | 0 (0%) |
| Median number of prior therapies (range) | 4 (2-10) | 4 (2-10) | 4 (2-9) |
| Rituxinnab refractory (any regimen) | 20 (90.9) | 14 (93.3) | 6 (85.7) |
| Rituxinnab refractory (last regimen) | 19 (86.4) | 14 (93.3) | 5 (71.4) |
| Refractory to last regimen | 15 (68.2) | 10 (66.7) | 5 (71.4) |
| Prior autologous transplant | 5 (22.7) | 2 (13.3) | 3 (42.9) |
| Cell of origin (DLBCL) | | | |
| ABC | n/a | 3 (20) | n/a |
| GCB | | 6 (40) | |
| Unknown | | 6 (40) | |
| Hu5F9-G4 treatment dose level | | | |
| 10 mg/kg | 3 (13.6) | 2 (13.3) | 1 (14.3) |
| 20 mg/kg | 6 (27.3) | 6 (40) | 0 (0) |
| 30 mg/kg | 13 (59.1) | 7 (46.7) | 6 (85.7) |

Table D2 shows NHL patient demographics for Phase 1b as of April 2018.

TABLE D2

| Characteristic | All n = 22 (%) | DLBCL n = 15 (%) | FL n = 7 (%) |
|---|---|---|---|
| Median age (range) | 59 (44-82) | 60 (44-82) | 59 (44-75) |
| Sex: | | | |
| Male | 12 (55%) | 7 (47%) | 5 (71%) |
| Female | 10 (45%) | 8 (53%) | 2 (29%) |
| Diagnosis | — | 15 (68.2) | 7 (31.8) |
| Median number of prior therapies (range) | 4 (2-10) | 4 (2-10) | 4 (2-9) |
| ECOG Performance Status: | | | |
| 0 | 7 (32%) | 3 (20%) | 4 (57%) |
| 1 | 14 (64%) | 11 (73%) | 3 (43%) |
| 2 | 1 (5%) | 1 (7%) | 0 (0%) |
| Lugano Stage at Diagnosis: | | | |
| I-II | 4 (18%) | 3 (20%) | 1 (14%) |
| III-IV | 15 (68%) | 11 (73%) | 4 (57%) |
| Unknown | 3 (14%) | 1 (7%) | 2 (29%) |
| Refractory to prior rituximab regimen | 21 (95%) | 14 (93%) | 7 (100%) |
| Refractory to last regimen | 14 (64%) | 9 (60%) | 5 (71%) |
| Prior autologous stem cell transplant | 4 (18%) | 2 (13%) | 2 (29%) |
| 5F9 treatment dose level | | | |
| 10 mg/kg | 3 (14%) | 2 (13%) | 1 (14%) |
| 20 mg/kg | 6 (27%) | 6 (40%) | 0 (0%) |
| 30 mg/kg | 13 (59%) | 7 (47%) | 6 (86%) |

Note that: Rituximab refractory (any regimen) means: failure to respond to, or progression during, any previous rituximab-containing regimen, or progression within 6 months of the last rituximab dose (Sehn et al., 2016: GADOLIN trial: Obinutuzumab approval in FL); Rituximab refractory (last regimen) means: failure to respond to, or progression during, last previous rituximab-containing regimen, or progression within 6 months of the last rituximab dose.

The patient population was a heavily pre-treated population with a median of 4 prior lines of therapy, with some patients having 9 or 10 prior lines of therapy. All FL patients tested received prior rituximab and alkylator therapy. Over 90% of patients were refractory to a prior rituximab-containing regimen.

Hu5F9-G4+Rituximab Eliminates Disease in 2 Heavily-Refractory Patients

Figure 5:
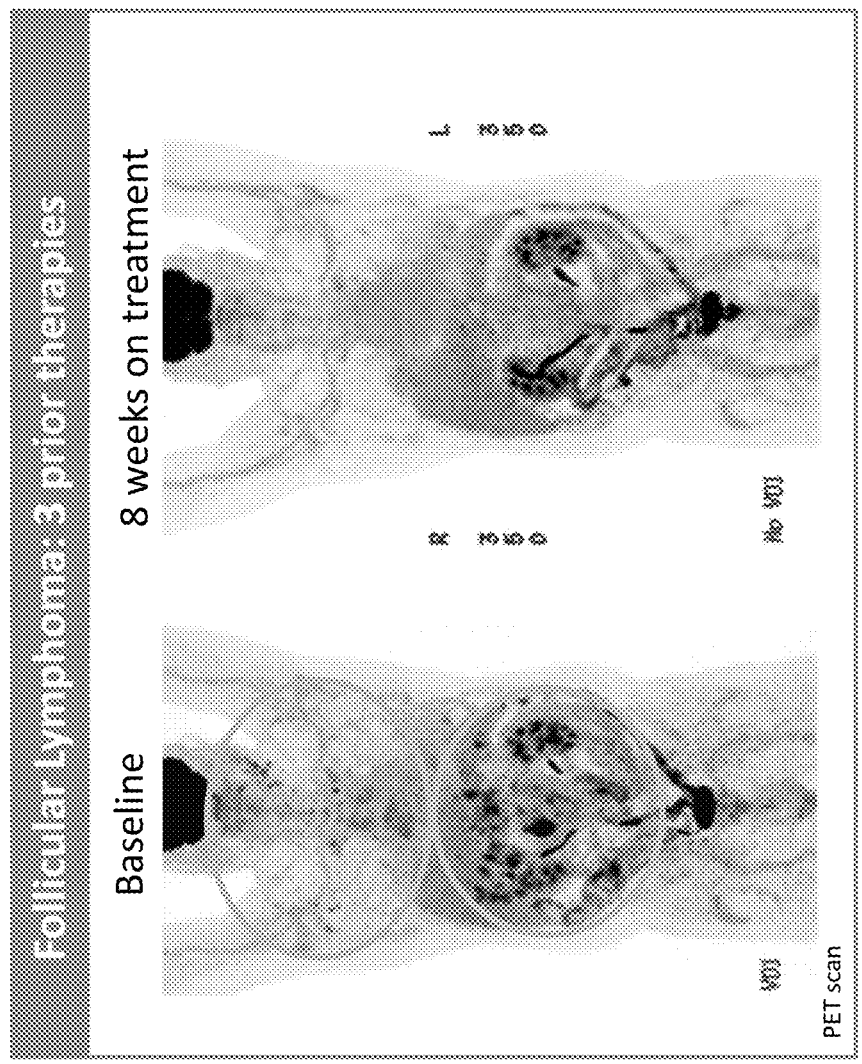
FIG. 5 shows two examples of patients with heavily-refractory disease who had all cancer eliminated via treatment with Hu5F9-G4+Rituximab.
Figure 5:
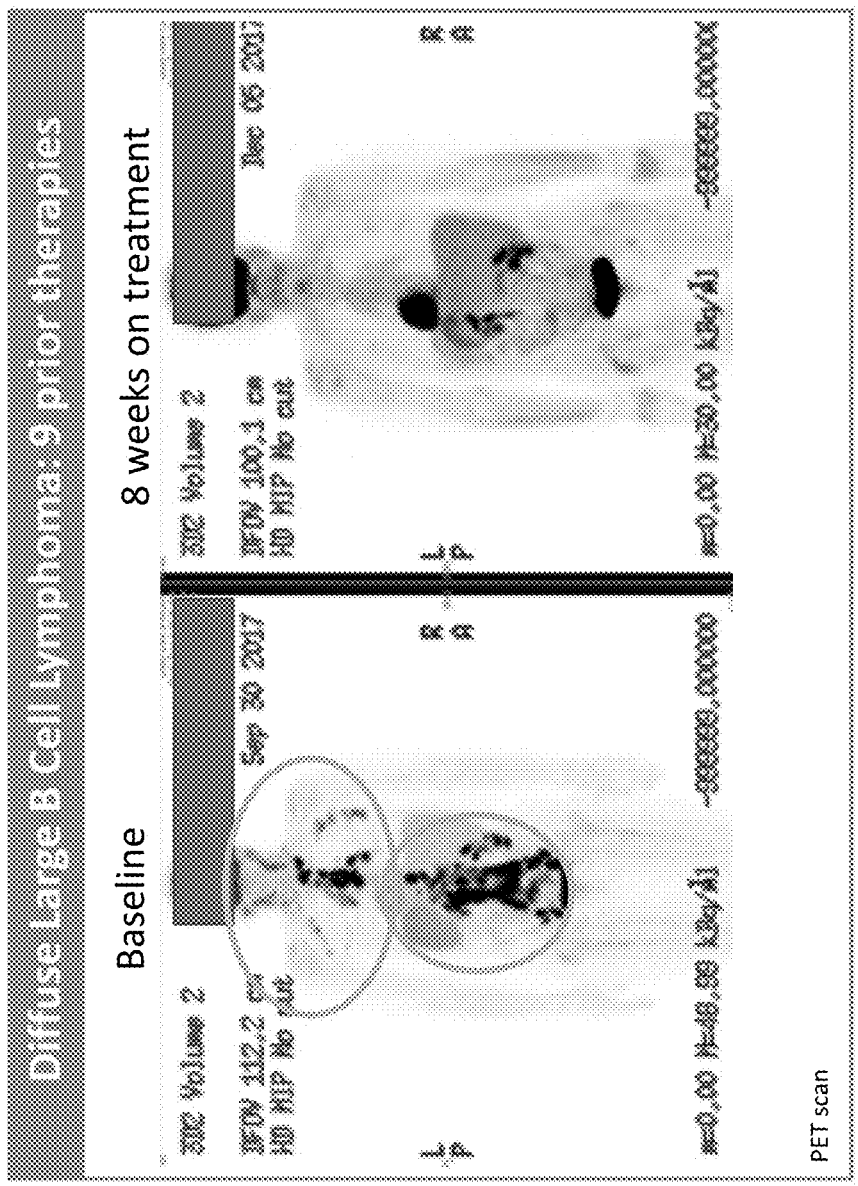

FIG. 5 shows two examples of patients with heavily-refractory disease who had all cancer eliminated via treatment with Hu5F9-G4+Rituximab. Both follicular lymphoma and diffuse large B cell lymphoma patients have achieved complete elimination of cancer on Hu5F9-G4+ rituximab therapy.

Figure 6A:
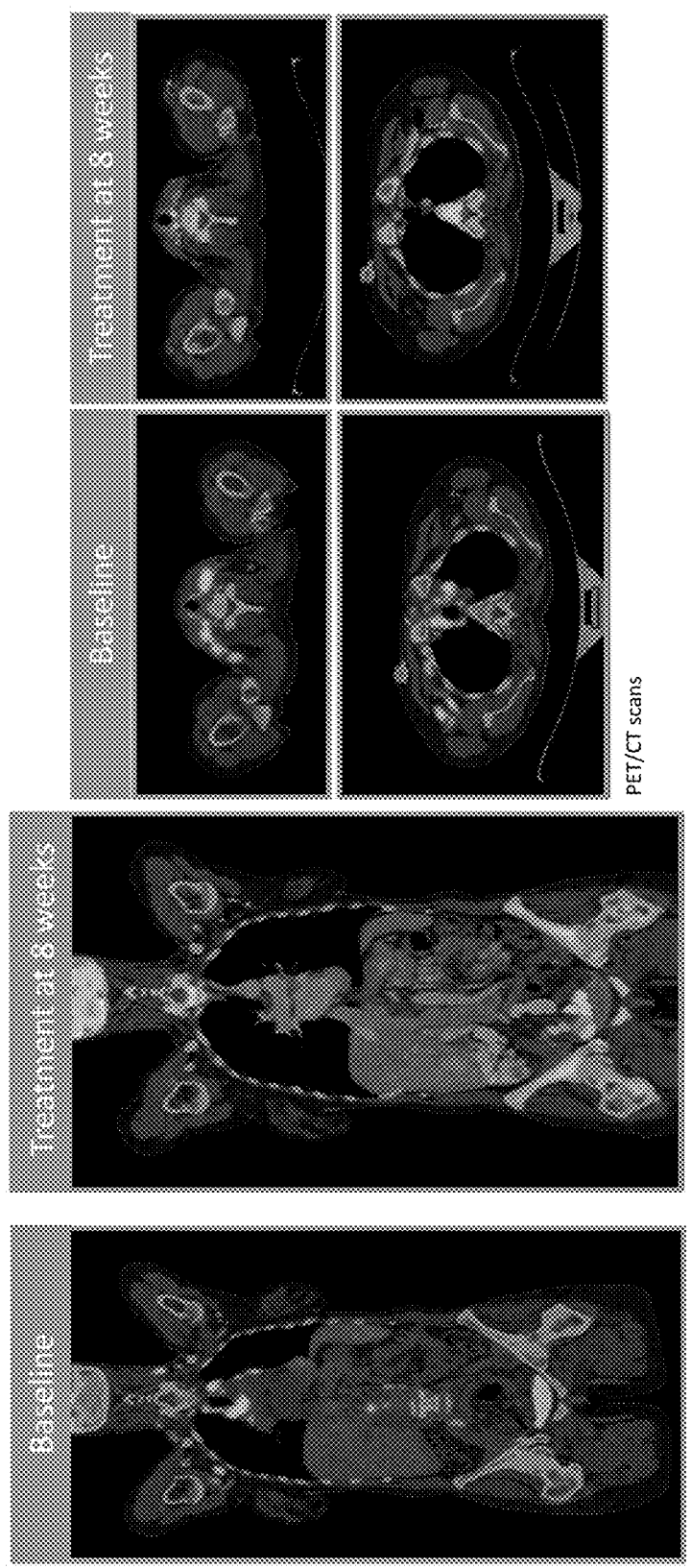
FIG. 6A shows an additional example of a patient with heavily-refractory disease who had all cancer eliminated via treatment with Hu5F9-G4+Rituximab.

Hu5F9-G4+Rituximab Eliminates Disease in Additional Heavily-Refractory Patients FIG. 6A shows an additional example of a patient with heavily-refractory disease who had all cancer eliminated via treatment with Hu5F9-G4+Rituximab.

The patient was a 58 year old woman with DLBCL, rituximab-refractory, bulky disease, with 4 prior lines of therapy with rapid disease progression prior to study entry. Treatment at 8 weeks achieved a CR, including elimination of all lymphoma lesions and bone marrow disease. Resolution of B symptoms (fevers, weight loss), with substantial improvement in activities of daily living was reported/observed within several weeks.

Figure 6B:
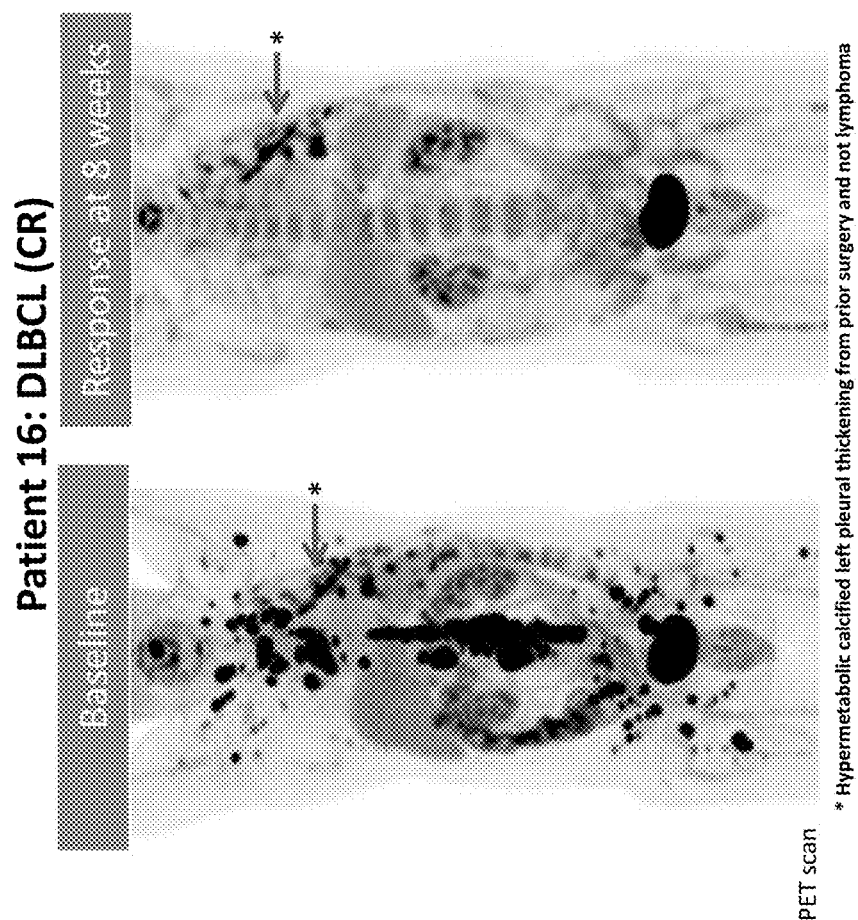
FIG. 6B shows an example of a 56 year old male with primary refractory DLBCL, 2 prior lines of therapy, bulky disease.

FIG. 6B shows an example of a 56 year old male with primary refractory DLBCL, 2 prior lines of therapy, bulky disease. A CR was achieved at 8 weeks.

NHL Subgroup Efficacy Analyses

Patient demographics (Table D) and efficacy analyses (Table E) are shown for all patients treated in the dose escalation Phase 1b part of the trial of Hu5F9-G4 in combination with rituximab in patients with relapsed/refractory B-cell non-Hodgkin's lymphoma (NHL) as of January 2018. Preliminary duration of response data is presented in Table F. Rituximab 375 mg/m² weekly dosing during cycle 1 and monthly from cycles 2-6 was utilized in combination with a 1 mg/kg priming dose of Hu5F9-G4 on day 1 and dose escalation of subsequent weekly Hu5F9-G4 maintenance doses from 10 mg/kg to 30 mg/kg. Both diffuse large B-cell lymphoma (DLBCL) and follicular lymphoma (FL) patients were enrolled in the Phase 1b part. While patients were at least relapsed or refractory to at least two prior lines of therapy, the patients enrolled generally represented a much more heavily pre-treated population in which the majority of patients were refractory to rituximab by two clinical definitions (Table D). In addition, many of the patients enrolled were in rapid need of therapy due to significantly progressive disease. Despite extensive pre-treatment and most being refractory to prior rituximab therapy, a significant proportion of patients experienced objective responses.

Figure 7:
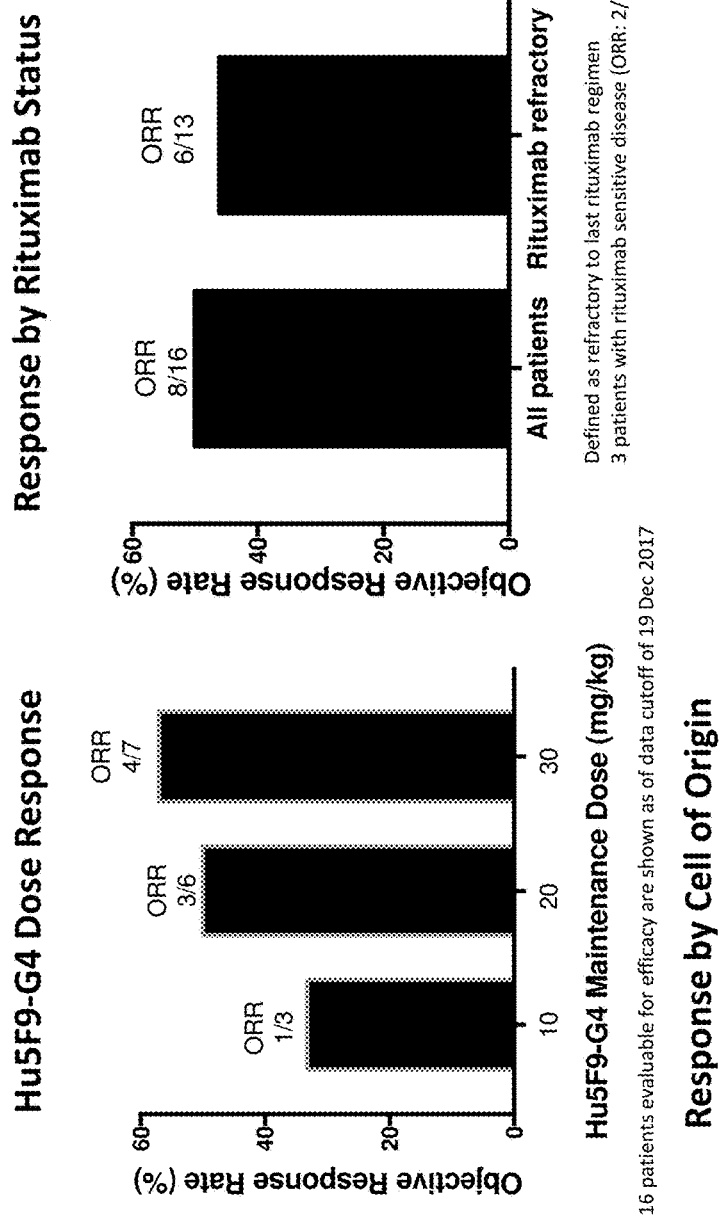
FIG. 7 shows an NHL Subgroup Efficacy Analyses.
Figure 7:
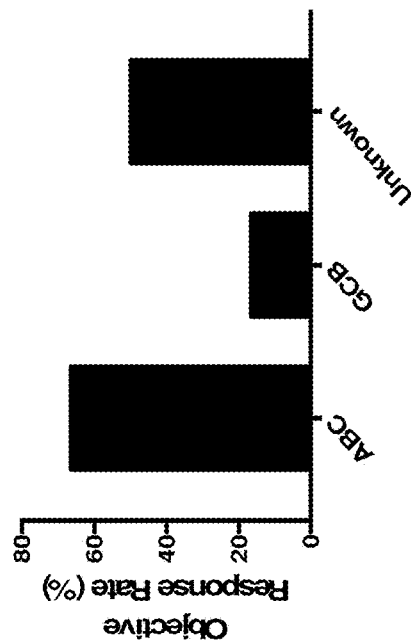

FIG. 7 shows an NHL Subgroup Efficacy Analyses.

Table E1: Efficacy data for evaluable patients in the Phase 1b dose escalation population as of January 2018.

TABLE E1

| Characteristic[5] | All Patients, n = 22 (%) | DLBCL, n = 15 (%) | FL, n = 7 (%) |
|---|---|---|---|
| ORR | 11 (50) | 6 (40) | 5 (71.4) |
| PR | 4 (18.1) | 2 (13.3) | 2 (28.6) |
| CR | 7 (31.8) | 4 (26.7) | 3 (42.8) |
| SD | 3 (13.6) | 3 (20) | 0 (0) |
| PD | 8 (36.4) | 6 (40) | 2 (28.6) |
| Disease control rate (PR + CR + SD) | 14 (63.6) | 9 (60) | 5 (71.4) |
| Rituximab-refractory-any regimen[1] | N = 20 | N = 14 | N = 6 |
| ORR | 10 (50) | 6 (42.9) | 4 (66.7) |
| PR | 4 (20) | 2 (14.3) | 2 (33.3) |
| CR | 6 (30) | 4 (28.6) | 2 (33.3) |
| SD | 3 (15) | 3 (21.4) | 0 (0) |
| Rituximab-refractory-last regimen[2] | N = 19 | N = 14 | N = 5 |
| ORR | 9 (47.4) | 6 (42.9) | 3 (60) |
| PR | 4 (21.1) | 2 (14.3) | 2 (40) |
| CR | 5 (26.3) | 4 (28.6) | 1 (20) |
| SD | 3 (15.8) | 3 (21.4) | 0 (0) |
| Refractory to last regimen[3] | N = 15 | N = 10 | N = 5 |
| ORR | 7 (46.7) | 4 (40) | 3 (60) |
| PR | 1 (6.7) | 1 (10) | 0 (0) |
| CR | 6 (40) | 3 (30) | 3 (60) |
| SD | 2 (13.3) | 2 (20) | 0 (0) |
| ORR by Cell of origin status, DLBCL (n) | n/a | | n/a |
| ABC (3) | | 2 (66.6) | |
| GCB (6) | | 1 (16.7) | |
| Unknown (6) | | 3 (50) | |
| Double hit lymphoma | N = 3 | N = 3 | N = 0 |
| ORR | 1 (33.3) | 1 33.3) | n/a |
| PR | 0 (0) | 0 (0) | |
| CR | 1 (33.3) | 1 (33.3) | |
| SD | 1 (33.3) | 1 (33.3) | |
| Prior autologous transplant | N = 5 | N = 2 | N = 3 |
| ORR | 5 (100) | 2 (100) | 3 (100) |
| PR | 2 (40) | 0 (0) | 2 (67.4) |
| CR | 3 (60) | 2 (100) | 1 (33.3) |
| SD | 0 (0) | 0 (0) | 0 (0) |
| ORR by Hu5F9-G4 dose level (n) | N = 22 | N = 15 | N = 7 |
| 10 mg/kg (3) | 1 (33.3) | 0 (0) | 1 (14.3) |
| 20 mg/kg (6) | 3 (50) | 3 (20) | 0 (0) |
| 30 mg/kg (13) | 7 (53.8) | 3 (20) | 4 (57.1) |

TABLE E2

Efficacy data for evaluable patients in the Phase 1b DLBCL subsets as of April 2018

| Characteristic | N (%) | Objective Response (%) |
|---|---|---|
| De novo DLBCL | 8 (53%) | 2/8 (25%) |
| Transformed DLBCL | 7 (47%) | 4/7 (57%) |
| Cell of Origin | | |
| Activated B-cell | 3 (20%) | 2/3 (67%) |
| Germinal Center B-cell | 6 (40%) | 1/6 (17%) |
| Unknown | 6 (40%) | 3/6 (50%) |
| Double hit lymphoma[1] | 3 (20%) | 1/3 (33%) |

TABLE F

Response Duration by Individual Patient.

| Subject # | Subject ID | Cancer Type | Hu5F9-G4 Dose Group (mg/kg) | Lugano Stage at Initial Diagnosis | Rituximab Refractory[1] | Number of Prior Cancer Therapies | Best Response | Duration of Response (months)[6] |
|---|---|---|---|---|---|---|---|---|
| 1 | 016-002 | DLBCL | 10 | Stage 4 | No | 2 | PD | |
| 2 | 020-001 | DLBCL | 10 | Stage 3 | Yes | 4 | PD | |
| 3 | 015-001 | DLBCL | 20 | Stage 3 | Yes | 3 | PD | |
| 4 | 015-002* | DLBCL | 20 | Stage 3 | Yes | 4 | CR | 2.4* |
| 5 | 016-003 | DLBCL | 20 | Stage 4 | Yes | 3 | PD | |
| 6 | 016-004 | DLBCL | 20 | Stage 2 | Yes | 6 | SD | |
| 7 | 019-001 | DLBCL | 20 | Stage 4 | Yes | 5 | PR | 3.9 |
| 8 | 020-002 | DLBCL | 20 | Stage 4 | Yes | 4 | CR | 3.3+ |
| 9 | 015-003 | DLBCL | 30 | Stage 4 | Yes | 5 | PD | |
| 10 | 015-004 | DLBCL | 30 | Stage 2 | Yes | 7 | PD | |
| 11 | 015-005 | DLBCL | 30 | Stage 4 | Yes | 6 | SD | |
| 12 | 019-003 | DLBCL | 30 | Stage 4 | Yes | 6 | PR | 1.3+ |
| 13 | 020-003 | DLBCL | 30 | Unknown | Yes | 9 | CR | 1.6+ |
| 14 | 024-004 | DLBCL | 30 | Stage 4 | Yes | 2 | SD | |
| 15 | 027-003 | DLBCL | 30 | Stage 2 | Yes | 2 | CR | 1.6+ |
| 16 | 016-001 | FL | 10 | Stage 3 | No | 4 | CR | 12.0+ |
| 17 | 019-002 | FL | 30 | Stage 4 | Yes | 3 | CR | 3.6+ |
| 18 | 019-004 | FL | 30 | Stage 4 | Yes | 4 | CR | 1.1+ |
| 19 | 023-001 | FL | 30 | Stage 2 | Yes | 5 | PD | |
| 20 | 024-003 | FL | 30 | Stage 3 | Yes | 2 | PD | |
| 21 | 027-001 | FL | 30 | Unknown | Yes | 7 | PR | 4.6+ |
| 22 | 027-002 | FL | 30 | Unknown | Yes | 9 | PR | 1.5+ |

[1]Rituximab-refractory—any regimen: defined as failure to respond to, or progression during, any previous rituximab-containing regimen (monotherapy or combined with chemotherapy), or progression within 6 months of the last rituximab dose (Sehn et al. Lancet Oncol: GADOLIN trial 2016).
[2]Rituximab-refractory—last regimen: defined as failure to respond to, or progression during, last previous rituximab-containing regimen (monotherapy or combined with chemotherapy), or progression within 6 months of the last rituximab dose.
[3]Refractory to last regimen: defined as failure to respond to, or progression during, last prior regimen, or progression within 6 months of the last treatment dose. Patients discontinuing last prior therapy due to toxicity are not counted as refractory to last regimen.
[4]Double hit lymphoma defined as high-grade B-cell lymphomas with MYC and BCL2 and/or BCL6 rearrangements per WHO classification for lymphoid neoplasms (Swerdlow et al., Blood 2016).
[5]Best response is shown
[6]Duration of response is defined as time from initial documented objective response to time of documented progression or data cutoff date of 22 January 2018 if no evidence of progression
*Patient proceeded to allogeneic stem cell transplant in CR, response duration censored at end of study visit
+Signifies response ongoing at time of data cutoff A positive dose response correlation was observed with efficacy. Efficacy in rituximab-refractory patients was found to be similar to all patients. Efficacy has been observed in both ABC, GCB, and double hit lymphoma DLBCL subtypes.

In the trial, higher objective response rates have been observed in transformed DLBCL patients (4/7, 57%) compared to de novo (non-transformed) DLBCL patients (2/8, 25%) (FIG. 10). Patients with transformed DLBCL have a preceding indolent lymphoma (i.e. follicular lymphoma, marginal zone lymphoma or small lymphocytic lymphoma) that then transforms to an aggressive DLBCL phenotype. Often transformed DLBCL patients have a mixture of indolent and aggressive B cell lymphoma features. The increased objective responses seen in transformed DLBCL may be due to the ability of 5F9+rituximab to more effectively eliminate indolent disease, as initial response rates in FL were 71% (FIG. 4B).

Summary and Conclusions

Twenty-two patients with relapsed/refractory DLBCL or FL were enrolled across 3 dose cohorts between November 2016 and October 2017. Data are presented through April 2018. 5F9 was well-tolerated in combination with rituximab with no MTD achieved to-date. On target anemia was transient and significantly mitigated by use of a prime/ maintenance dosing regimen. Anti-tumor activity was observed with 33% and 43% CR rates in DLBCL and FL, respectively, as of April 2018. Median duration of response not reached with 6.2-8.1 month follow-up.

Baseline patient characteristics included a median age of 59 years (range 44-82 years), 21 patients (95%) with an ECOG performance status of 0 or 1, and 4 (18%) with a prior autologous stem cell transplant. The median number of prior lines of therapy was 4 (range 2-10), with 21 (95%) patients having tumors refractory to prior rituximab, and 14 (64%) patients having tumors refractory to their last treatment regimen. DLBCL patients with diverse DLBCL molecular phenotypes were enrolled.

The median treatment duration was 22 weeks (range 1.7 to 71.1 weeks and ongoing). All 22 patients received 5F9 and rituximab with one patient not evaluable for efficacy due to study drug discontinuation from an adverse event (idiopathic thrombocytopenic purpura) at approximately 2 weeks. This patient was added to the denominator (as a non-responder) in the efficacy assessment. Overall, three patients died, all due to disease progression with an all-cause mortality of 14%.

Safety

The majority of treatment-emergent adverse events were Grade 1 and 2. The most common treatment-related adverse events were chills (41%), headache (41%), anemia (41%), and infusion-related reactions (36%) (FIG. S3A). The majority of treatment-related adverse events occurred within the first few weeks with no long-term toxicities observed. Serious adverse events are described above. Three dose-limiting toxicities were observed. In cohort 2, a grade 3 pulmonary embolism was seen. This patient experienced respiratory symptoms during a 5F9 infusion and was later found to have an occult deep venous thrombosis as a result of vascular compression from lymphoma that was likely the source of the pulmonary embolism. The patient was treated with anticoagulation with symptom resolution and continued on treatment until disease progression several weeks later. This toxicity led to cohort expansion to 6 patients, with no additional dose limiting toxicities observed. Cohort 3 initially enrolled 6 patients with no dose-limiting toxicities observed. This cohort was expanded to 13 patients to collect additional PK and pharmacodynamic data. Two additional patients had a dose-limiting toxicity: one grade 4 neutropenia and one grade 3 idiopathic thrombocytopenia purpura. The patient with grade 4 neutropenia resolved with G-CSF support and continued on study with complete resolution of neutropenia without further growth factor support. The patient with grade 3 idiopathic thrombocytopenic purpura discontinued treatment and received glucocorticoid and intravenous immunoglobulin treatment with resolution of the thrombocytopenia. The dose-limiting toxicity frequency for cohort 3 was 15%, below the 33% rate that would exceed the maximum tolerated dose threshold. Thus, no maximum tolerated dose was reached. The 30 mg/kg 5F9 maintenance dose in combination with rituximab and was established as a recommended Phase 2 dose for further study based on pharmacokinetic data and pharmacodynamic data documenting saturation of CD47 binding on circulating cells.

Anemia is an expected on-target pharmacodynamic effect of blocking CD47. CD47 blockade can accelerate elimination of aged red blood cells (RBCs), secondary to unmasking pro-phagocytic signals on aged RBCs. As RBCs age, they lose CD47 expression and gain expression of pro-phagocytic signals leading to homeostatic clearance (Oldenborg P A, Zheleznyak A, Fang Y F, Lagenaur C F, Gresham H D, Lindberg F P. Role of CD47 as a marker of self on red blood cells. Science 2000; 288:2051-4.). To mitigate this on-target anemia, a priming dose of 1 mg/kg of 5F9 was administered to selectively eliminate aged RBCs while sparing younger RBCs, which lack pro-phagocytic signals. This priming dose led to a transient mild anemia followed by a compensatory reticulocytosis that shifted the age of RBCs from old to young RBCs. Subsequent higher maintenance doses could then be administered with anemia resolution without recurrence. This priming/maintenance dose strategy substantially mitigated on-target anemia based on seminal studies of 5F9 in non-human primates (Liu J, Wang L, Zhao F, et al. Pre-Clinical Development of a Humanized Anti-CD47 Antibody with Anti-Cancer Therapeutic Potential. PLoS One 2015; 10:e0137345.). In support of this observation, treatment-related anemia observed in the lymphoma patients was mainly grade 1 and 2 and occurred primarily in the first week. Minimal evidence of hemolysis was observed, with a mild and transient rise in indirect bilirubin correlating with the initial transient anemia. A transient decrease in haptoglobin below normal range was observed in 3/22 (14%) of patients that normalized after the first two weeks of treatment. The average pre-treatment hemoglobin was 12.1 g/dL. The average hemoglobin drop across all 5F9 doses was 0.91 g/dL (maximum drop of 2.4 g/dL). Three patients required RBC transfusions while on study; 2 patients received only 1 transfusion (2 units) while the third received 4 transfusions (8 units). All transfusions were successfully administered with the expected increase in hemoglobin post-transfusion.

Pharmacokinetics, Pharmacodynamics and Anti-Drug Antibodies

At doses of 10 to 30 mg/kg, dose proportional pharmacokinetic profiles were observed after the fourth maintenance dose, indicating saturation of the CD47 antigen sink. Once saturation was achieved, the apparent terminal half-life of 5F9 was approximately 13 days. Serum samples from one subject (4.5%) at baseline and after start of 5F9 treatment tested positive for anti-5F9 antibodies. There was no impact on pharmacokinetics in this patient. CD47 receptor occupancy was measured as a pharmacodynamic endpoint. With a 1 mg/kg 5F9 priming dose followed by 30 mg/kg maintenance dosing, near 100% CD47 receptor occupancy was observed on circulating RBCs and WBCs. 5F9 antibody tumor penetrance was observed in a DLBCL patient treated with 5F9.

Efficacy

In an intent-to-treat analysis, the overall response rate for all patients was 50%, with 36% achieving a complete response. In DLBCL, the response rate was 6/15 (40%) with 5/15 (33%) achieving a complete response. In FL, the response rate was 5/7 (71%) with 3/7 (43%) achieving complete response. Median time to response was 1.7 months (range 1.6-6.6 months). Median duration of response was not reached for either DLBCL or FL patients with a median follow-up of 6.2 and 8.1 months, respectively. Ten of 11 (91%) responding patients have maintained responses ongoing at time of data-cut off. One heavily pre-treated DLBCL patient who relapsed within 3 months of autologous stem cell transplant with bulky disease and marrow infiltration achieved a complete response on study. This patient then proceeded to an allogeneic stem cell transplant with a matched related donor and continued in complete response over 7 months ongoing at time of data cut-off. Two DLBCL patients on study improved their responses on therapy over time. One patient improved from stable disease to a complete response at month 6 and another patient improved from a partial response at 2 months to a complete response at month 4. Both patients continued in complete response at time of data cut-off. Complete responses were also seen in patients with bulky disease. Responses have also been observed across multiple DLBCL subtypes.

Conclusions

22 [15 diffuse large B-cell lymphoma (DLBCL) and 7 follicular lymphoma (FL)] patients enrolled with a median of 4 prior therapies (range 2-10); 95% were rituximab refractory. Adverse events were predominantly grade ½. Most common adverse events were anemia and infusion reactions. Anemia (an expected on-target effect) was mitigated by 5F9 prime/maintenance dosing. No dose-limiting side effects were observed. A selected phase 2 5F9 dose of 30 mg/kg achieved ~100% CD47 receptor occupancy on circulating white and red blood cells. Fifty percent of patients had an objective response with 36% complete responses. Responses/complete responses were 40%/33% in DLBCL and 71%/43% in FL. At a median follow-up time of 6.2 months for DLBCL and 8.1 months for FL, 91% of the responses are ongoing.

Phase 2 Dosing Regimen

Figure 8:
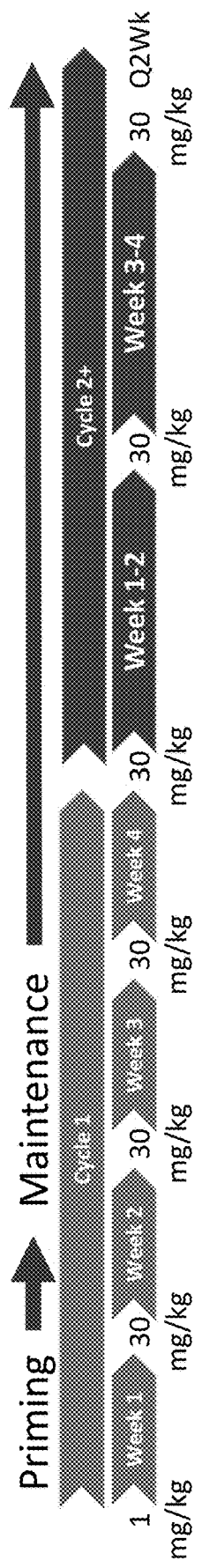
FIG. 8 shows the phase 2 dose set for clinical trial.

FIG. 8 shows the phase 2 dose set for clinical trial.

Proprietary priming dose strategy mitigates on-target red blood cell effects.

Cycle 1, weekly: rapidly saturates antigen sink.

Cycle 2 and beyond, every 2 weeks.

Example 3: Anti-CD47 Antibody Enhances Tumor Cell Phagocytosis In Vitro when Combined with Rituximab in a Rituximab-Resistant Lymphoma Cell Line Combination of Hu5F9-G4 and rituximab has a unique MOA of phagocytic synergy through simultaneous blockade of the anti-phagocytic CD47 signal with enhancement of a pro-phagocytic signal via antibody-dependent cellular phagocytosis by rituximab's Fc receptor. In preclinical models, this novel MOA has led to anti-tumor efficacy in rituximab-refractory/resistant settings.

Mouse bone marrow-derived macrophages were incubated with the indicated antibodies in the presence of rituximab sensitive or resistant Raji lymphoma cells. Rituximab induced significantly lower phagocytosis in the resistant compared to sensitive cell line. However, anti-CD47+ rituximab induced robust phagocytosis in both rituximab sensitive and resistant settings. Raji cells were serially cultured with rituximab and macrophages over multiple passages to select out clones resistant to rituximab.

Figure 9:
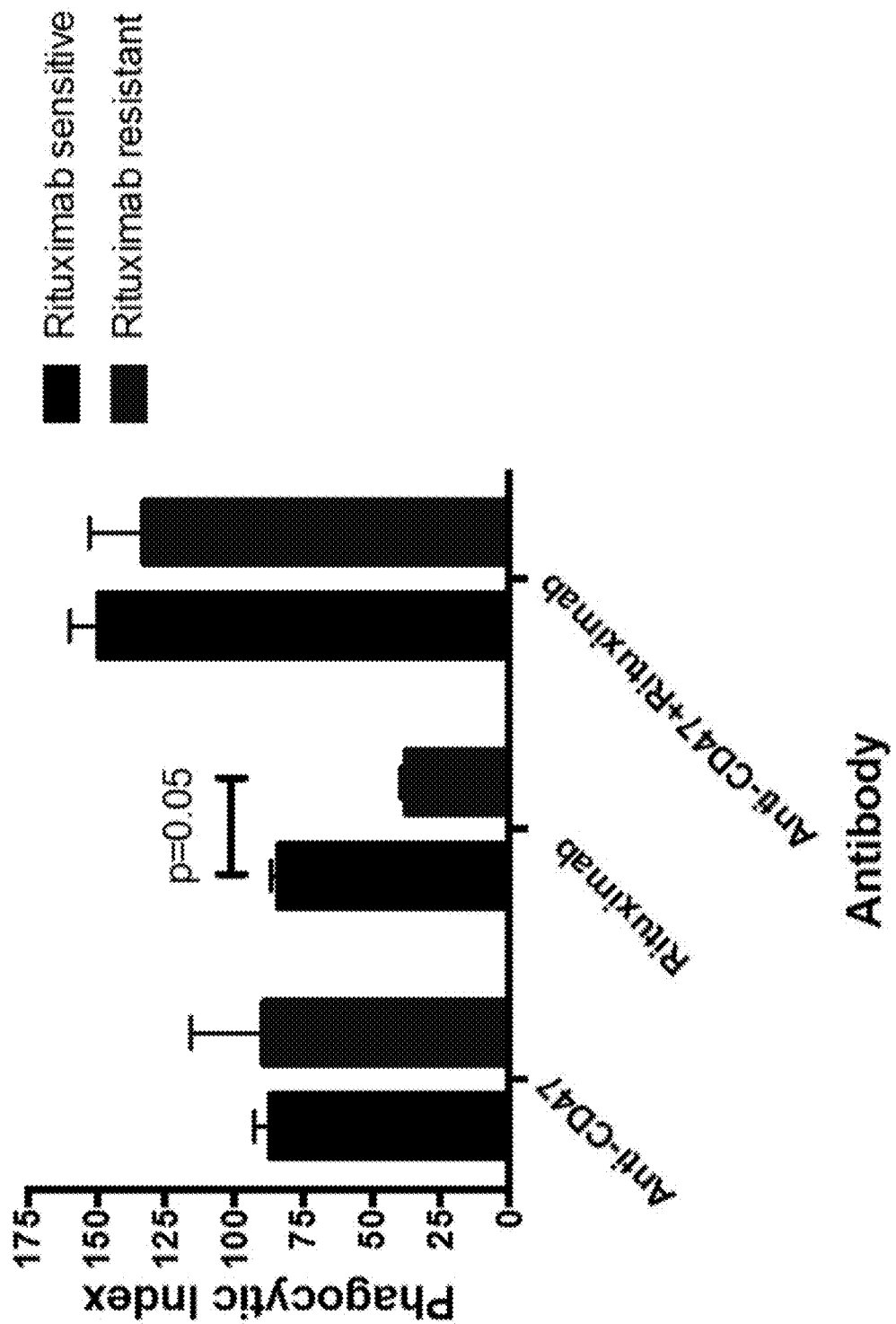
FIG. 9 shows that anti-CD47 antibody enhanced tumor cell phagocytosis in vitro when combined with rituximab in a rituximab-resistant lymphoma cell line. The left bar of each group is rituximab sensitive; the right bar of each group is rituximab resistant.

The anti-CD47 antibody+rituximab combination led to enhanced phagocytosis in vitro in a lymphoma cell line that was resistant to rituximab (FIG. 9). Combination activity with anti-CD47 antibody+rituximab was still observed in the resistant cell line similar to the sensitive cell line.

These data support the scientific rationale for the efficacy of Hu5F9-G4+rituximab in rituximab refractory NHL patients.

Figure 12:
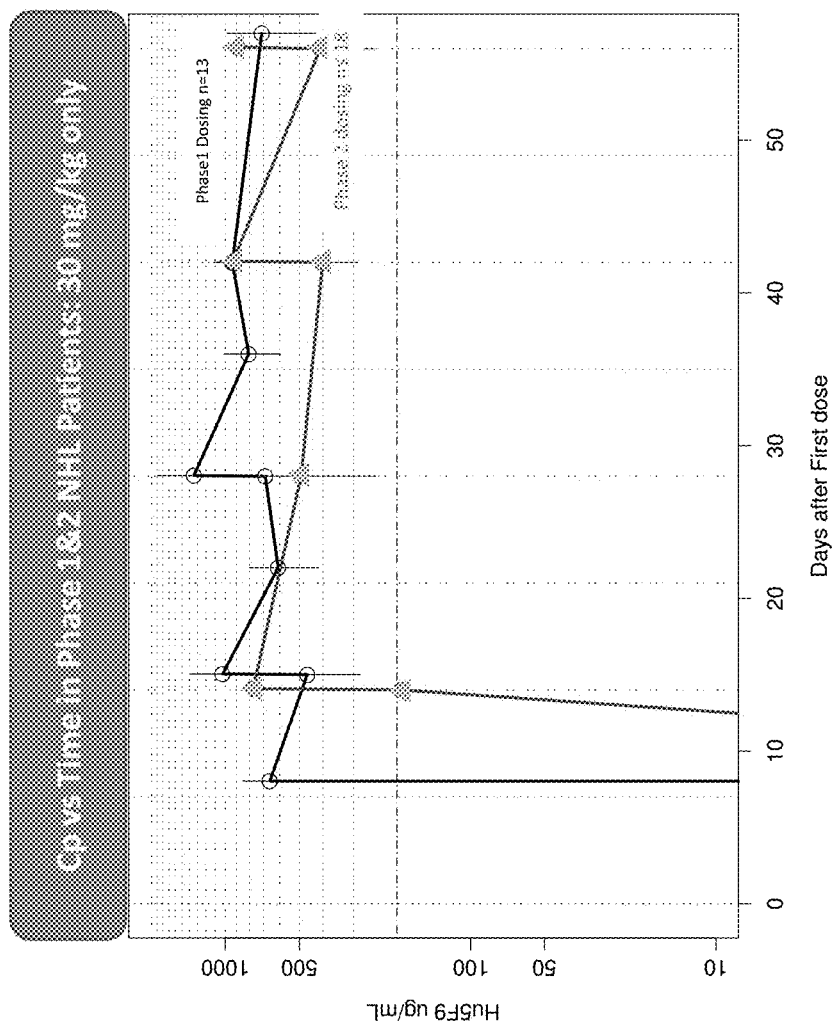
FIG. 12 shows that 5F9 concentrations are higher with weekly dosing vs. Q2 week dosing.

Example 4: Utilization of a 30 or 45 mg/kg Hu5F9-G4 Dose in a Priming, Loading, Maintenance Dose Strategy in Combination with Rituximab for Treating NHL Patients CD47 is expressed on a majority of normal tissues and thus CD47 represents a large tissue antigen sink. Therefore, high doses of Hu5F9-G4 are used to overcome this normal antigen sink and lead to antibody penetration into the tumor to achieve anti-cancer efficacy. To overcome this challenge, Hu5F9-G4 has been dosed in a priming, loading and maintenance dose schedule, whereby an initial low (priming) dose is given to mitigate on target anemia, followed by a maintenance dose with an additional loading dose in week 2, and continued weekly maintenance dosing through cycle 2 (Table G). Hu5F9-G4 is then dosed Q2 weeks starting Cycle 3 and beyond. The weekly maintenance with an additional loading dose paradigm is designed to rapidly saturate the CD47 normal antigen sink, leading to antibody tumor penetration, whereby linear pharmacokinetics are observed after saturation. Indeed, weekly 5F9 dosing with an additional week 2 loading dose for the first 2 cycles (months) led to higher 5F9 concentrations compared to weekly 5F9 dosing only in the first cycle (FIG. 12). In addition to achieving saturating drug concentrations rapidly, higher doses of 5F9 may also enhance therapeutic efficacy. In the Phase 1b trial described above, a positive dose response with efficacy was observed in 5F9 doses ranging from 10, 20, and 30 mg/kg without achieving a plateau. Therefore, doses higher than 30 mg/kg may lead to enhanced efficacy. Based on this finding, 5F9 is tested in a 45 mg/kg dosing regimen (Table G), in addition to a 30 mg/kg dosing regimen, and demonstrates efficacy.

TABLE G

5F9 + rituximab dosing regimens in NHL patients

| Drug/Dose (IV) | Cycle 1 | Cycle 2 | Cycle 3-5 | Cycle 6+ |
| --- | --- | --- | --- | --- |
| Hu5F9-G4 1 mg/kg (prime) | Day 1 | — | — | — |
| Hu5F9-G4 30 or 45 mg/kg (maintenance) | Day 8, 11, 15, 22 | Day 1, 8, 15, 22 | Day 1, 15 | Day 1, 15 |
| Rituximab 375 mg/m$^2$ | Day 8, 15, 22 | Day 1 | Day 1 | Day 1 of Cycle 6, Day 1 every other Cycle Starting Cycle 8 |

Abbreviations: IV = intravenous.

Example 5: CD47 Expression-Based Patient Selection

DLBCL patients can be subdivided into cell of origin categories based on gene expression patterns of germinal center B cells (GCB) and activated B cells (ABC), which have led to significant prognostic and therapeutic implications. In a small sample size in the above Phase 1b/2 trial, 2 out of 3 (67%) of DLBCL patients with the ABC phenotype had objective responses, whereas 1 of 6 (17%) of GCB patients had responses (FIG. 10). This difference in clinical responses may enable an efficacy enrichment of patients with the ABC phenotype or by excluding GCB patients.

Figure 11:
FIG. 11 shows CD47 expression in tonsil. A normal healthy patient tonsil was stained with an anti-human CD47 antibody by immunohistochemistry. Dark staining denotes positive CD47 staining. Low magnification (left) and high magnification (right) is shown with arrows notating sample areas that are absent CD47 expression, which represent germinal centers.
Figure 11:

CD47 expression level may be a determinant in a potential differential efficacy between ABC and GCB patients. Interestingly, when a normal healthy patient tonsil was stained for human CD47 expression, germinal centers were negative for CD47 expression (FIG. 11). These observations suggest that GCB DLBCL patients may have lower, relative efficacy with 5F9 due to absent or decreased CD47 expression. This finding suggests that clinical efficacy of 5F9 (+/−rituximab) can be increased through evaluating CD47 expression in lymphoma tissues.

Figure 13:
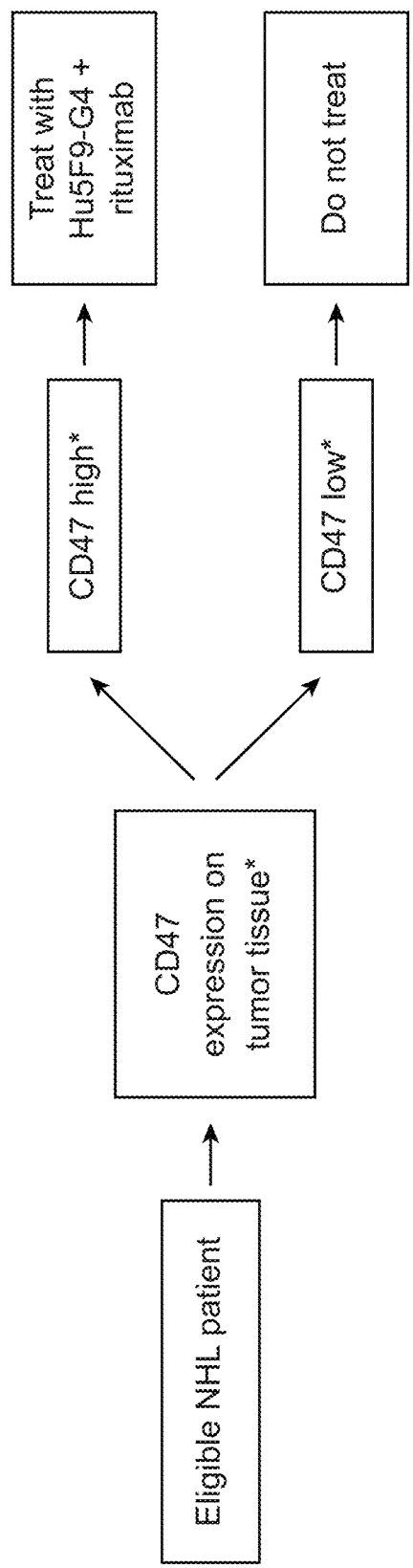
FIG. 13 shows a design schema for use of CD47 expression as a patient selection strategy for Hu5F9-G4+/−rituximab treatment in NHL patients. Exemplary method: *High CD47 expression can be scored as follows: 1) A score of 2+ or +3 on a scale of 0-3+, whereas 0 represents absent CD47 staining with 3+ representing maximal CD47 staining; 2) or using an H score, a semiquantitative score whereby CD47 membrane staining intensity (0, 1+, 2+, or 3+) is determined for each cell in a fixed field. The percentage of cells at each staining intensity level is calculated and an H-score is assigned using the following formula: [1×(% cells 1+)+ 2×(% cells 2+)+3×(% cells 3+)]. A similar method for deriving the H score may be used. A high H score cut-off would be utilized for high CD47 expression. Low CD47 expression can be scored with 1) a score of 0 or 1+; or 2) using an H score, whereby a low H-score cut-off is utilized for low CD47 expression.

FIG. 13 shows a design schema for use of CD47 expression as a patient selection strategy for Hu5F9-G4+/−rituximab treatment in NHL patients.

Example 6: 5F9+ Venetoclax+/−Rituximab Therapeutic Combination in B-Cell NHL Patients The Bcl-2 family of proteins are key mediators of the apoptotic pathway. The specific protein, Bcl-2, is an antiapoptotic protein that promotes cell survival. Several NHL subtypes frequently overexpress Bcl-2 in multiple manners (translocation involving BCL2, chromosome 18q21 amplification, and alterations in microRNAs that regulate Bcl-2 expression). Overexpression of Bcl-2 in these lymphomas leads to increased cell proliferation. Multiple agents are being developed to inhibit Bcl-2 function, thereby leading to apoptosis and cell death of lymphoma cells. For example, venetoclax, an FDA-approved oral Bcl-2 inhibitor, restores apoptosis by binding directly to the Bcl-2 protein and triggering caspase activation. Given that Bcl-2 inhibitors such as venetoclax and navitoclax, induce apoptosis, these agents may also induce pro-phagocytic signals leading to apoptosis. In this light, CD47 blockade may synergize with Bcl-2 inhibition through induction of pro-phagocytic signals on lymphoma cells coupled with blockade of the anti-phagocytic signal CD47. These complementary mechanisms would then lead to enhanced phagocytosis when CD47 blockade is combined with Bcl-2 inhibition. For example, the combination of 5F9 with venetoclax could lead to enhanced anti-lymphoma activity in NHL patients compared to either agent alone. In addition, a triplet combination of 5F9 with an anti-CD20 antibody and venetoclax also has potential enhanced efficacy through the delivery of pro-phagocytic signals on lymphoma cells in two ways: induction by Bcl-2 inhibition and delivery of an external pro-phagocytic signal by rituximab through Fc receptor engagement. In addition, clinical activity with 5F9+rituximab and venetoclax+rituximab in NHL patients. For 5F9+rituximab, a 50% ORR was observed in a Phase 1b trial of combined DLBCL and FL patients. For rituximab+venetoclax, an 86% ORR in chronic lymphocytic leukemia patients (Seymour J F, Kipps T J, Eichhorst B, et al. Venetoclax-Rituximab in Relapsed or Refractory Chronic Lymphocytic Leukemia. N Engl J Med 2018; 378:1107-20) and 33% ORR in FL patients (Zinzani P L T M, Yuen S, Rusconi C, Fleury I, Pro B, Gritti G, Crump M, Hsu W, Punnoose E, Hilger J, Mobasher M, Hiddermann W. Phase 2 Study of Venetoclax Plus Rituximab or Randomized Ven Plus Bendamustine+Rituximab (BR) Versus BR in Patients with Relapsed/Refractory Follicular Lymphoma: Interim Data. Blood ASH abstract 2016; 128:617.) was observed. The combination of the clinical data and scientific rationale leads to a strong rationale for the doublet combination of 5F9+venetoclax or the triplet combination of 5F9+venetoclax+rituximab.

The molecular formula of venetoclax is $C_{45}H_{50}ClN_7O_7S$. Exemplary treatment regimen(s) are as follows:

1. Venetoclax 20 mg PO for 7 days, followed by a weekly ramp-up dosing schedule to the recommended daily dose of 400 mg
2. Venetoclax 20 mg PO×1 weeks, 50 mg PO×1 week, 100 mg PO×1 week, then 200 mg PO×1 week, and continued 200 mg daily dosing
3. Venetoclax 20 mg PO×1 weeks, 50 mg PO×1 week, 100 mg PO×1 week, then 200 mg PO×1 week, 400 mg PO×1 week, then 400 mg weekly dosing
4. Venetoclax 50 mg PO×1 weeks, 100 mg PO×1 week, 200 mg PO×1 week, then 400 mg PO×1 week, and continued 400 mg daily dosing
5. Venetoclax 100 mg PO×1 weeks, 200 mg PO×1 week, 400 mg PO×1 week, then 800 mg PO×1 week, and continued 800 mg daily dosing Example 7: Hu5F9-G4 in Combination with Rituximab and Atezolizumab in Patients with Relapsed/Refractory B-Cell Non-Hodgkin's Lymphoma Below is a protocol for assessing Hu5F9-G4 in Combination with Rituximab and Atezolizumab in Patients with Relapsed/Refractory B-cell Non-Hodgkin's Lymphoma.

Concept and Rationale:

Non-Hodgkin's lymphoma (NHL) is among the most common cancers in the USA and Europe, with more than 70,000 and 93,000 new cases diagnosed every year, respectively (Ferlay J, Soerjomataram I, Dikshit R, et al. Cancer incidence and mortality worldwide: sources, methods and major patterns in GLOBOCAN 2012. International journal of cancer Journal international du cancer 2015;136:E359-86). Diffuse large B-cell lymphoma (DLBCL) is an aggressive subtype of NHL with high relapse rate and poor long-term survival. In addition, few treatment options are available to patients with indolent lymphoma who have relapsed or are refractory to rituximab. Novel and effective therapies are needed to address these high unmet medical needs.

Hu5F9-G4 is a monoclonal antibody that targets CD47, an anti-phagocytic cell surface protein that serves as a macrophage checkpoint. Nonclinical studies have demonstrated that blockade of CD47 signaling through this antibody eliminates human tumor cells including NHL, through facilitating phagocytosis by macrophages. Additional nonclinical studies demonstrate that anti-CD47 antibodies can synergize with Fc receptor-activating anti-cancer antibodies including rituximab by providing a potent pro-phagocytic signal leading to antibody-dependent cellular phagocytosis (ADCP). Combination therapy with Hu5F9-G4 and rituximab, an anti-CD20 monoclonal antibody, demonstrated a synergistic antitumor response compared to either agent alone in nonclinical models of NHL. A Phase 1b/2 trial of Hu5F9-G4 and rituximab in relapsed/refractory DLBCL patients has been well-tolerated and shown encouraging clinical activity. In a Phase 1b dose escalation cohort, 40% (6/15) of heavily pre-treated DLBCL patients achieved an objective response, including 33% achieving a CR (Advani R FI, Popplewell L, Forero A, Bartlett N, Ghosh N, Kline J, Tran T, Lynn J, Chen J, Agoram B, Huang J, Takimoto C, Chao MP, Smith S. Activity and tolerabilty of the first-in-class anti-CD47 antibody Hu5F9-G4 with rituximab tolerated in relapsed/refractory non-Hodgkin lymphoma: Initial phase 1b/2 results. J Clin Oncol 2018;36:suppl; abstr 7504).

The clinical activity of Hu5F9-G4 and rituximab can be further enhanced through the addition of T-cell checkpoint inhibitors, such as atezolizumab. This therapeutic enhancement is supported by three lines of evidence. First, Hu5F9-G4 can enable activation of an anti-tumor T cell response through macrophage-mediated cross presentation of tumor antigens to T cells (Tseng D, Volkmer JP, Willingham SB, et al. Anti-CD47 antibody-mediated phagocytosis of cancer by macrophages primes an effective antitumor T-cell response. Proc Natl Acad Sci U S A 2013;110:11103-8.). This anti-tumor T cell effect can be further augmented through the blockade of PD-L1/PD-1 through avelumab. Second, recent data has shown that a significant subset of DLBCL patients treated with rituximab had high PD-L1 expression on myeloid immune cells (McCord R BC, Koeppen H, Kadel E, Fingerle-Rowson G, Oestergaard M, Venstrom J. High Expression of Programmed Death-Ligand 1 (PD-L1) Correlates with Macrophage Gene Expression and Is Associated with Prolonged Progression-Free Survival (PFS) in Patients (pts) with First-Line (1L) Diffuse Large B-Cell Lymphoma (DLBCL). American Society of Hematology Annual Meeting Abstracts 2017), potentially reflecting exhausted macrophages that can be primed for ADCP by additional therapeutic agents such as PD-L1/PD-1 blockade by atezolizumab and CD47 blockade by Hu5F9-G4. Third, PD-1 expression on macrophages has been shown to be an additional anti-phagocytic signal that be therapeutically targeted by PD-1/PD-L1 inhibitors in combination with Hu5F9-G4 (Gordon SR, Maute RL, Dulken BW, et al. PD-1 expression by tumour-associated macrophages inhibits phagocytosis and tumour immunity. Nature 2017;545:495-9). Based on these three lines of data, the combination of rituximab with PD-L1 blockade by atezolizumab and Hu5F9-G4 that enables ADCP can lead to enhanced tumor phagocytosis by macrophages through multiple modalities leading to potential enhanced clinical benefit.

It is anticipated that the triplet combination of Hu5F9-G4, rituximab and atezolizumab has potential enhanced clinical activity in DLBCL. The addition of atezolizumab to Hu5F9-G4 and rituximab is expected to be well-tolerated. While atezolizumab has well-documented and manageable immune-mediated toxicities, Hu5F9-G4 and rituximab have no significant immune-mediated toxicities with no anticipated overlapping toxicities. In addition, both doublets of Hu5F9-G4+rituximab and atezolizumab+anti-CD20 antibodies have been well-tolerated in DLBCL patients. This clinical trial will evaluate the safety and initial efficacy of the triplet combination of Hu5F9-G4 + rituximab + atezolizumab in relapsed/refractory DLBCL patients.

Patient Eligibility:

Inclusion Criteria:

- Adults ≥ 18 years
- Safety Run-in Cohort: B-cell NHL expressing CD20 by immunohistochemistry (IHC) or flow cytometry, relapsed or refractory to at least one prior regimen systemic therapy
- DLBCL Cohort: De novo or transformed diffuse large B-cell lymphoma, not otherwise specified, primary mediastinal large B-cell lymphoma, high-grade B-cell lymphoma with MYC and BCL2 and/or BCL6 rearrangements, primary cutaneous DLBCL-leg type, according to the World Health Organization 2016 classification of lymphoid neoplasms (Swerdlow 2016), relapsed or refractory to at least one prior systemic therapy
- Eastern Cooperative Oncology Group (ECOG) score 0-2
- Disease that is measurable or assessable for response per Lugano classification for lymphomas
- Laboratory measurements, blood counts:
  - Hemoglobin > 9.5 g/dL
  - Absolute neutrophil count (ANC) > $1.0 \times 10^9$/mL
  - Platelets > $75 \times 10^9$/mL
- Laboratory measurements, hepatic function:
  - Aspartate aminotransferase (AST)/alanine aminotransferase (ALT) < 5x upper limit of normal (ULN)
  - Bilirubin < 1.5x or 3.0x ULN and primarily unconjugated if patient has a documented history of Gilbert's syndrome or a genetic equivalent
- Laboratory measurements, renal function:
  - Serum creatinine < 1.5x ULN or calculated glomerular filtration rate (GFR) < 40 mL/min/1.73 $m^2$
- Negative urine or serum pregnancy test within 30 days before administration of Hu5F9-G4 for women of childbearing potential
- Females of childbearing potential must be willing to use 2 effective methods of contraception during and for 12 months after the last dose of rituximab or 4 months after the last dose of Hu5F9, whichever occurs later
- Males must be willing to use 1 highly effective method of contraception during and for 12 months after the last dose of rituximab or 4 months after the last dose of Hu5F9, whichever occurs later, if the partner is a female of childbearing potential
- Subject has provided informed consent
- Must be willing and able to comply with clinic visits and procedures outlined in the study protocol
- Willing to consent to 1 mandatory pre-treatment and 1 on-treatment tumor biopsy, unless not feasible as determined by the Investigator (reasons include but are not limited to lack of accessible tumor tissue to biopsy and patient safety issues)

Exclusion Criteria:

- Patients with active brain metastases (patients with stable treated central nervous system [CNS] lesions who are off corticosteroid therapy for at least 3 weeks are not considered active)
- Prior allogeneic hematopoietic cell transplantation (autologous transplant permitted)
- Prior anticancer therapy including chemotherapy, hormonal therapy, or investigational agents within 2 weeks or within at least 4 half-lives prior to Hu5F9-G4 dosing (up to a maximum of 4 weeks), whichever is longer. Low dose steroids (oral prednisone or its equivalent ≤ 10 mg per day) and localized non-CNS radiotherapy are not criteria for exclusion
- Known active or chronic hepatitis B or C infection or human immunodeficiency virus (HIV)
- Red blood cell (RBC) transfusion dependence, defined as requiring more than 2 units of RBC transfusions during the 4-week period prior to screening. RBC transfusions are permitted during screening and prior to enrollment to meet the hemoglobin inclusion criteria.

- History of hemolytic anemia or Evans syndrome in the last 3 months
- Prior treatment with CD47 or signal regulatory protein alpha (SIRPα) targeting agents
- Prior treatment with T-cell checkpoint inhibitor agents
- History of idiopathic pulmonary fibrosis, organizing pneumonitis (e.g., bronchiolitis obliterans), drug-induced pneumonitis, or idiopathic pneumonitis
- History of autoimmune disease
  Patients with a history of autoimmune-related hypothyroidism receiving a stable dose of thyroid replacement may be eligible for this study.
  Patients with controlled Type 1 diabetes mellitus receiving a stable insulin regimen may be eligible for this study.
  Patients with eczema, psoriasis, lichen simplex chronicus, or vitiligo with dermatologic manifestations only (e.g., patients with psoriatic arthritis are excluded) are eligible for the study provided all of the following conditions are met:
  – Rash must cover < 10% of body surface area.
  – Disease is well controlled at baseline and requires only low-potency topical corticosteroids.
  No occurrence of acute exacerbations of the underlying condition that require psoralen plus ultraviolet A radiation, methotrexate, retinoids, biologic agents, oral calcineurin inhibitors, or high-potency or oral corticosteroids within the previous 12 months.
- Immunosuppressive therapy (including, but not limited to, azathioprine, mycophenolate mofetil, cyclosporine, tacrolimus, methotrexate, and anti-tumor necrosis factor [anti-TNF] agents) within 6 weeks of Day 1 of Cycle 1
- Daily requirement for corticosteroids (> 10 mg prednisone daily or equivalent, except for inhalation corticosteroids) within 2 weeks prior to Day 1 of Cycle 1
- Treatment with systemic immunostimulatory agents (including, but not limited to, interferon [IFN]-α and interleukin [IL]-2) within 4 weeks or 5 half-lives of the drug, whichever is longer, prior to Day 1 of Cycle 1
- Treatment with denosumab (or other RANKL inhibitor) 4 weeks before the first dose and for 10 weeks after the last dose of atezolizumab
  Patients receiving denosumab therapy must be willing to be treated with a bisphosphonate while receiving study treatment.
- Administration of a live, attenuated vaccine within 4 weeks of Day 1 of Cycle 1 or anticipation that such a live, attenuated vaccine will be required during the study.
  Influenza vaccination should be given during influenza season only (approximately October through May in the Northern Hemisphere and approximately April through September in the Southern Hemisphere). Patients must agree not to receive live, attenuated vaccines (e.g., FluMist®) within 28 days prior to randomization, during treatment, or within 5 months following the last dose of atezolizumab.
- Second malignancy, except treated basal cell or localized squamous skin carcinomas, or other malignancy for which treatment was completed at least 3 years ago and for which there is no evidence of recurrence
- Significant medical diseases or conditions, as assessed by the Investigators and Sponsor that would substantially increase the risk/benefit ratio of participating in the study. This includes but is not limited to acute myocardial infarction within the last 6 months, unstable angina, uncontrolled diabetes mellitus, significant active infections, severely immunocompromised state, and congestive heart failure New York Heart Association (NYHA) Class II-IV.
- History of psychiatric illness or substance abuse likely to interfere with ability to comply with protocol requirements or give informed consent.
- Pregnancy or active breastfeeding

Study Endpoints:

Primary Endpoints:

- Dose-limiting toxicities (DLTs) and adverse events (AEs) according to NCI CTCAE, Version 4.03

- Recommended Phase 2 dose regimen for Hu5F9-G4, rituximab and atezolizumab
- Objective response as defined by the investigator according to the Lugano classification for lymphomas

Secondary Endpoints:

- PK profiles: Hu5F9-G4 and atezolizumab concentration versus time measurements and PK parameters of Hu5F9-G4 and atezolizumab including maximum plasma concentration ($C_{max}$), time to maximum concentration ($T_{max}$), terminal half-life ($t_{1/2}$), area under the curve (AUC),
- Anti-drug antibodies to Hu5F9-G4 and atezolizumab
- Duration of response (DOR), best overall response (BOR), progression-free survival (PFS), and overall survival (OS).

Exploratory Endpoints:

- Modulation of immune cell subsets in the peripheral blood and tumor microenvironment to include but not limited to T-cell, macrophage, and other immune cell subset frequency and activation
- Evaluation of PD-L1, CD47, SIRPα, CD20 expression on immune cells and/or tumor cells
- Evaluation of circulating tumor DNA and correlation to clinical response
- Pharmacodynamics markers of Hu5F9-G4 and atezolizumab biological activity potentially including, but not limited to, circulating cytokine profiles, T-cell receptor sequencing on circulating T cells, mass cytometry (CyTOF)/flow cytometry of circulating leukocytes, and T-cell activation studies.
- Correlation of anti-tumor response to molecular subtypes of NHL including, but not limited to, cell-of-origin in DLBCL, tumor mutational burden, BCL2, BCL6, and MYC mutation/expression status through genetic sequencing.

Intervention and Mode of Delivery:

Hu5F9-G4 is a humanized monoclonal blocking antibody against CD47, rituximab is a chimeric monoclonal antibody against CD20 and atezolizumab is a humanized monoclonal blocking antibody against PD-L1. Therapy with all monoclonal antibodies will be continued until unacceptable toxicity or loss of clinical benefit. The dosing schedule of all three antibodies are described below.

| Drug/Dose (IV) | Dose Schedule (Day per 28-day Cycle) | | | |
| --- | --- | --- | --- | --- |
| | Cycle 1 | Cycle 2 | Cycle 3-5 | Cycle 6+ |
| Hu5F9-G4 1 mg/kg (prime) | Day 1 | — | — | — |
| Hu5F9-G4 30 mg/kg (maintenance) | Day 8, 11 15, 22 | Day 1, 8, 15, 22 | Day 1, 15 | Day 1, 15 |
| Rituximab 375 mg/m² | Day 8, 15, 22 | Day 1 | Day 1 of Cycles 2 through 5 | Day 1 of Cycle 6, Day 1 every other Cycle Starting Cycle 8 |
| Atezolizumab 840mg | Day 9, 22 | Day 8, 22 | Day 8, 22 | Day 8, 22 |
| Abbreviations: IV = intravenous. | | | | |

Duration of Intervention and Evaluation:

Safety run-in: The safety and tolerability of the triplet combination in B-cell NHL Patients will be evaluated based on the aggregate adverse event profile with a decision to proceed to the expansion phase by the Clinical Trial Steering Committee (CTSC). Dose de-escalation of the triplet combination to an Hu5F9-G4 maintenance dose of 30 mg/kg may occur as determined by the CTSC based on the aggregate safety data.

Expansion: DLBCL patients will then be treated with the triplet combination at the recommended dose

Number of Patients: 35

Safety run-in cohort: 10

Expansion cohort: 25

Figure 14:
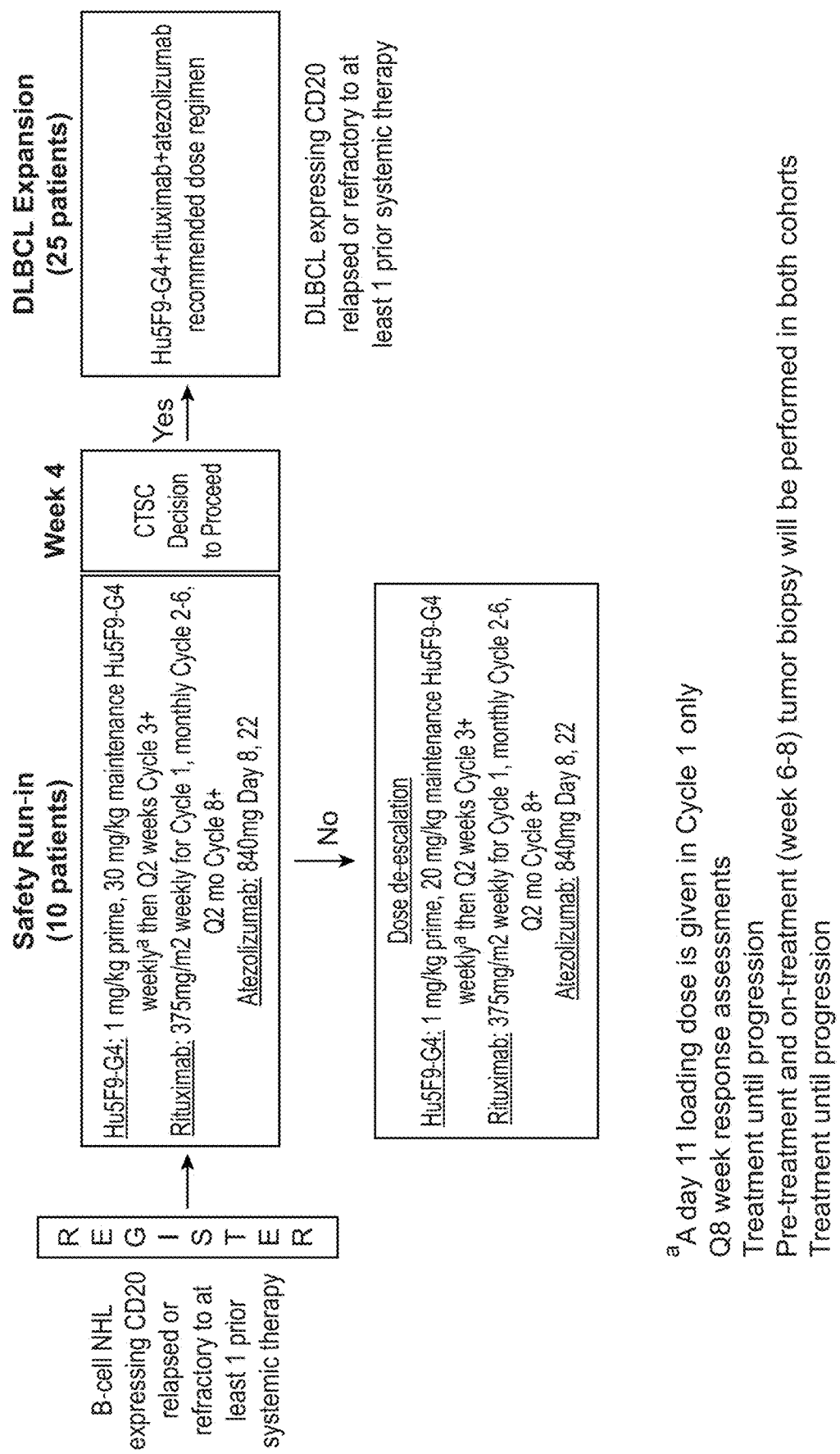
FIG. 14 shows a study design schema for: A Phase 1b Trial of Hu5F9-G4 in Combination with Rituximab and Atezolizumab in Patients with Relapsed/Refractory B-cell Non-Hodgkin's Lymphoma.

FIG. 14 shows a study design schema for: A Phase 1b Trial of Hu5F9-G4 in Combination with Rituximab and Atezolizumab in Patients with Relapsed/Refractory B-cell Non-Hodgkin's Lymphoma.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

The invention claimed is:

1. A method of effectively treating or reducing cancer burden with an overall response rate of at least 40% in human subjects, wherein the human subjects have Non-Hodgkin's lymphoma (NHL) and are refractory to rituximab, comprising:
   (a) determining, before administering steps, that the human subjects are refractory to rituximab;
   (b) selecting the refractory subjects for treatment;
   (c) administering to the refractory subjects for four weeks a first cycle comprising (1) a priming dose of anti-CD47 antibody at about 1 mg of antibody per kg of body weight at time 0 (T0), (2) a dose of at least 30 mg of the anti-CD47 antibody per kg of body weight once every week beginning one week after T0, and (3) a dose of 375 mg/m² of anti-CD20 antibody once every week; and
   (d) administering to the refractory subjects for four weeks a second cycle comprising (1) a dose of at least 30 mg of the anti-CD47 antibody per kg of body weight once every two weeks, and (2) a dose of 375 mg/m² of the anti-CD20 antibody once every four weeks;

thereby effectively treating or reducing cancer burden in the refractory subjects such that an overall response rate (ORR) of at least 40% is achieved.

2. The method of claim 1, wherein the NHL is indolent lymphoma, follicular lymphoma (FL), or diffuse large B cell lymphoma (DLBCL).

3. The method of claim 1, wherein the human subjects are relapsed or refractory to at least 2, 3, 4, 5, 6, 7, 8, 9, 10 or greater than 10 prior lines of cancer therapy.

4. The method of claim 1, wherein the anti-CD47 antibody comprises or consists of Hu5F9-G4.

5. The method of claim 1, wherein the anti-CD20 antibody comprises an Fc capable of at least one of ADCC and ADCP.

6. The method of claim 1, wherein the anti-CD20 antibody comprises or consists of rituximab.

7. The method of claim 1, wherein the first cycle further comprises a loading dose of at least 30 mg/kg on Day 11 (week 2).

8. The method of claim 1, wherein the second cycle is repeated as one or more additional cycles without limit or until a clinical benefit is reduced or lost.

9. The method of claim 1, wherein the human subjects are subjects having DLBCL.

10. The method of claim 1, wherein the human subjects are subjects having indolent lymphoma.

11. The method of claim 10, wherein the human subjects are subjects having FL.

12. The method of claim 1, comprising repeating steps (c) and (d) multiple times, wherein when steps (c) and (d) have been repeated 3 times, the anti-CD20 antibody is administered to the human subjects at a dose of 375 mg/m$^2$ once every eight weeks.

13. The method of claim 1, wherein the anti-CD47 antibody and the anti-CD20 antibody are administered to the human subjects until the subjects lose a clinical benefit.

14. The method of claim 1, wherein the anti-CD47 antibody is Hu5F9-G4 and the anti-CD20 antibody is rituximab.

15. The method of claim 1, wherein the cancer has been classified as CD20$^+$ based on histopathology, flow cytometry, molecular classification, or a combination thereof.

16. The method of claim 1, wherein the anti-CD47 antibody is Hu5F9-G4, which has the heavy chain sequence set forth in SEQ ID NO: 1 and the light chain sequence set forth in SEQ ID NO: 2.

17. The method of claim 1, wherein the anti-CD47 antibody and the anti-CD20 antibody are administered concurrently.

18. The method of claim 1, wherein the anti-CD47 antibody and the anti-CD20 antibody are administered sequentially.

19. The method of claim 1, wherein the anti-CD47 antibody is administered intravenously.

20. The method of claim 1, wherein the anti-CD20 antibody is administered intravenously.

* * * * *